US012709601B2

(12) United States Patent
Gouverneur et al.

(10) Patent No.: US 12,709,601 B2
(45) Date of Patent: Aug. 18, 2026

(54) RADIOLABELLED COMPOUND

(71) Applicant: OXFORD UNIVERSITY INNOVATION LIMITED, Oxford (GB)

(72) Inventors: Veronique Gouverneur, Oxford (GB); Bart Cornelissen, Oxford (GB); Thomas Charles Wilson, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 17/041,991

(22) PCT Filed: Mar. 26, 2019

(86) PCT No.: PCT/GB2019/050852

§ 371 (c)(1),
(2) Date: Sep. 25, 2020

(87) PCT Pub. No.: WO2019/186135

PCT Pub. Date: Oct. 3, 2019

(65) Prior Publication Data

US 2021/0284613 A1 Sep. 16, 2021

(30) Foreign Application Priority Data

Mar. 27, 2018 (GB) .................................... 1804924

(51) Int. Cl.

| | |
|---|---|
| ***C07D 237/32*** | (2006.01) |
| ***A61K 51/04*** | (2006.01) |
| ***C07B 59/00*** | (2006.01) |
| ***C07F 7/08*** | (2006.01) |

(52) U.S. Cl.

CPC ........ *C07D 237/32* (2013.01); *A61K 51/0459* (2013.01); *C07B 59/002* (2013.01); *C07F 7/0812* (2013.01); *C07B 2200/05* (2013.01)

(58) Field of Classification Search

CPC ............ C07D 237/32; A61K 51/0459; C07B 59/002; C07F 7/0812

USPC ........................................................ 424/1.89

See application file for complete search history.

(56) References Cited

U.S. PATENT DOCUMENTS

| | | | | |
|---|---|---|---|---|
| 7,981,889 | B2 | 7/2011 | Barr Martin | |
| 2005/0059663 | A1* | 3/2005 | Martin ................ | C07D 409/12 514/248 |
| 2013/0309170 | A1* | 11/2013 | Reiner .............. | A61K 51/0459 424/1.89 |
| 2021/0038748 | A1 | 2/2021 | Reiner | |

FOREIGN PATENT DOCUMENTS

| | | | | |
|---|---|---|---|---|
| AU | 2003253418 | B2 * | 4/2010 | .......... A61K 9/0095 |
| CA | 2935857 | A1 | 7/2015 | |
| GB | 2415430 | A | 12/2005 | |
| WO | 2004080976 | A1 | 9/2004 | |
| WO | 2012074840 | A2 | 6/2012 | |
| WO | 2015140572 | A1 | 9/2015 | |
| WO | 2016033293 | A1 | 3/2016 | |
| WO | 2016164771 | A1 | 10/2016 | |
| WO | WO-2017181918 | A1 * | 10/2017 | ............ C07B 59/00 |

OTHER PUBLICATIONS

Taylor et al. J. Am. Chem. Soc. 2017, 139, 8267-8276. (Year: 2017).*

Everson University of Rochester Dissertation 2013, 1-290. (Year: 2013).*

Wutz et al. Greene's Protective Groups in Organic Synthesis 2006, 894-926. (Year: 2006).*

Grierson et al. Nucl. Med. Biol. 2000, 27, 143-156. (Year: 2000).*

Coelho et al. J. Med. Chem. 2007, 50, 6476-6484.*

Franca PDdS, Kossatz S, Brand C, Zanoni DK, Roberts S, Guru N, Adilbay D, Mauguen A, Mayor CV, Weber WA, Schöder H, Ghossein RA, Ganly I, Patel SG, Reiner T. "A Phase I Study of a PARP1-targeted Topical Fluorophore for the Detection of Oral Cancer" DOI:10.21203/rs.3.rs-252422/v1.

Heiko Schoder, Paula Demetrio De Souza Franca, Reiko Nakajima, Eva Burnazi, Sheryl Roberts, Christian Brand, Milan Grkovski, Audrey Mauguen, Mark P. Dunphy, Ronald A. Ghossein, Serge K. Lyashchenko, Jason S. Lewis, Joseph A. O'Donoghue, Ian Ganly, Snehal G. Patel, Nancy Y. Lee, and Thomas Reiner "Safety and Feasibility of PARP1/2 Imaging with 18F-PARPi in Patients with Head and Neck Cancer" Clin. Cancer Res. 2020; 26: 3110-6.

Brandon Carney, Susanne Kossatz, Benjamin H. Lok, Valentina Schneeberger, Kishore K. Gangangari, Naga Vara Kishore Pillarsetty, Wolfgang A. Weber, Charles M. Rudin, John T. Poirier, Thomas Reiner "Target engagement imaging of PARP inhibitors in small-cell lung cancer" Nature Communications, 9, 176 (2018).

Chung Ying Chan, Kel Vin Tan, Bart Cornelissen, "PARP Inhibitors in Cancer Diagnosis and Therapy" 10.1158/1078-0432.CCR-20-2766.

Florian Guibbal, Samantha L. Hopkins, Anna Pacelli, Patrick G. Isenegger, Michael Mosley, Julia Baguna Torres, Gemma M. Dias, Damien Mahaut, Rebekka Hueting, Veronique Gouverneur, Bart Cornelissen "[18F]AZD2461, an Insight on difference in PARP Binding Profiles for DNA Damage Response PET Imaging" Mol Imaging Biol (2020) 22:1226, 1234.

Florian Guibbal, Patrick G. Isenegger, Thomas C. Wilson, Anna Pacelli, Damien Mahaut, Jeroen B. I. Sap, Nicholas J. Taylor, Stefan Verhoog, Sean Preshlock, Rebekka Hueting, Bart Cornelissen, Véronique Gouverneur "Manual and automated Cu-mediated radiosynthesis of the PARP inhibitor [18F]olaparib" Nature Protocols 15, 2020, 1525-1541.

(Continued)

*Primary Examiner* — Michael G. Hartley
*Assistant Examiner* — Sean R Donohue
(74) *Attorney, Agent, or Firm* — CHRISTENSEN O'CONNOR JOHNSON KINDNESS PLLC

(57) ABSTRACT

The present invention relates to radiolabelled olaparib and in particular [18 F]olaparib, a process for producing radiolabelled olaparib, and uses of radiolabelled olaparib in medical imaging.

11 Claims, 25 Drawing Sheets

(56) References Cited

OTHER PUBLICATIONS

Ferenc Gallyas Jr, Balazs Sumegi, Csaba Szabo "Role of Akt activation in PARP inhibitor resistance in cancer" Cancers, 2020, 12, 532.
Nicola J Curtin, Csaba Szabo "Poly (ADP-ribose) polymerase inhibition: past, present and future" Nature Reviews Drug Discovery, 2020, 19, 711-736.
Csaba Szabo, Vanessa Martins, Lucas Liaudet "Poly (ADP-Ribose) Polymerase Inhibition in Acute Lung Injury. A Reemerging Concept" American Journal of Respiratory Cell and Molecular Biology 2020, 63, 5, 571-590.
Stephen A. Jannetti, Giuseppe Carlucci, Brandon Carney, Susanne Kossatz, Larissa Shenker, Lukas M. Carter, Beatriz Salinas, Christian Brand, Ahmad Sadique, Patrick L. Donabedian, Kristen M. Cunanan, Mithat Gonen, Vladimir Ponomarev, Brian M. Zeglis, Mark M. Souweidane, Jason S. Lewis, Wolfgang A. Weber, John L. Humm, Thomas Reiner "PARP-1-Targeted Radiotherapy in Mouse Models of Glioblastoma" J Nucl Med 2018; 59:1225-1233.
Beatriz Salinas, Christopher P. Irwin, Susanne Kossatz, Alexander Bolaender, Gabriela Chiosis, Nagavarakishore Pillarsetty, Wolfgang A. Weber, Thomas Reiner "Radioiodinated PARP1 tracers for glioblastoma imaging" . EJNMMI Research (2015) 5:46.
Giacomo Pirovano, Stephen A. Jannetti, Lukas M. Carter, Ahmad Sadique, Susanne Kossatz, Navjot Guru, Paula Demetrio De Souza Franca, Masatomo Maeda, Brian M. Zeglis, Jason S. Lewis, John L. Humm, Thomas Reiner "Targeted Brain Tumor Radiotherapy Using an Auger Emitter" DOI: 10.1158/1078-0432.CCR-19-2440.
Thomas C. Wilson, Nagavarakishore Pillarsetty, Thomas Reiner "A one-pot radiosynthesis of [18F]PARPi" J Label Compd Radiopharm. 2020; 63: 419-425.
Sean W. Reilly, LauraN. Puentes, Alexander Schmitz, Chia-Ju Hsieh, Chi-Chang Weng, Catherine Hou, Shihong Li, Yin-Ming Kuo, Prashanth Padakanti, Hsiaoju Lee, Aladdin A. Riad, Mehran Makvandi, Robert H. Mach "Synthesis and evaluation ofan AZD2461[18F]PET probein non-humanprimates revealsthe PARP-1 inhibitor to be non-blood-brainbarrierpenetrant" Bioorganic Chemistry 83 (2019) 242-249243.
Lord, C.J. & Ashworth, A. The DNA damage response and cancer therapy. Nature 481, 287-294, 2012.
O'Connor, M.J. Targeting the DNA Damage Response in Cancer. Molecular cell 60, 547-560, 2015.
Murai, J., et al. Trapping of PARP1 and PARP2 by Clinical PARP Inhibitors. Cancer research 72, 5588-5599 (2012).
Marchand, J.R., et al. investigating the allosteric reverse signalling of PARP inhibitors with microsecond molecular dynamic simulations and fluorescence anisotropy. Biochimica et biophysica acta 1844, 1765-1772, 2014.
Lowery, M.A., et al. An emerging entity: pancreatic adenocarcinoma associated with a known BRCA mutation: clinical descriptors, treatment implications, and future directions. The oncologist 16, 1397-1402, 2011.
Lesueur, P., et al. Poly-(ADP-ribose)-polymerase inhibitors as radiosensitizers: a systematic review of pre-clinical and clinical human studies. Oncotarget 8, 69105-69124, 2017.
Rosado, M.M., Bennici, E., Novelli, F. & Pioli, C. Beyond DNA repair, the immunological role of PARP-1 and its siblings. Immunology 139, 428-437, 2013.
Livraghi, L. & Garber, J.E. Parp inhibitors in the management of breast cancer: current data and future prospects. BMC medicine 13, 188, 2015.
Kim, Y., et al. Reverse the Resistance to PARP Inhibitors. International journal of biological sciences 13, 198-208, 2017.
O'Driscoll, L., et al. MDR1/P-glycoprotein and MRP-1 drug efflux pumps in pancreatic carcinoma. Anticancer research 27, 2115-2120, 2007.
Park, S.H., et al. Expression of DNA Damage Response Molecules PARP1, gammaH2AX, BRCA1, and BRCA2 Predicts Poor Survival of Breast Carcinoma Patients. Translational oncology 8, 239-249, 2015.
Pournazari, P., et al. B-lymphoblastic leukemia/lymphoma: overexpression of nuclear DNA repair protein PARP-1 correlates with antiapoptotic protein Bcl-2 and complex chromosomal abnormalities. Human pathology 45, 1582-1587 (2014).
Rojo, F., et al. Nuclear PARP-1 protein overexpression is associated with poor overall survival in early breast cancer. Annals of oncology: official journal of the European Society for Medical Oncology 23, 1156-1164, 2012.
Knight, J.C., Koustoulidou, S. & Cornelissen, B. Imaging the DNA damage response with PET and SPECT. Eur J Nucl Med Mol Imaging 44, 1065-1078, 2017.
Carney, B., Kossatz, S. & Reiner, T. Molecular Imaging of PARP; Journal of nuclear medicine: official publication, Society of Nuclear Medicine 58, 1025-1030, 2017.
Reiner, T., Keliher, E.J., Earley, S., Marinelli, B. & Weissleder, R. Synthesis and in vivo imaging of a 18F-labeled PARP1 inhibitor using a chemically orthogonal scavenger-assisted high-performance method. Angew Chem Int Ed Engl 50, 1922-1925, 2011.
Carlucci, G., et al. Dual-Modality Optical/PET Imaging of PARP1 in Glioblastoma. Molecular Imaging and Biology 17, 348-855, 2015.
Zmulda et al., J. Med. Chem., Nov. 12, 2015, 58(21), 8683-8693.
Janetti et al., J. Nucl. Med., Aug. 1, 2018, vol. 59, No. 8, 1225-1233.
Sean W. Reilly et al., "Rapid Cu-Catalyzed [211At]Astatination and [125I]Iodination of Boronic Esters at Room Temperature", Organic Letters 2018, 20 (7), 1752-1755.
Tredwell, M., et al., Angew Chem Int Ed Engl 53, 7751-7755, 2014.
Preshlock, S., Tredwell, M. & Gouverneur, V., Chemical reviews 116, 719-766, 2016.
Preshlock, S., et al., Chem Commun (Camb) 52, 8361-8364, 2016.
Taylor, N.J., et al., Journal of the American Chemical Society 139, 8267-8276, 2017.
Thomas C. Wilson et al."Radiosynthesis of SPECT tracers via a copper mediated 123I iodination of (hetero)aryl boron reagents"; Chem.Commun., 2016, 52, 13277.
Pangborn, A.B., Giardello, M.A., Grubbs, R.H., Rosen, R.K. & Timmers, F.J. Safe and convenient procedure for solvent purification. Organometallics 15, 1518-1520, 1996.
Ravat, P., Borozdina, Y., Ito, Y., Enkelmann, V. & Baumgarten, M. Crystal Engineering of Tolane Bridged Nitronyl Nitroxide Biradicals: Candidates for Quantum Magnets. Cryst. Growth Des. 14, 5840-5846, 2014.
Outerbridge, V.M., Landge, S.M., Tamaki, H. & Torok, B. Microwave-Promoted Solid-Acid Catalyzed One-Pot Synthesis of Phthalazinones. Synthesis 11, 1801-1806, 2009.
Nezhawy, A.O.H., Gaballah, S.T. & Radwan, M.A.A. Studying the reactivity of (phthalazin-1(2H)-on-2-yl)methyl trichloroacetimidate towards different C- and O-nucleophiles. Tetrahedron Letters 50, 6646-6650, 2009.
J. M. Murphy, C. C. Tzschucke, J. F. Hartwig, Org. Lett., 2007, 9, 757-760.
T. Furuya, T. Ritter Org. Lett., 2009, 11, 2860-2863.
Cornelissen, B., Hu, M., McLarty, K., Costantini, D. & Reilly, R.M. Cellular penetration and nuclear importation properties of 111In-labeled and 123I-labeled HIV-1 tat peptide immunoconjugates in BT-474 human breast cancer cells. Nucl Med Biol 34, 37-46, 2007.
Thurber, G.M., Reiner, T., Yang, K.S., Kohler, R.H. & Weissleder, R. Effect of small-molecule modification on single- cell pharmacokinetics of PARP inhibitors. Molecular cancer therapeutics 13, 986-995, 2014.
Reiner, T., et al. Imaging therapeutic PARP inhibition in vivo through bioorthogonally developed companion imaging agents. Neoplasia 14, 169-177, 2012.
Lee, J., Siemann, D.W., Koch, C.J. & Lord, E.M. Direct relationship between radiobiological hypoxia in tumors and monoclonal antibody detection of EF5 cellular adducts. Int J Cancer 67, 372-378 (1996).
Kersemans, V., et al. Hypoxia imaging using PET and SPECT: the effects of anesthetic and carrier gas on [Cu]-ATSM, [Tc]-HL91 and [F]-FMISO tumor hypoxia accumulation. PloS one 6, e25911 (2011).

(56) References Cited

OTHER PUBLICATIONS

Hueting, R., et al. A comparison of the behavior of (64)Cu-acetate and (64)Cu-ATSM in vitro and in vivo. J Nucl Med 55, 128-134, 2014.
Carney, B., et al. Non-invasive PET Imaging of PARP1 Expression in Glioblastoma Models. Molecular imaging and biology: MIB : the official publication of the Academy of Molecular Imaging 18, 386-392, 2016.
Kossatz, S., Weber, W.A. & Reiner, T. Optical Imaging of PARP1 in Response to Radiation in Oral Squamous Cell Carcinoma. PloS one 11, e0147752, 2016.
Jiang, Y., et al. Hypoxia Potentiates the Radiation-Sensitizing Effect of Olaparib in Human Non-Small Cell Lung Cancer Xenografts by Contextual Synthetic Lethality. International journal of radiation oncology, biology, physics 95, 772-781, 2016.
Helleday, T., Petermann, E., Lundin, C., Hodgson, B. & Sharma, R.A. DNA repair pathways as targets for cancer therapy. Nat Rev Cancer 8, 193-204, 2008.
Thurber, G.M., et al. Single-cell and subcellular pharmacokinetic imaging allows insight into drug action in vivo. Nature communications 4, 1504, 2013.
Makvandi, M., et al. A Radiotracer Strategy to Quantify PARP-1 Expression In Vivo Provides a Biomarker That Can Enable Patient Selection for PARP Inhibitor Therapy. Cancer research 76, 4516-4524, 2016.
Oplustil O'Connor, L., et al. The PARP Inhibitor AZD2461 Provides Insights into the Role of PARP3 Inhibition for Both Synthetic Lethality and Tolerability with Chemotherapy in Preclinical Models. Cancer Res 76, 6084-6094, 2016.
Buchfellner, A., et al. A New Nanobody-Based Biosensor to Study Endogenous PARP1 In Vitro and in Live Human Cells. PloS one 11, e0151041, 2016.
Zhou et al., Bioorganic & Medicinal Chemistry, vol. 22, 2014, pp. 1700-1707.
Thomas L. Andersen, Troels Skrydstrup et al, "Efficient 11C-Carbonylation of Isolated Aryl Palladium Complexes for PET: Application to Challenging Radiopharmaceutical Synthesis", Journal Of The American Chemical Society, vol. 137, No. 4, Jan. 26, 2015 (Jan. 26, 2015), pp. 1548-1555.
Lennox and Lloyd Jones, Chem. Soc. Rev., 2014, 43, 412.
Farmer, H., McCabe, N., Lord, C. et al. "Targeting the DNA repair defect in BRCA mutant cells as a therapeutic strategy." Nature 434, 917-921 (2005).
Jorge Rios and Shannon Puhalla, Oncology, vol. 25 No 11, vol. 25, Issue 11, Oct. 15, 2011.
"Bond Polarity and Bond Strength", Chemistry LibreText article downloaded from https://chem.libretexts.org/Bookshelves/Inorganic_Chemistry/Book%3A_Introduction_to_Inorganic_Chemistry_(Wikibook)/01%3A_Review_of_Chemical_Bonding/1.04%3A_Bond_Polarity_and_Bond_Strength on Aug. 12, 2022, last modified on May 1, 2022 (3 pages).
Nair, R et al. "Tale of Two Protecting Groups—Boc vs SEM—for Directed Lithiation and C—C Bond Formation on a Pyrrolopyridazinono Core", Organic Process Research & Development, 2016, 20, pp. 1370-1376.
Wilson, T., "Late stage 18F-fluorination and 123I-Iodination for PET and SPECT Imaging" Thesis, Somerville College, University of Oxford, Sep. 5, 2018, 329 pages.
Blom, E., et al.; "[18F]/19F exchange in fluorine containing compounds for potential use in 18F-labelling strategies";. Journal of Labelled Compounds and Radiopharmaceuticals, pp. 504-511; Aug. 25, 2009.
Brooks, A. F., et al.; "Fluorine-18 Radiochemistry"; Handbook of Radiopharmaceuticals. (2021), pp. 251-289.
"ICH guideline Q3D (R2) on elemental impurities"; EMA/CHMP/ICH/353369/2013 ( https://www.ema.europa.eu/en/documents/scientific-guideline/international-conference-harmonisation-technical-requirements-registration-pharmaceuticals-human-use-ich-q3d-elemental-impurities-step-5-revision-2_en.pdf ).

* cited by examiner

Fig. 1A (a) Olaparib (Lynparza)

Astra Zeneca AZD2281
PARP Inhibitor
FDA Approved 2014
$IC_{50}$ 5 nm, LogP 0.8

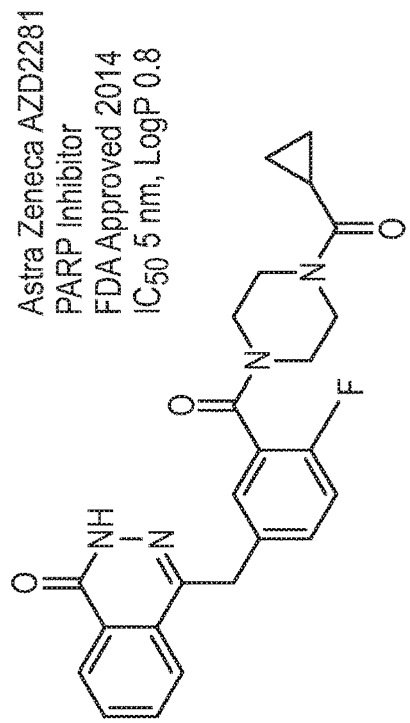

(b) Previous Work: $[^{18}F]$PARPi

Reiner et.al. 2015
In vivo translation
Deviation from Parent Molecule
$IC_{50}$ 2.8 nm, LogP 1.8

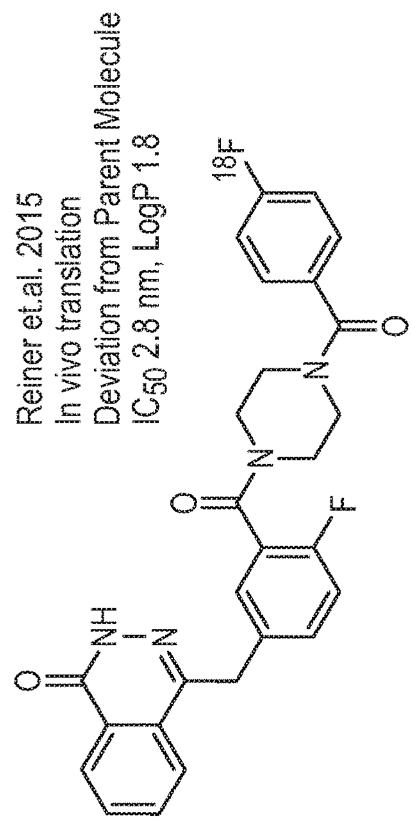

(c) Previous Work: $[^{11}C]$Olaparib

Skrydstrup et. al. 2015
Direct $^{11}C$ Analogue
Unstable Precursor
No In vivo studies
$IC_{50}$ 5 nm, LogP 0.8

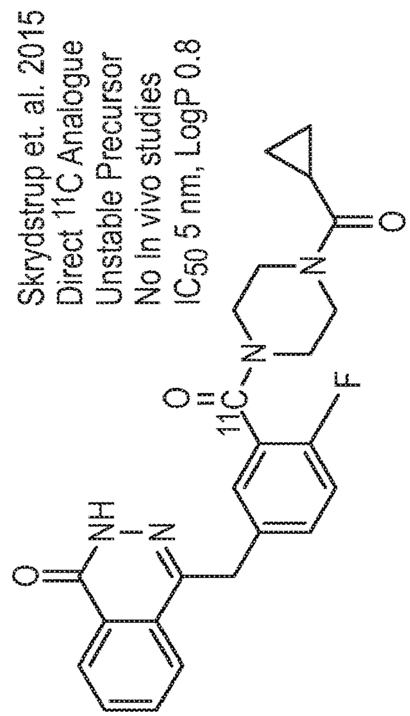

(d) Present invention: $[^{18}F]$Olaparib

Stable Precursor
Direct $^{18}F$ Analogue
In vivo translation
$IC_{50}$ 5 nm, LogP 0.8

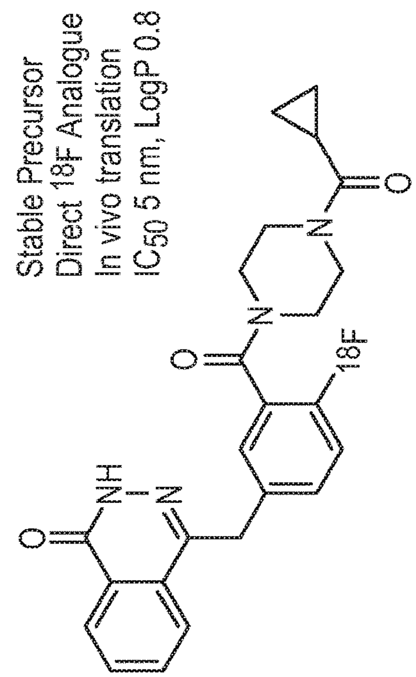

Fig. 1B (e) Previous Work: [$^{18}$F]PARPi-FL

Reiner et.al. 2015
In vivo translation
Deviation from Parent Molecule
Suseptible to defluorination in vivo
$IC_{50}$ 12 nm LogP N/A

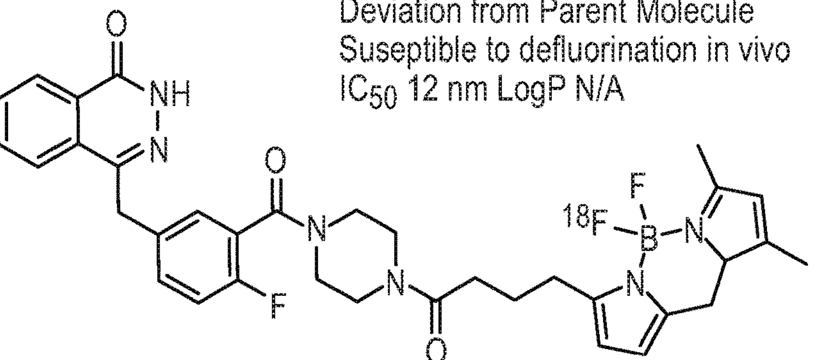

(f) Previous Work: [$^{18}$F]BO

Weissleder et.al . 2011
In vivo translation
Deviation from Parent Molecule
$IC_{50}$ 18 nm LogP N/A

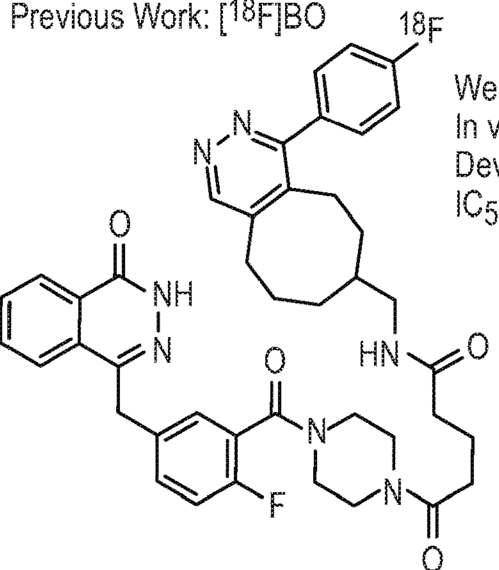

(g) Previous Work: [$^{123}$I]PARPi, [$^{131}$I]PARPi

Pimlott et.al. 2015,
Janetti et al. 2018 ,
In vivo translation
Deviation from Parent Molecule
Suseptible to defluorination in vivo
$IC_{50}$ 3.3 nm, LogP 3.00

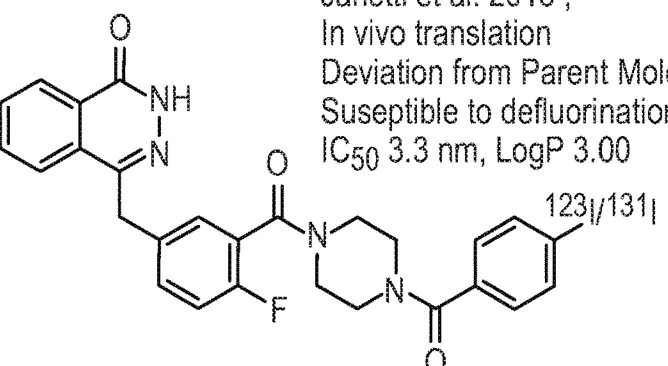

(h) Previous Work: [$^{211}$At]PARPi

Reilly et.al. 2018
No In vivo studies
Deviation from Parent Molecule
$IC_{50}$ N/A, LogP N/A

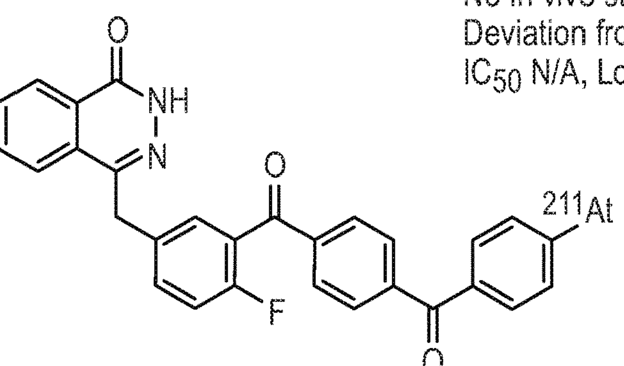

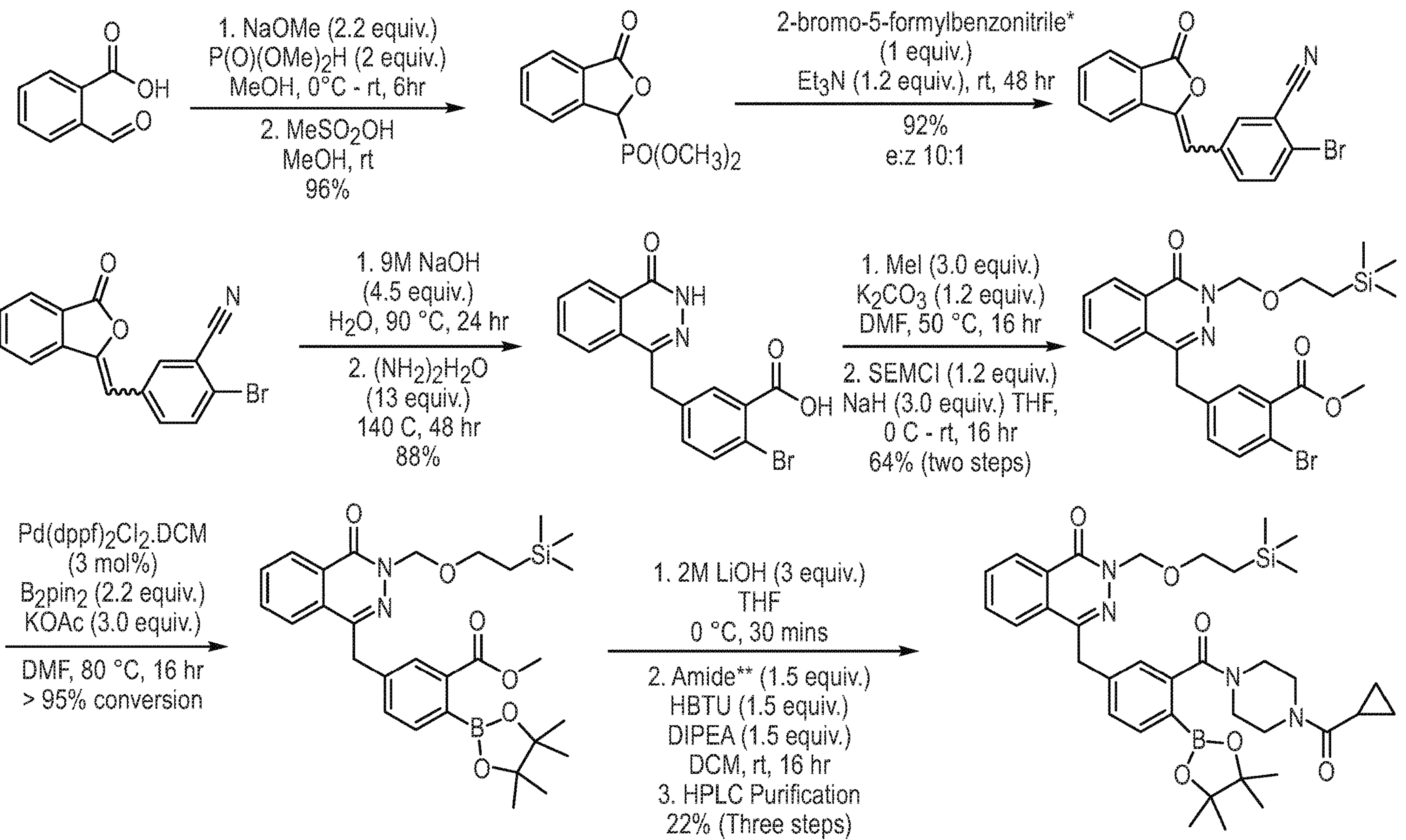
Fig. 3
1. NaOMe (2.2 equiv.)
P(O)(OMe)2H (2 equiv.)
MeOH, 0°C - rt, 6hr
2. MeSO2OH
MeOH, rt
96%
2-bromo-5-formylbenzonitrile*
(1 equiv.)
Et3N (1.2 equiv.), rt, 48 hr
92%
e:z 10:1
1. 9M NaOH
(4.5 equiv.)
H2O, 90 °C, 24 hr
2. (NH2)2H2O
(13 equiv.)
140 C, 48 hr
88%
1. MeI (3.0 equiv.)
K2CO3 (1.2 equiv.)
DMF, 50 °C, 16 hr
2. SEMCl (1.2 equiv.)
NaH (3.0 equiv.) THF,
0 C - rt, 16 hr
64% (two steps)
Pd(dppf)2Cl2.DCM
(3 mol%)
B2pin2 (2.2 equiv.)
KOAc (3.0 equiv.)
DMF, 80 °C, 16 hr
> 95% conversion
1. 2M LiOH (3 equiv.)
THF
0 °C, 30 mins
2. Amide** (1.5 equiv.)
HBTU (1.5 equiv.)
DIPEA (1.5 equiv.)
DCM, rt, 16 hr
3. HPLC Purification
22% (Three steps)

Fig. 8
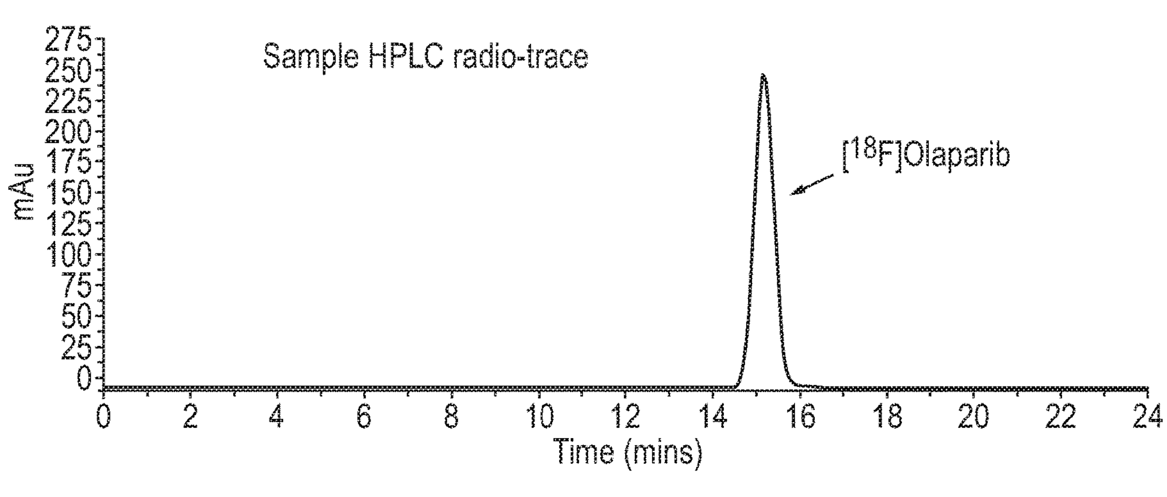
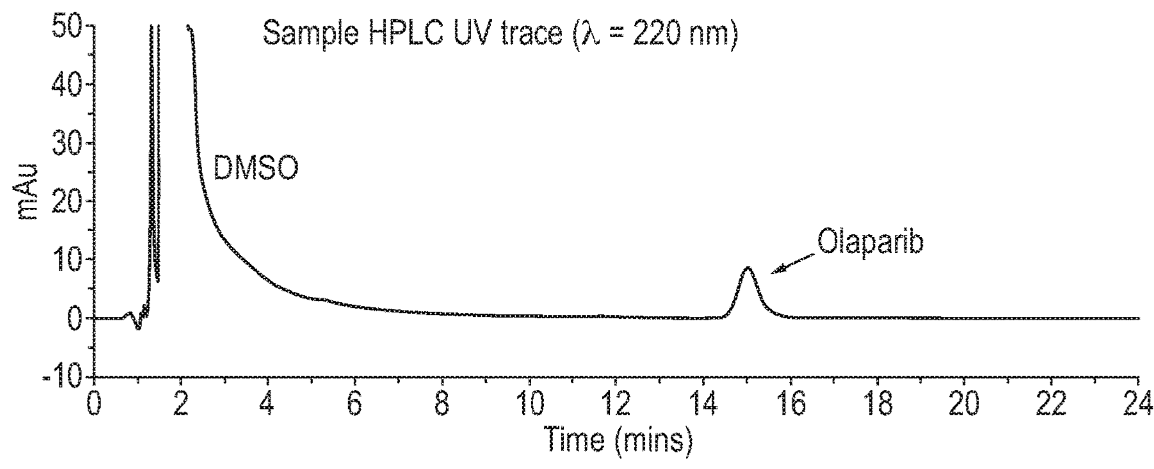
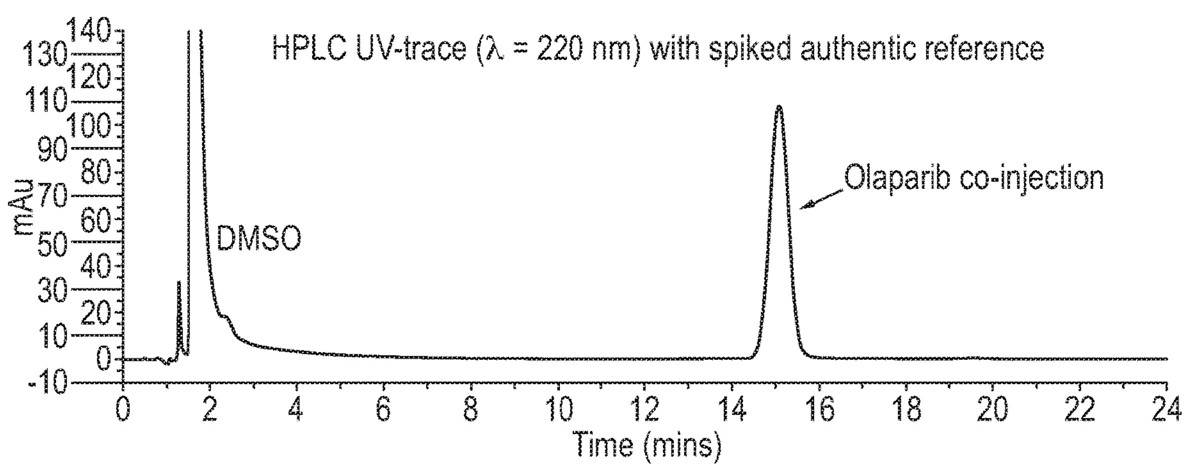

| Injection Number | Activity (MBq) | Area (mA*min) | Mmol ($*10^{-7}$) | Injected | Molar Activity ($GBq.\mu mol^{-1}$) |
|---|---|---|---|---|---|
| 1[a] | 2.0 | 9.16 | 9.16 | 2.7 | 7.2 |
| 2[a] | 1.4 | 4.82 | 4.82 | 1.3 | 10.4 |
| 3[a] | 1.6 | 18.29 | 18.29 | 5.6 | 2.8 |
| 4[a] | 0.7 | 2.73 | 2.73 | 0.71 | 9.8 |
| 5[a] | 3.1 | 5.06 | 5.06 | 1.4 | 21.3 |
| 6[b] | 1.1 | 3.67 | 3.67 | 1.0 | 10.9 |
| 7[b] | 1.6 | 2.86 | 2.86 | 0.75 | 21.3 |
| 8[b] | 1.7 | 2.58 | 2.58 | 0.66 | 25.7 |
| 9[b] | 2.2 | 25.79 | 25.79 | 8.1 | 2.7 |
| 10[b] | 2.6 | 5.79 | 5.79 | 1.7 | 15.5 |

[18F]olaparib
+ olaparib block
% Radioactivity / mg
250
150
0
Panc-1
MiaPaCa
Capan-1

% Radioactivity / mg
100
50
0
DMSO
+ olaparib
+ talazoparib
+ rucaparib

Panc-1
MiaPaCa
Capan-1
% Radioactivity / mg
150
100
50
0
0
2
4
6
8
10
10 + block
Dose [Gy]

Time post IR (10 Gy) [h]
Capan-1
Mia-PaCa-2
Panc-1
0 2 24 48
0 2 24 48
0 2 24 48
PARP-1-
β-actin -

Panc-1
Miapaca-2
Capan-1
PARP-1 / β-actin ratio
200
150
100
50
0
0
2
24
48
Time post IR (10 Gy) [h]

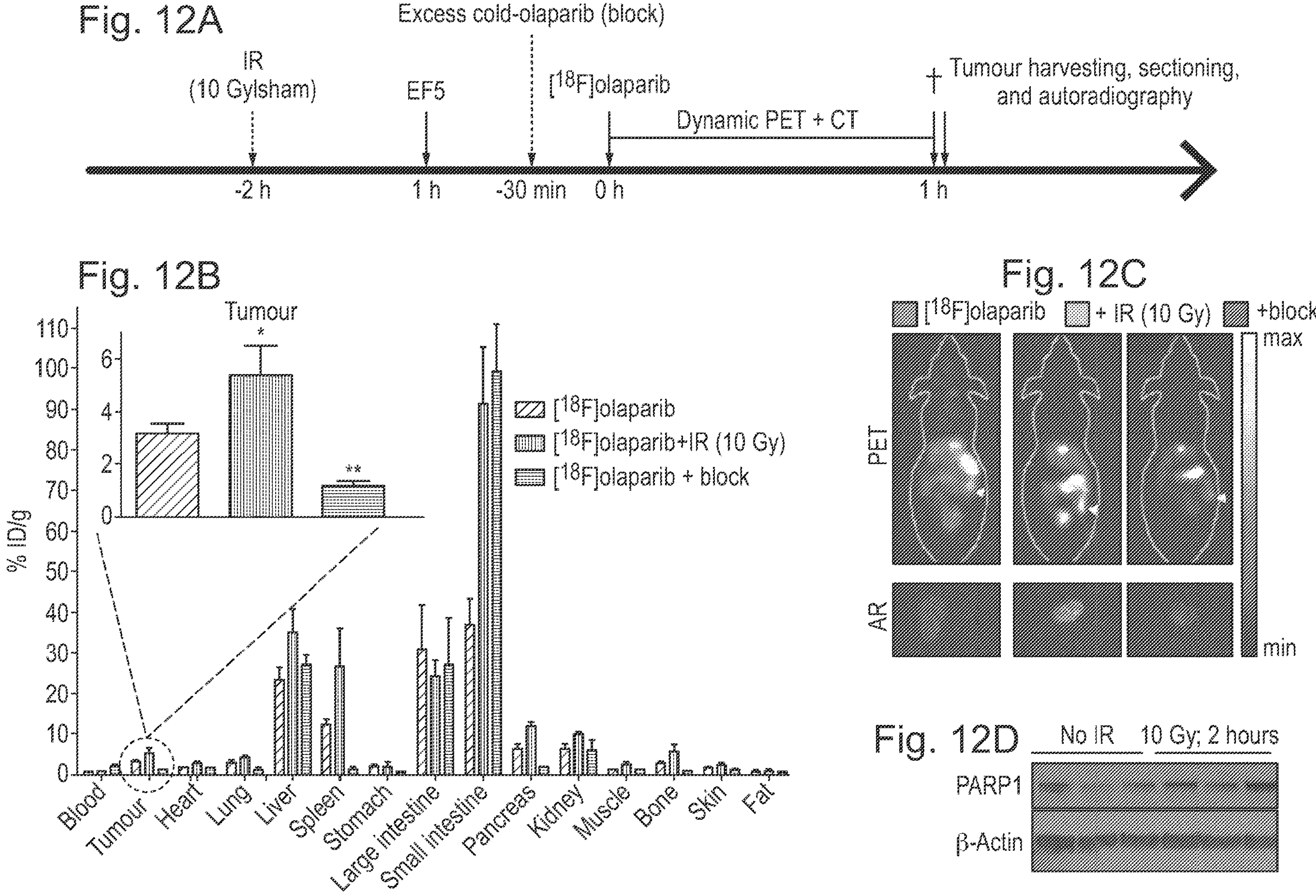

Fig. 12A
Excess cold-olaparib (block)
IR
(10 Gylsham)
EF5
[18F]olaparib
Dynamic PET + CT
Tumour harvesting, sectioning, and autoradiography
-2 h
1 h
-30 min
0 h
1 h
Fig. 12B
Tumour
% ID/g
[18F]olaparib
[18F]olaparib+IR (10 Gy)
[18F]olaparib + block
Blood
Tumour
Heart
Lung
Liver
Spleen
Stomach
Large intestine
Small intestine
Pancreas
Kidney
Muscle
Bone
Skin
Fat
Fig. 12C
[18F]olaparib
+ IR (10 Gy)
+block
max
min
PET
AR
Fig. 12D
No IR
10 Gy; 2 hours
PARP1
β-Actin 0 10 0 10 0 10 Gy

PARP1 -

β-actin -

Panc1

Capan-1

CaNT

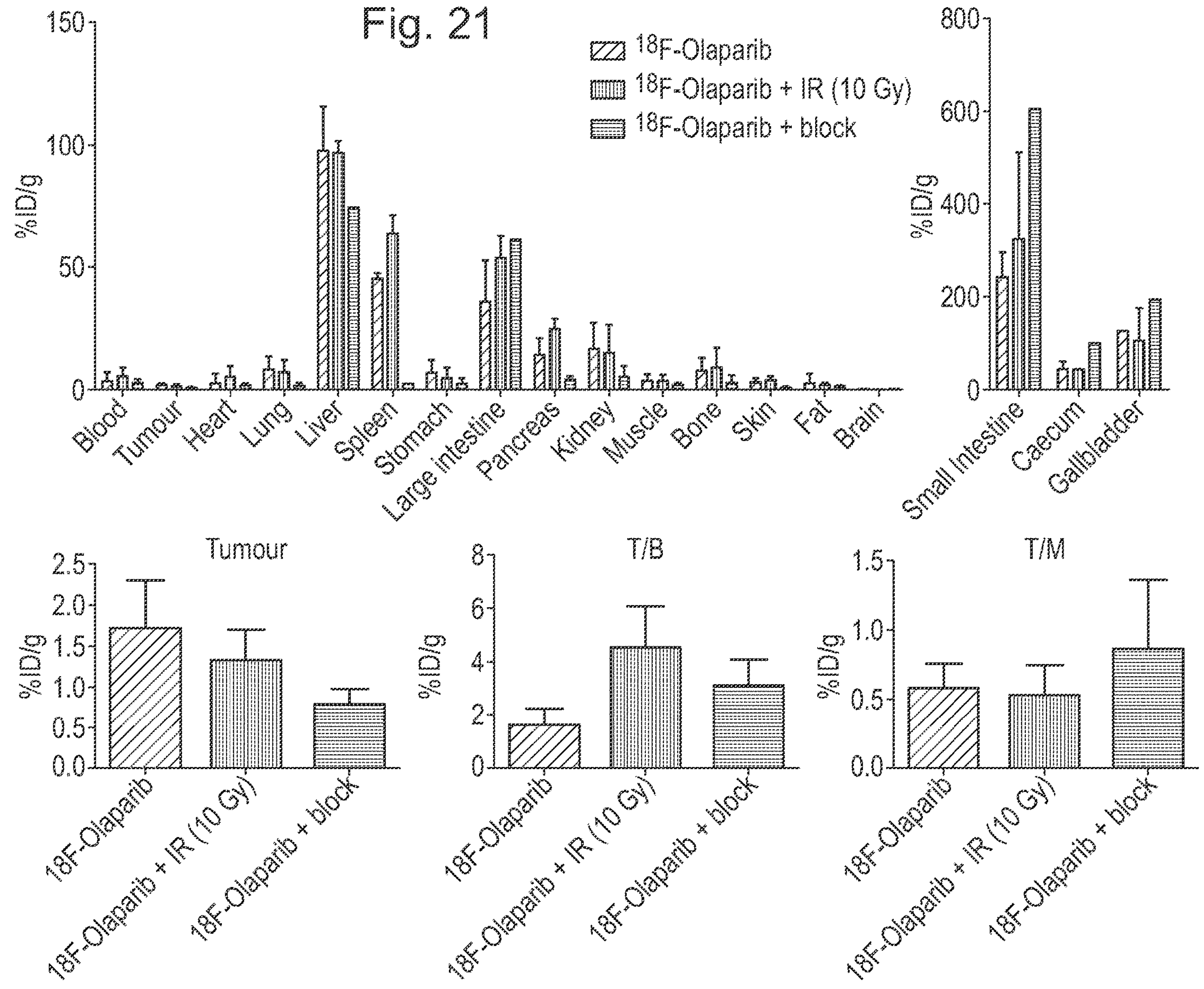
Fig. 21
$^{18}$F-Olaparib
$^{18}$F-Olaparib + IR (10 Gy)
$^{18}$F-Olaparib + block
%ID/g
150
100
50
0
Blood
Tumour
Heart
Lung
Liver
Spleen
Stomach
Large intestine
Pancreas
Kidney
Muscle
Bone
Skin
Fat
Brain
%ID/g
800
600
400
200
0
Small intestine
Caecum
Gallbladder
Tumour
%ID/g
2.5
2.0
1.5
1.0
0.5
0.0
18F-Olaparib
18F-Olaparib + IR (10 Gy)
18F-Olaparib + block
T/B
%ID/g
8
6
4
2
0
18F-Olaparib
18F-Olaparib + IR (10 Gy)
18F-Olaparib + block
T/M
%ID/g
1.5
1.0
0.5
0.0
18F-Olaparib
18F-Olaparib + IR (10 Gy)
18F-Olaparib + block Fig. 26
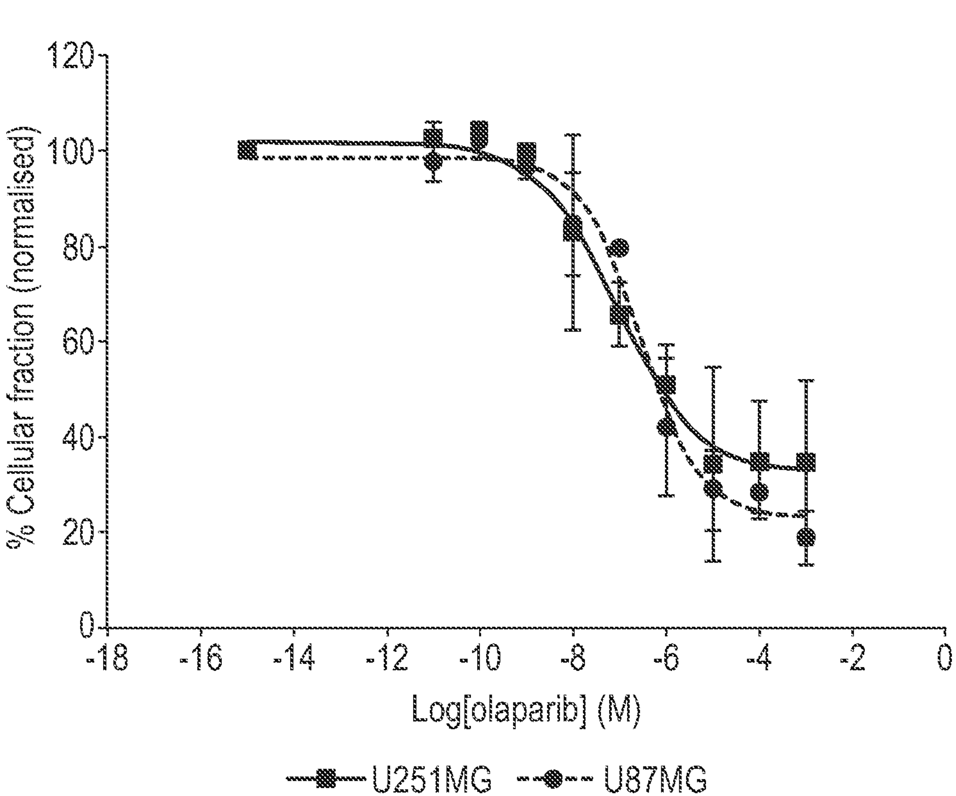
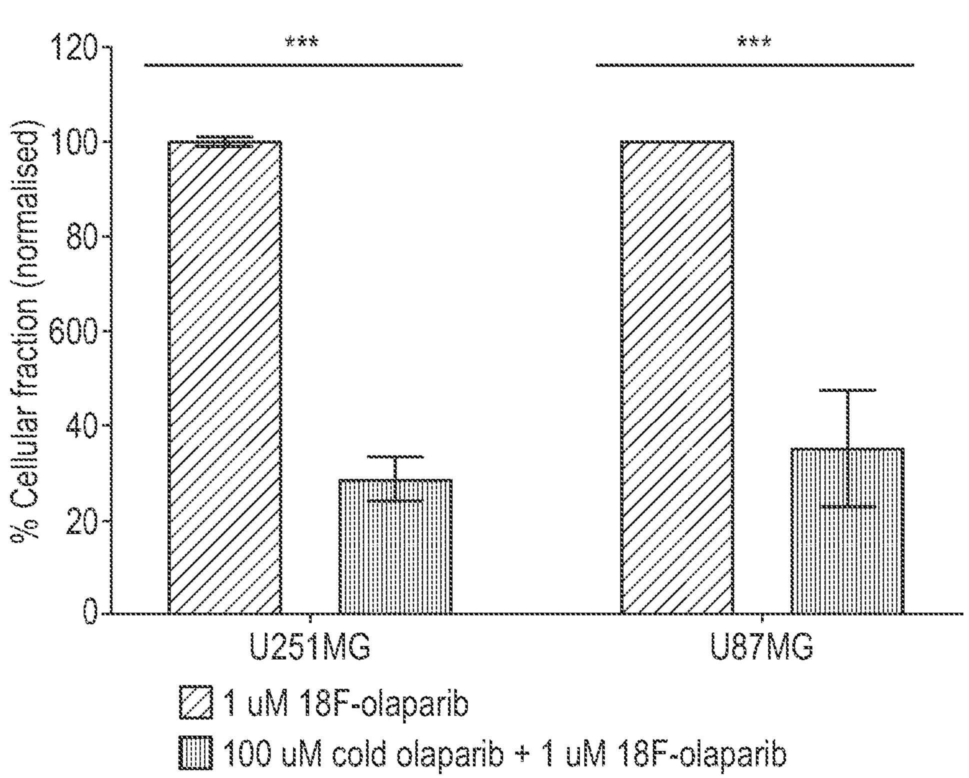

U251MG
0.5 ug
1.0 ug
4 ug
8 ug
%ID/g
0
20
40
60
80
100
120
Blood
Tumour
Heart
Lung
Liver
Spleen
Stomach
Large intestine
Small intestine
Pancreas
Kidney
Muscle
Skin
Fat
Bone
Caecum
Gallbladder
Brain
Organs

RADIOLABELLED COMPOUND

FIELD OF THE INVENTION

The present invention relates to a radiolabelled compound, a process for producing the radiolabelled compound, and uses of the radiolabelled compound in medical imaging.

BACKGROUND TO THE INVENTION

Genomic instability in tumour tissue results from oncogenic and replicative stress, exogenous genotoxic insults, and tumour-specific DNA repair defects (Lord, C. J. & Ashworth, A. The DNA damage response and cancer therapy. Nature 481, 287-294, 2012). Manipulating this genomic instability provides numerous therapeutic opportunities, and inhibitors of DNA damage repair (DDR) enzymes have been explored as anti-cancer drugs (O'Connor, M. J. Targeting the DNA Damage Response in Cancer. Molecular cell 60, 547-560, 2015). This includes Poly(ADP-ribose) Polymerase (PARP) inhibitors. PARP enzymes are part of a 17-member subfamily of enzymes with similar function. PARP1-3 sense single strand DNA damage by binding to nicked DNA via its zinc-finger domains and play important roles in Base Excision Repair (BER), with PARP-1 being the most studied. PARP inhibitors reduce the enzymes' catalytic activity (formation of poly-ADP-ribose [PAR] chains from NAD*) by binding to their NAD*binding pocket and interfere with the ability of the PARP-enzyme-inhibitor complex to dissociate from damaged DNA (Murai, J., et al. Trapping of PARP1 and PARP2 by Clinical PARP Inhibitors. Cancer research 72, 5588-5599 (2012); Marchand, J. R., et al. Investigating the allosteric reverse signalling of PARP inhibitors with microsecond molecular dynamic simulations and fluorescence anisotropy. Biochimica et biophysica acta 1844, 1765-1772, 2014). PARP inhibitors have been extensively studied as cancer drugs, either as single agents, as radiation sensitizers, or as part of combination therapies, and are especially effective in tumours with BRCA mutations (Lowery, M. A., et al. An emerging entity: pancreatic adenocarcinoma associated with a known BRCA mutation: clinical descriptors, treatment implications, and future directions. The oncologist 16, 1397-1402, 2011).

Radiation sensitization using PARP inhibition is known to act via several mechanisms, including straightforward inhibition of DNA repair and synthetic lethality. Further mechanisms also include inhibition of chromatin remodelling, vasodilatory effects, decreased hypoxia, contextual lethality in hypoxic cells, replication-dependent radiation sensitization, G2/M arrest leading to time cooperation (Lesueur, P., et al. Poly-(ADP-ribose)-polymerase inhibitors as radiosensitizers: a systematic review of pre-clinical and clinical human studies. Oncotarget 8, 69105-69124, 2017) and a possible role for reduction of Treg cells (Rosado, M. M., Bennici, E., Novelli, F. & Pioli, C. Beyond DNA repair, the immunological role of PARP-1 and its siblings. Immunology 139, 428-437, 2013). The first clinically approved and most studied PARP inhibitor is olaparib (ku-0059436, AZ2281, Lynparza®), whose structure is shown in FIG. 1A(a). It inhibits the catalytic activity of PARP isoforms 1 and 2, and, albeit to a lesser extent, PARP3. At present, over 100 clinical trials are ongoing using olaparib as a single drug, or in combination with other chemotherapy, immunotherapy, or radiation therapies.

Resistance to PARP inhibition, however, is common. It has been reported that 30-70% of patients with mutations in DDR machinery do not respond to therapies including PARP inhibitors (Livraghi, L. & Garber, J. E. PARP inhibitors in the management of breast cancer: current data and future prospects. BMC medicine 13, 188, 2015). Apart from some molecular mechanisms (Kim, Y., et al. Reverse the Resistance to PARP Inhibitors. International journal of biological sciences 13, 198-208, 2017) resistance is often due to low PARP enzyme expression, or the inability of the drug to penetrate tumour tissue, or part of the tumour tissue, due to increased interstitial pressure and desmoplasia—especially relevant in pancreatic adenocarcinomas; or an intact blood-brain-barrier, in the case of brain tumours or brain metastases. Increased expression of drug efflux pumps may also prevent drug uptake in the tumour, most relevant for gastro-intestinal and pancreatic tumours (O'Driscoll, L., et al. MDR1/P-glycoprotein and MRP-1 drug efflux pumps in pancreatic carcinoma. Anticancer research 27, 2115-2120, 2007).

Recently, several reports have suggested that accurately measuring and monitoring PARP expression in vivo provides critical information regarding disease prognosis (Park, S. H., et al. Expression of DNA Damage Response Molecules PARP1, gammaH2AX, BRCA1, and BRCA2 Predicts Poor Survival of Breast Carcinoma Patients. Translational oncology 8, 239-249, 2015) as it has been found to independently correlate with worse outcomes in breast, ovarian, and other tumours (Pournazari, P., et al. B-lymphoblastic leukemia/lymphoma: overexpression of nuclear DNA repair protein PARP-1 correlates with antiapoptotic protein Bcl-2 and complex chromosomal abnormalities. Human pathology 45, 1582-1587 (2014); Rojo, F., et al. Nuclear PARP-1 protein overexpression is associated with poor overall survival in early breast cancer. Annals of oncology: official journal of the European Society for Medical Oncology 23, 1156-1164, 2012). Assessment of DDR signalling activation may also contribute to genotoxic treatment evaluation, following chemo- or radiotherapy. To date, PARP expression and BRCA-ness status in tumours can be determined by immunohistochemistry or genetic sequencing on biopsy samples. However, many tumours are known to be extremely heterogeneous—due to their increased genomic instability—yet this heterogeneity is overlooked when sampling tissue from a single biopsy site. Furthermore, acquisition of reliable and high-quality biopsies is a significantly invasive and non-trivial procedure in many disease sites, such as lung, brain, or pancreas. Given these challenges, scientists have sought to utilise alternative methods to measure PARP expression in vivo, especially PARP-1. Of those molecular imaging techniques available, positron emission tomography (PET) has been shown to be ideal. PET allows for non-invasive, whole-body, repeatable visualisation of olaparib delivery and its binding to PARP-1-3 (Knight, J. C., Koustoulidou, S. & Cornelissen, B. Imaging the DNA damage response with PET and SPECT. Eur J Nucl Med Mol Imaging 44, 1065-1078, 2017). In recent years, molecules based on olaparib labelled with positron emitting radionuclides such as $^{18}F$ or $^{124}I$ have been investigated for this purpose (for recent reviews, see Knight, J. C., Koustoulidou, S. & Cornelissen, B. Imaging the DNA damage response with PET and SPECT. Eur J Nucl Med Mol Imaging 44, 1065-1078, 2017 and Carney, B., Kossatz, S. & Reiner, T. Molecular Imaging of PARP; Journal of nuclear medicine: official publication, Society of Nuclear Medicine 58, 1025-1030, 2017).

In 2011, Reiner et. al., via an inverse electron demand Diels-Alder reaction, reported access to [$^{18}F$]BO (see FIG. 1B(f)), a molecule which deviates significantly from that of the parent molecule (Reiner, T., Keliher, E. J., Earley, S., Marinelli, B. & Weissleder, R. Synthesis and in vivo imaging of a $^{18}$F-labeled PARP1 inhibitor using a chemically orthogonal scavenger-assisted high-performance method. Angew Chem Int Ed Engl 50, 1922-1925, 2011). Subsequently, a range of fluorescently and radiolabelled derivatives have been reported, of which both [$^{18}$F]PARPi-FL (see FIG. 1B(e)) and [$^{18}$F]PARPi (see FIG. 1A(b)) have been used to successfully measure uptake and distribution of PARP isoforms in vivo (Carney, B., Kossatz, S. & Reiner, T. Molecular Imaging of PARP. Journal of nuclear medicine: official publication, Society of Nuclear Medicine 58, 1025-1030, 2017; Carlucci, G., et al. Dual-Modality Optical/PET Imaging of PARP1 in Glioblastoma. Molecular Imaging and Biology 17, 848-855, 2015). Derivatives with halogen radioisotopes other than fluorine have also been synthesised, including [$^{123}$I]PARPi and [$^{131}$I]PARPi (see FIG. 1B(g)) and [$^{211}$At]PARPi (see FIG. 1B(h)) (Pimlott et al., J. Med. Chem., 2015, Nov. 12, 58(21), 8683-93; Janetti et al., J. Nucl. Med., Aug. 1, 2018, vol. 59, no. 8, 1225-1233; Reilly et al., Org. Lett., 2018, 20 (7), pp 1752-1755).

Whilst these works have allowed for significant strides to be made in the understanding of DDR pathways, the structural deviation from the parent molecule makes many of these radiolabelled derivatives incompatible for further development due to a combination of poor $IC_{50}$, lipophicity or in vivo behaviour such as defluorination (Carlucci, G., et al. Dual-Modality Optical/PET Imaging of PARP1 in Glioblastoma. Molecular imaging and biology: MIB: the official publication of the Academy of Molecular Imaging 17, 848-855, 2015). This has led to scientists pursuing more innovative transformations. In 2015, Andersen, Skydstrup et. al., reported an intricate three-component carbonylation of aryl palladium species with the positron emitting isotope carbon-11 in the form of $^{11}$C carbon monoxide (Andersen, T. L., et al. Efficient 11C-carbonylation of isolated aryl palladium complexes for PET: application to challenging radiopharmaceutical synthesis. J Am Chem Soc 137, 1548-1555, 2015). This gave the first direct, radiolabelled analogue of Olaparib, [$^{11}$C]olaparib (see FIG. 1A(c)). The unstable nature of the palladium precursor however, detracts from what is otherwise an elegant reaction. $^{18}$F-labelling would allow for a longer shelf life, and results in intrinsically better spatial resolution.

SUMMARY OF THE INVENTION

The present invention provides access, for the first time, to the direct $^{18}$F-radiolabelled analogue of the FDA-approved PARP inhibitor olaparib, [$^{18}$F]olaparib, whose chemical structure is given in formula (I):

(I)

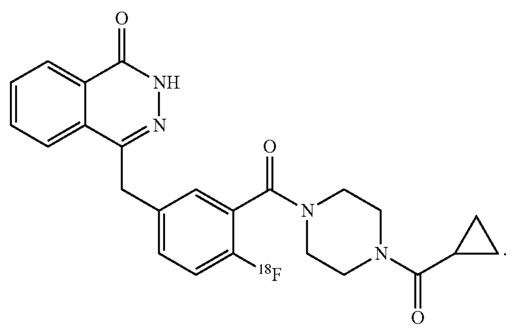

The inventors have achieved synthesis of [$^{18}$F]olaparib via a copper-mediated $^{18}$F-fluorodeboronation of an organoboron precursor compound bearing an N-[2-(trialkylsilyl) ethoxy]methyl] protecting group. Previous work from the same group had demonstrated that copper-mediated $^{18}$F-fluorodeboronation can be used to synthesise $^{18}$F-fluoroarenes (Tredwell, M., et al., Angew Chem Int Ed Engl 53, 7751-7755, 2014; Preshlock, S., et al., Chem Commun (Camb) 52, 8361-8364, 2016; Preshlock, S., Tredwell, M. & Gouverneur, V., Chemical reviews 116, 719-766, 2016; Taylor, N. J., et al., Journal of the American Chemical Society 139, 8267-8276, 2017; WO 2015/140572). In that earlier work it was found that copper plays a key role as a catalyst in the reaction, and is typically present in the form of a Cu(II) salt or complex. In the present work, however, the inventors found that an unprotected organoboron precursor to [$^{18}$F]olaparib would be incompatible with such $^{18}$F-fluorodeboronation, potentially due to interference of the phthalazone nitrogen with the copper catalyst. A tert-butyloxycarbonyl (BOC) protecting group was also found not to work.

Unexpectedly, the issue was overcome by employing an N-[2-(trialkylsilyl)ethoxy]methyl] protecting group on the phthalazone nitrogen of the organoboron precursor compound. It was counterintuitive to test an N-[2-(trialkylsilyl) ethoxy]methyl] protecting group because conventional wisdom dictates that the $^{18}$F-fluoride used for the $^{18}$F-fluorodeboronation reaction would in that case react with the trialkylsilyl group and that the $^{18}$F-fluorodeboronation reaction would not therefore take place. Due to the known tendancy of silicon to be highly fluorophilic, and of trialkylsilyl groups to be susceptible to cleavage upon treatment with fluoride to form the corresponding trialkylsilyl fluoride (as commonly occurs when N-[2-(trialkylsilyl)ethoxy] methyl] protecting groups are removed by tetrabutylammonium fluoride (TBAF) in deprotection reactions), silicon-containing protecting groups are generally avoided by those skilled in the art of $^{18}$F radiochemistry when radiolabelling compounds with $^{18}$F-fluoride.

Surprisingly, however, N-[2-(trialkylsilyl)ethoxy]methyl] was successfully employed as the protecting group on the phthalazone nitrogen. Furthermore, N-[2-(trialkylsilyl) ethoxy]methyl] has certain key advantages in the context of radiosynthesising an $^{18}F^-$ labeled agent for in vivo administration. Deprotection can be performed easily and quickly under mild conditions and, for example, without the need for a heavy metal catalyst that would complicate subsequent purification. Difficult, lengthy and/or complicated deprotection and purification steps are desirably avoided after an $^{18}$F label has been introduced, owing to the need for quick administration of the radiolabelled compound to the patient after radiosynthesis due to the short half-life of $^{18}$F. N-[2-(trialkylsilyl)ethoxy]methyl] was therefore a highly advantageous albeit entirely counterintuititve choice of protecting group.

Having successfully produced [$^{18}$F]olaparib, the inventors demonstrated that [$^{18}$F]olaparib can be used to measure the distribution, uptake, and PARP-binding of olaparib using PET imaging in mouse models of pancreatic ductal adenocarcinoma (PDAC). Furthermore, the use of [$^{18}$F]olaparib for detecting DNA damage following external beam irradiation was demonstrated, as well as its relationship with tumour hypoxia. [$^{18}$F]olaparib was therefore found to have great potential for non-invasive tumour imaging and monitoring of radiation damage. Imaging of PARP using the radiolabelled inhibitor is proposed for patient selection, outcome prediction, dose optimisation, genotoxic therapy evaluation, and target engagement imaging of novel PARP-targeting agents. When translated to the clinic, PET imaging with [$^{18}$F]olaparib will allow: (a) better patient selection, by determining tumour drug uptake; (b) measurement of the biological effects of genotoxic cancer treatment, such as chemo- and radiotherapy; and (c) allow better patient stratification, making the use of PARP inhibitors even more effective, albeit in a more stringently selected patient population.

Thus, the invention has provided, for the first time, successful radiosynthesis of [$^{18}$F]olaparib and its in vivo translation for PET imaging.

Accordingly, the invention provides a compound which is [$^{18}$F]olaparib or a pharmaceutically acceptable salt thereof.

The invention also provides a pharmaceutical composition comprising (a) a compound which is [$^{18}$F]olaparib or a pharmaceutically acceptable salt thereof, and (b) a pharmaceutically acceptable carrier or diluent.

The invention further provides a process for producing a compound of formula (I)

(I)

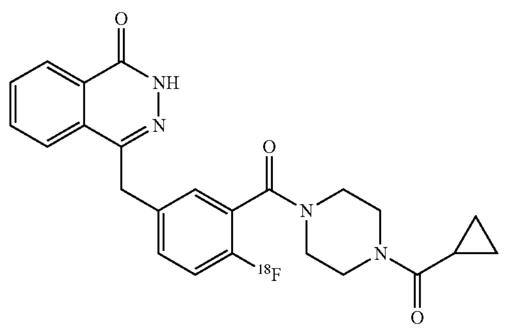

which process comprises:

(i) treating an organoboron compound of formula (II) with $^{18}F^-$ and a copper compound:

(II)

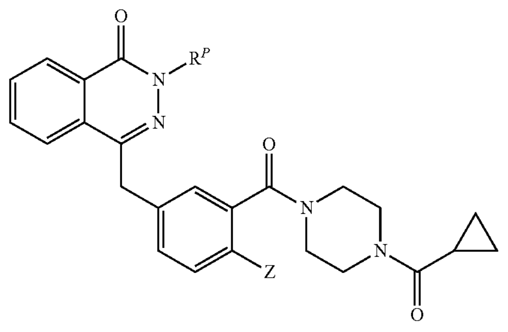

wherein

Z is a boronic ester group, a boronic acid group, a boronate group or a trifluoroborate group; and $R^P$ is a protecting group of formula (III)

(III)

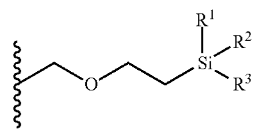

wherein $R^1$ is $C_{1-6}$ alkyl;

$R^2$ is $C_{1-6}$ alkyl; and $R^3$ is $C_{1-6}$ alkyl;

and (ii) removing the protecting group $R^P$ to produce the compound of formula (I).

It is possible to label organoboron precursor compounds with halogen radioisotopes other than fluorine, by copper-mediated halodeboronation of the organoboron precursor compound (see, for example, Sean W. Reilly, Mehran Makvandi, Kuiying Xu, and Robert H. Mach "Rapid Cu-Catalyzed [$^{211}$At]Astatination and [$^{125}$I]Iodination of Boronic Esters at Room Temperature"; Organic Letters; DOI: 10.1021/acs.orglett.8b00232; and Thomas C. Wilson, Greg McSweeney, Sean Preshlock, Stefan Verhoog, Matthew Tredwell, Thomas Caillyac and Veronique Gouverneur "Radiosynthesis of SPECT tracers via a copper mediated $^{123}$I iodination of (hetero)aryl boron reagents"; Chem. Commun., 2016, 52, 13277, and FIGS. 1B(g) and 1B(h) herein). The process of the invention can also therefore be used to produce other radiolabelled analogues of olaparib useful in medical imaging, and in particular $^{123}$I, $^{125}$I, $^{131}$I, $^{211}$At or $^{76}$Br radiolabelled analogues of olaparib. Thus, compounds of formula (Ia) may be produced (Ia)

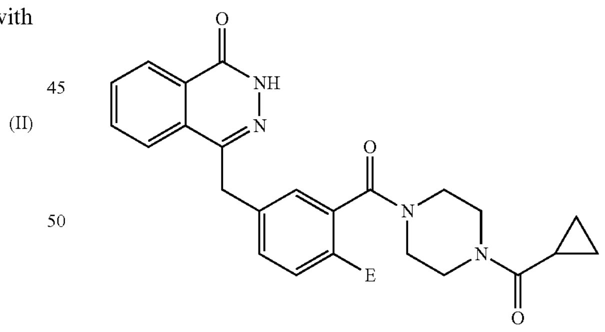

wherein E may be $^{131}$I, $^{125}$I, $^{123}$I, $^{211}$At or $^{76}$Br. Instead of treating the organoboron compound of formula (II) with $^{18}F^-$ and the copper compound in step (i) of the process, step (i) of the process comprises treating the organoboron compound of formula (II) with the copper compound and any one of $^{123}I^-$, $^{125}I^-$, $^{131}I^-$, $^{211}At^-$ and $^{76}Br^-$. Any suitable source of $^{123}I^-$, $^{125}I^-$, $^{131}I^-$, $^{211}At^-$ or $^{76}Br^-$ may be employed. The sodium salt, i.e. Na[E] wherein E is $^{131}$I, $^{125}$I, $^{123}$I, $^{211}$At or $^{76}$Br, may for example be used.

Accordingly, in one aspect the invention provides a process for producing a compound of formula (Ia)

(Ia)

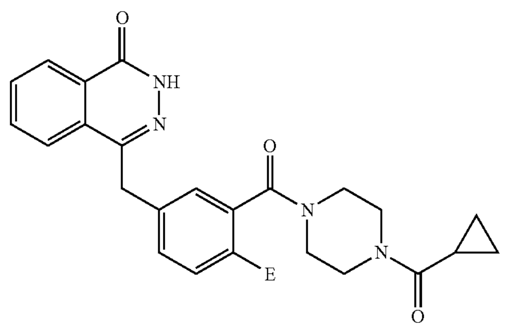

which process comprises:

(i) treating an organoboron compound of formula (II) with a copper compound and $E^-$, wherein E is a halogen radioisotope:

(II)

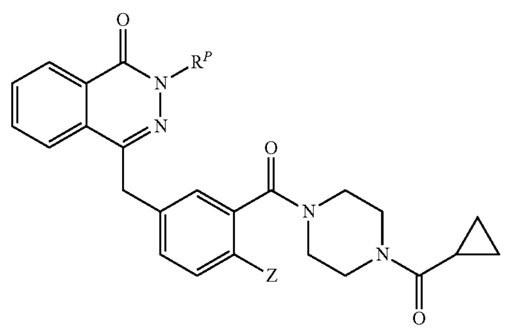

wherein

Z is a boronic ester group, a boronic acid group, a boronate group or a trifluoroborate group; and $R^P$ is a protecting group of formula (III)

(III)

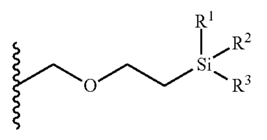

wherein $R^1$ is $C_{1-6}$ alkyl;

$R^2$ is $C_{1-6}$ alkyl; and $R^3$ is $C_{1-6}$ alkyl;

and (ii) removing the protecting group $R^P$ to produce the compound of formula (Ia).

E may be $^{131}I$, $^{125}I$, $^{123}I$, $^{211}At$, $^{76}Br$ or $^{18}F$. Often, E is $^{131}I$, $^{125}I$, $^{123}I$, $^{211}At$ or $^{76}Br$. E may for instance be $^{125}I$, $^{123}I$ or $^{211}At$.

Typically, step (i) of the process comprises treating the organoboron compound of formula (II) with the copper compound and Na[E], wherein E is as defined above, and may for instance be $^{131}I$, $^{125}I$, $^{123}I$, $^{211}At$ or $^{76}Br$.

The process for producing the compound of formula (Ia) may be as further defined herein for the process of the invention for producing the compound of formula (I), [$^{18}F$] olaparib. Thus, reagents, reaction conditions and further process steps may be as further defined hereinbelow for the process of the invention for producing the compound of formula (I). For instance, in the process for producing the compound of formula (Ia): $R^1$, $R^2$ and $R^3$ may be as further defined hereinbelow. The copper compound employed may be as further defined hereinbelow. Z in the compound of formula (II) may be as further defined hereinbelow. The ratio of the amount of the organoboron compound to the amount of the copper compound may be as further defined hereinbelow. Treating the organoboron compound of formula (II) with $E^-$ and the copper compound may be carried out in the presence of a solvent, and optionally the solvent may be as further defined hereinbelow. The organoboron compound, the copper compound and the $E^-$ may heated, for instance at a temperature as defined herein, e.g. from 80° C. to 150° C. Alternatively, the reaction may be carried out at room temperature. The step (ii) of removing the protecting group $R^P$ may be as further defined hereinbelow. The process for producing the compound of formula (Ia) may further comprise quenching the reaction by adding a polar protic solvent, optionally as further defined hereinbelow. The process may further comprise recovering the compound of formula (Ia), for instance by preparative HPLC or semi-preparative HPLC. The process for producing the compound of formula (Ia) may be conducted in an automated synthesizer.

The invention also provides a compound of formula (Ia)

(Ia)

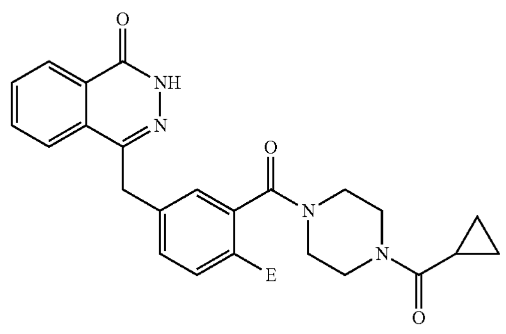

wherein E is a halogen radioisotope, or a pharmaceutically acceptable salt thereof.

In the compound of formula (Ia), E may be $^{131}I$, $^{125}I$, $^{123}I$, $^{211}At$, $^{76}Br$ or $^{18}F$. Often, E is $^{131}I$, $^{125}I$, $^{123}I$, $^{211}At$ or $^{76}Br$. E may for instance be $^{125}I$, $^{123}I$ or $^{211}At$.

The invention also provides a pharmaceutical composition comprising (a) a compound of formula (Ia) or a pharmaceutically acceptable salt thereof, and (b) a pharmaceutically acceptable carrier or diluent.

The invention additionally provides an organoboron compound of formula (II)

(II)

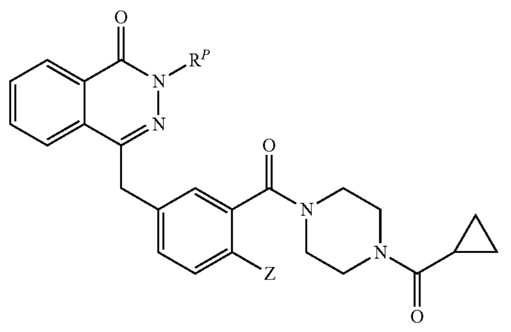

wherein

Z is a boronic ester group, a boronic acid group, a boronate group or a trifluoroborate group; and $R^P$ is a group of formula (III)

(III)

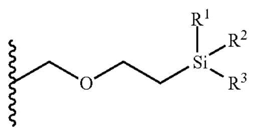

wherein $R^1$ is $C_{1-6}$ alkyl;

$R^2$ is $C_{1-6}$ alkyl; and $R^3$ is $C_{1-6}$ alkyl.

The invention further provides an organoboron compound of formula (X)

(X)

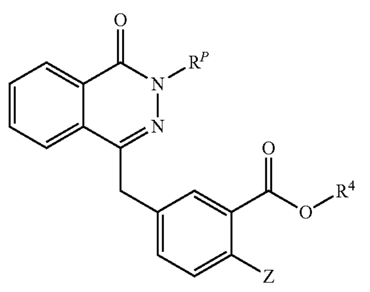

wherein

Z is a boronic ester group, a boronic acid group, a boronate group or a trifluoroborate group;

$R^P$ is a group of formula (IT)

(III)

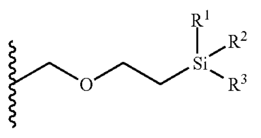

wherein $R^1$ is $C_{1-6}$ alkyl;

$R^2$ is $C_{1-6}$ alkyl;

$R^3$ is $C_{1-6}$ alkyl; and $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl.

The invention further provides a compound of formula (XI)

(XI)

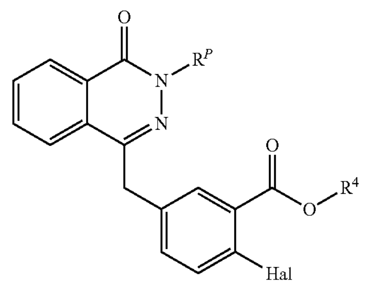

wherein

Hal is Br, Cl, I or At;

$R^P$ is a group of formula (III)

(III)

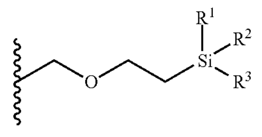

wherein $R^1$ is $C_{1-6}$ alkyl;

$R^2$ is $C_{1-6}$ alkyl;

$R^3$ is $C_{1-6}$ alkyl; and $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl.

The invention additionally provides a method of imaging a subject, comprising administering to the subject a compound which is a compound of formula (Ta), for instance $[^{18}F]$olaparib, or a pharmaceutically acceptable salt thereof, and imaging the subject by positron emission tomography (PET).

The invention also provides an in vitro method of imaging a cell sample or a tissue sample, comprising contacting the cell sample or tissue sample with a compound which is a compound of formula (Ta), for instance $[^{18}F]$olaparib, or a pharmaceutically acceptable salt thereof, and imaging the cell sample or tissue sample by positron emission tomography (PET).

The method of imaging a subject or the in vitro method of imaging a cell sample or a tissue sample, may further comprise: measuring the distribution of the compound in the subject (for instance the distribution between normal tissue and tumour, or otherwise diseased, tissue in the subject), or in the cell sample or tissue sample; measuring the accumulation of the compound at a site of cancer in the subject, cell sample or tissue sample; measuring the uptake or binding (for instance the PARP-binding) of the compound in the subject, cell sample or tissue sample, or at a site of cancer in the subject, cell sample or tissue sample; detecting the cellular effects or cellular response (for instance DNA damage) following a genotoxic cancer treatment of the subject (such as radiotherapy, external beam irradiation, or chemotherapy); imaging a tumour in the subject, for instance a hypoxic tumour; monitoring radiation damage in the subject, cell sample or tissue sample; or evaluating the ability of a candidate PARP inhibitor to bind to PARP. Such methods may further comprise performing, based on the imaging, patient selection, outcome prediction, or dose optimisation, for example optimisation of the dose of a PARP inhibitor, for instance olaparib dose optimisation.

The invention further provides a method of evaluating the suitability of a PARP inhibitor for treating cancer in a subject, which method comprises:

(a) administering to a subject that has cancer a compound which is a compound of formula (Ta), for instance [$^{18}$F]olaparib, or a pharmaceutically acceptable salt thereof;
(b) detecting the compound by imaging the subject by PET imaging; and
(c) determining from the imaging the suitability of the PARP inhibitor for treating the cancer in the subject. The PARP inhibitor may be olaparib, rucaparib or talazoparib. The PARP inhibitor may be olaparib.

The invention also provides a method of evaluating the effect of a genotoxic cancer treatment, which method comprises:

administering to a subject that has cancer a compound which is a compound of formula (Ia), for instance [$^{18}$F]olaparib, or a pharmaceutically acceptable salt thereof;
detecting the compound by imaging the subject by PET imaging;
performing a genotoxic cancer treatment on the subject;
detecting the compound by imaging the subject by PET imaging after performing the genotoxic cancer treatment on the subject; and
evaluating changes in the image of the subject or the detected amount of the compound before and after performing the genotoxic cancer treatment.

The invention further provides a method of evaluating a candidate PARP-targeting agent in a subject, which method comprises:

administering to a subject a compound which is a compound of formula (Ia), for instance [$^{18}$F]olaparib, or a pharmaceutically acceptable salt thereof;
detecting the compound by imaging the subject by PET imaging;
administering to the subject a candidate PARP-targeting agent;
detecting the compound by imaging the subject by PET imaging after administering the candidate PARP-targeting agent; and
evaluating changes in the image of the subject or the detected amount of the compound before and after after administering the candidate PARP-targeting agent.

The invention further provides a method of diagnosing cancer in a subject, which method comprises (a) administering to the subject a compound which is a compound of formula (Ta), for instance [$^{18}$F]olaparib, or a pharmaceutically acceptable salt thereof; (b) imaging the subject by PET; and (c) determining from the imaging whether or not the subject has cancer.

The invention also provides a compound which is a compound of formula (Ta), for instance [$^{18}$F]olaparib, or a pharmaceutically acceptable salt thereof, for use in a method of diagnosing cancer in a subject, which method comprises (a) administering to the subject a compound which is a compound of formula (Ta), for instance [$^{18}$F]olaparib, or a pharmaceutically acceptable salt thereof; (b) imaging the subject by PET; and (c) determining from the imaging whether or not the subject has cancer.

The invention further provides an in vitro method of diagnosing cancer in a subject, which method comprises (a) contacting a cell sample or a tissue sample previously obtained from the subject with a compound which is a compound of formula (Ia), for instance [$^{18}$F]olaparib, or a pharmaceutically acceptable salt thereof; (b) imaging the cell sample or the tissue sample by PET; and (c) determining from the imaging whether or not the subject has cancer.

The invention further provides a compound which is a compound of formula (Ia), for instance [$^{18}$F]olaparib, or a pharmaceutically acceptable salt thereof, for use in a method for treatment of the human or animal body by surgery or therapy or in a diagnostic method practised on the human or animal body.

The invention additionally provides a method of imaging a subject, comprising administering to the subject a compound of formula (Ta) as defined above or a pharmaceutically acceptable salt thereof, and imaging the subject. The subject may be imaged by positron emission tomography (PET), or single-photon emission computed tomography (SPECT), as appropriate. Often, PET is employed. The method may be as further defined herein for the methods of imaging a subject using [$^{18}$F]olaparib.

BRIEF DESCRIPTION OF THE FIGURES

FIG. 1A provides an overview of (a) olaparib itself and the olaparib-based radiolabelled PARP imaging agents (b) [$^{18}$F]PARPi, (c) [$^{11}$C]olaparib, and (d) [$^{18}$F]olaparib.

FIG. 1B provides an overview of the olaparib-based radiolabelled PARP imaging agents (e) [$^{18}$F]PARPi-FL, (f) [$^{18}$F]BO, (g) [$^{123}$I]PARPi and [$^{131}$I]PARPi and (h) [$^{211}$At]PARPi.

FIG. 3 is reaction scheme showing synthesis of the protected organoboron precursor compound 4-(3-(4-(cyclopropanecarbonyl)piperazine-1-carbonyl)-4-(4,4,5,5-tetra methyl-1,3,2-dioxaborolan-2-yl)benzyl)-2-((2-trimethlsilyl) ethoxy)methyl)phthalazin-1(2H)-one. *2-bromo-5-formylbenzonitrile was synthesised over two steps from 2-amino-5-bromobenzo-nitrile via formylation/Sandmeyer (46% over two steps), **N-(cyclopropylcarbonyl)piperazine.

FIG. 8 shows the sample HPLC radio-trace (top) and the sample HPLC UV-trace (middle) for purified [$^{18}$F]olaparib injected onto an analytical column. Additionally, a sample spiked with an authentic reference sample of olaparib (0.7 μg) was analysed and the bottom trace is the HPLC UV-trace with the spiked authentic reference. Analytical HPLC conditions are as for FIG. 4.

FIG. 12 shows: (A) a schematic of the experimental design of imaging experiments. (B) Biodistribution in mice bearing PANC-1 xenografts, at 1 h post injection of [$^{18}$F] olaparib (3 MBq). (C) Representative MIP images of PANC-1 xenograft-bearing mice, 1 h post injection of [$^{18}$F] olaparib. Arrowheads indicate the position of the xenograft tumour. Insets represent autoradiograms of tumour sections, corroborating PET imaging results. (D) Western Blot showed increased PARP-1 levels in three irradiated compared to three non-irradiated PANC1-xenografts.

FIG. 21 presents graphs showing the ex vivo biodistribution of $^{18}$F-olaparib in CaNT tumour-bearing mice, 1 h after intravenous injection.

FIG. 26 shows a graph (a) of $^{18}$F-olaparib cellular uptake in terms of % cellular fraction (normalised) (y axis) versus the log of the concentration of olaparib (M) (x axis), for both U251MG and U87MG cells; and a graph (b) showing the $^{18}$F-olaparib uptake in terms of % cellular fraction (normalised) (y axis) for 1 μM $^{18}$F-olaparib alone (black) and 1 μM $^{18}$F-olaparib in the presence of 100 μM cold olaparib (grey), for both U251MG and U87MG cells.

FIG. 28(*b*) shows $^{18}$F-olaparib uptake in U251MG and U87MG Xenograft tumours in terms of the percent injected dose of $^{18}$F-olaparib per gram of tumour (% ID/g), after administration of 1 μg $^{18}$F-olaparib alone, or after administration of 1 μg $^{18}$F-olaparib following 20 μg cold olaparib.

DETAILED DESCRIPTION OF THE INVENTION

Definitions

Figure 2:
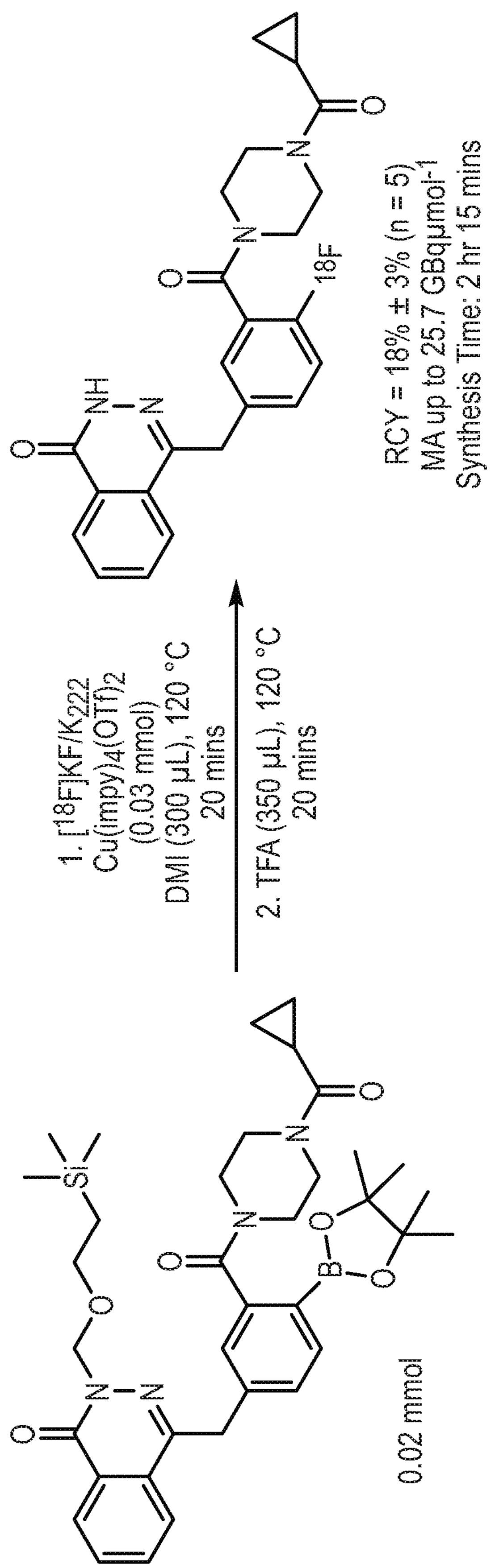
FIG. 2 is a scheme showing an embodiment of the process of the present invention for producing [$^{18}$F]olaparib via copper-mediated $^{18}$F-fluorodeboronation of a protected organoboron precursor compound.
Figure 4:
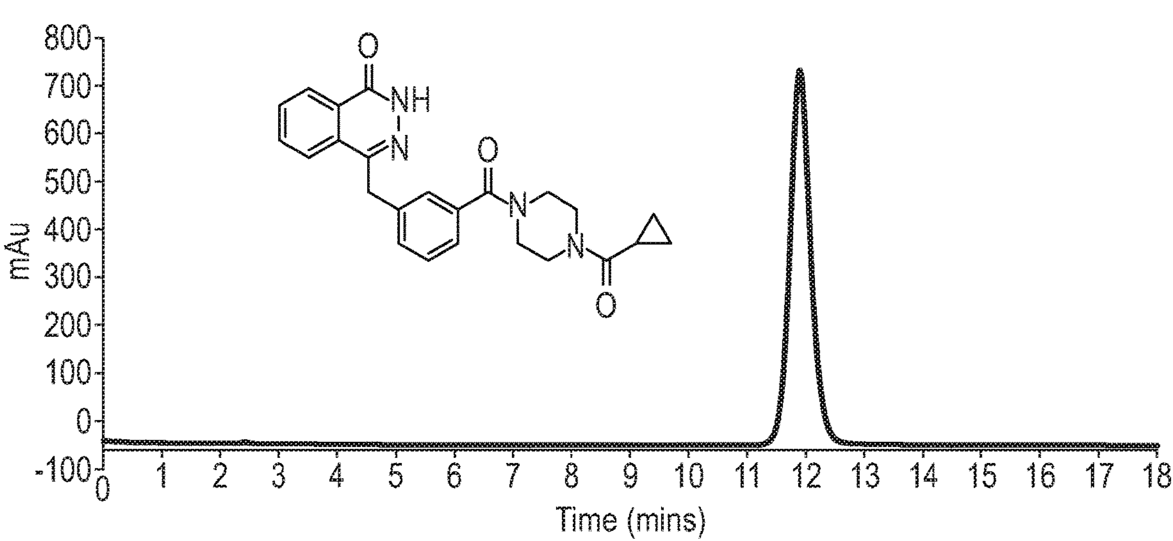
FIG. 4 is an HPLC UV Trace of 4-(3-(4-(cyclopropanecabonyl)piperazine-1-carbnonyl)benzyl)phthalazin-1(2H)-one. HPLC Eluent: Synergi 4 μm Hydro-RP 80A, 150×4.6 mm with 25% MeCN/75% $H_2O$ (isocratic 1 mL/min) monitoring with UV (220 nm).
Figure 5:
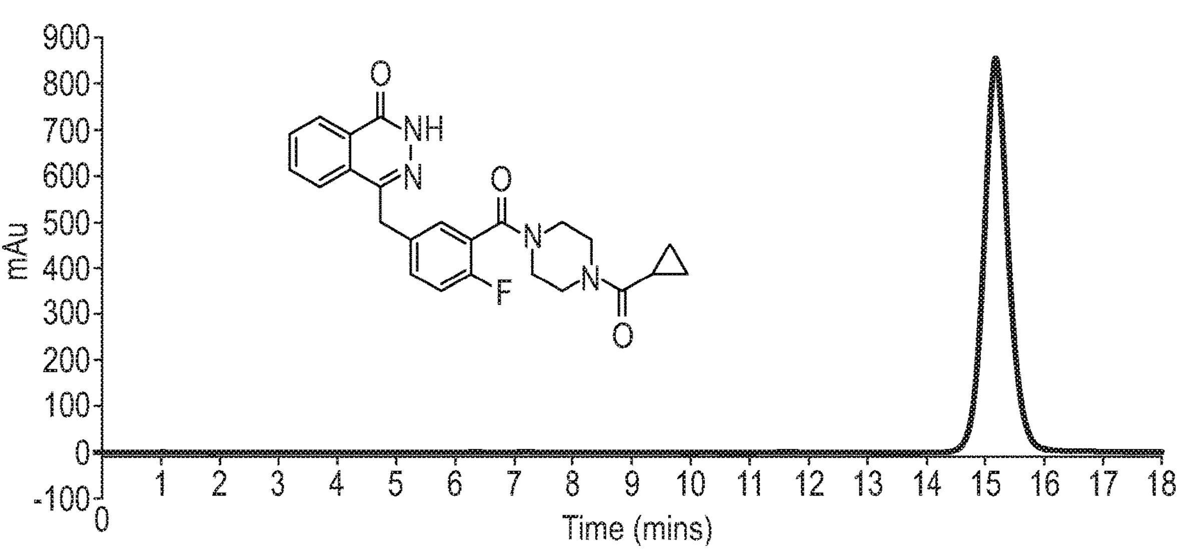
FIG. 5 is an HPLC UV Trace of Olaparib. HPLC conditions as for FIG. 4.
Figure 6:
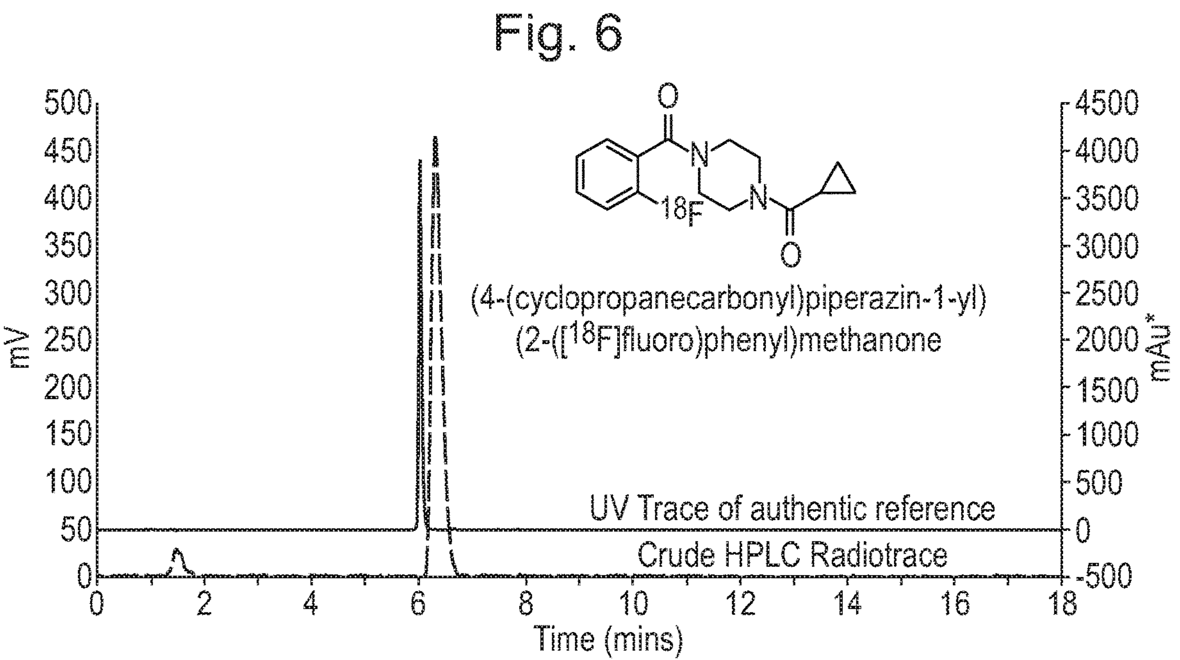
FIG. 6 shows a UV Trace and Radiotrace of (4-(Cyclopropanecarbonyl)piperazin-1-yl)(2-fluorophenyl)methanone.

The term "organoboron compound", as used herein, refers to an organic compound which comprises a C—B bond. The term "organic compound", as used herein, takes its normal meaning in the art.

The term "alkyl group", as used herein, refers to an substituted or unsubstituted, straight or branched chain saturated hydrocarbon radical. Typically an alkyl group is $C_{1-20}$ alkyl, or $C_{1-10}$ alkyl, for example methyl, ethyl, propyl, butyl, pentyl, hexyl, heptyl, octyl, nonyl or decyl (including straight or branched chain isomers thereof), or $C_{1-6}$ alkyl, for example methyl, ethyl, propyl, butyl, pentyl or hexyl (including straight or branched chain isomers thereof), or $C_{1-4}$ alkyl, for example methyl, ethyl, i-propyl, n-propyl, t-butyl, s-butyl or n-butyl. When an alkyl group is substituted it typically bears one or more substituents selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. Examples of substituted alkyl groups include haloalkyl, hydroxyalkyl, aminoalkyl, alkoxyalkyl and alkaryl groups. The term alkaryl, as used herein, pertains to a $C_{1-20}$ alkyl group in which at least one hydrogen atom has been replaced with an aryl group. Examples of such groups include, but are not limited to, benzyl (phenylmethyl, $PhCH_2$—), benzhydryl ($Ph_2CH$—), trityl (triphenylmethyl, $Ph_3C$—), and phenethyl (phenylethyl, Ph-$CH_2CH_2$—). Typically a substituted alkyl group carries 1, 2 or 3 substituents, for instance 1 or 2.

The term "perfluoroalkyl", as used herein, refers to a group which is a straight or branched chain saturated perfluorinated hydrocarbon radical. For example, a perfluoroalkyl group may be have from a to 12 carbon atoms. "Perfluorinated" in this context means completely fluorinated such that there are no carbon-bonded hydrogen atoms replaceable with fluorine. Examples of $C_{4-12}$ perfluoro alkyl groups are trifluoromethyl ($C_1$), pentafluoroethyl ($C_2$), heptafluoropropyl ($C_3$), perfluorobutyl ($C_4$) (for instance including perfluoro-n-butyl, perfluoro-sec-butyl and perfluoro-tert-butyl), perfluoropentyl ($C_5$), perfluorohexyl ($C_6$), perfluoroheptyl ($C_7$), perfluorooctyl ($C_8$), perfluorononyl ($C_9$), perfluorodecyl ($C_{10}$), perfluoroundecyl ($C_{11}$) and perfluorododecyl ($C_{12}$), including straight chained and branched isomers thereof.

The term "alkenyl", as used herein, refers to a linear or branched chain hydrocarbon radical comprising one or more double bonds. An alkenyl group may be a $C_{2-20}$ alkenyl group, a $C_{2-10}$ alkenyl group or a $C_{2-6}$ alkenyl group. Examples of $C_{2-20}$ alkenyl groups include those related to $C_{2-20}$ alkyl groups by the insertion of one or more double bonds. Alkenyl groups typically comprise one or two double bonds. The alkenyl groups referred to herein may be substituted or unsubstituted, as defined for alkyl groups above. The term "alkynyl", as used herein, refers to a linear or branched chain hydrocarbon radical comprising one or more triple bonds. An alkynyl group may be a $C_{2-20}$ alkynyl group, a $C_{2-10}$ alkynyl group a $C_{2-6}$ alkynyl group. Examples of $C_{2-20}$ alkynyl groups include those related to $C_{2-20}$ alkyl groups by the insertion of one or more triple bonds. Alkynyl groups typically comprise one or two triple bonds. The alkynyl groups referred to herein may be substituted or unsubstituted, as defined for alkyl groups above.

The term "cycloalkyl group", as used herein, refers to an substituted or unsubstituted alkyl group which is also a cyclyl group; that is, a monovalent moiety obtained by removing a hydrogen atom from an alicyclic ring atom of a carbocyclic ring of a carbocyclic compound. A cycloalkyl group may have from 3 to 25 carbon atoms (unless otherwise specified), including from 3 to 25 ring atoms. Thus, the term "cycloalkyl" includes the sub-classes cycloalkyenyl and cycloalkynyl. Examples of groups of $C_{3-25}$ cycloalkyl groups include $C_{3-20}$ cycloalkyl, $C_{3-15}$ cycloalkyl, $C_{3-10}$ cycloalkyl, and $C_{3-7}$ cycloalkyl. When a $C_{3-25}$ cycloalkyl group is substituted it typically bears one or more substituents selected from substituted or unsubstituted $C_{1-6}$ alkyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, phosphoric acid, phosphate ester, phosphonic acid and phosphonate ester and sulfonyl. Typically a substituted cycloalkyl group carries 1, 2 or 3 substituents, for instance 1 or 2.

Examples of $C_{3-25}$ cycloalkyl groups include, but are not limited to, those derived from saturated monocyclic hydrocarbon compounds, which $C_{3-25}$ cycloalkyl groups are substituted or unsubstituted as defined above: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$); unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$); saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$); unsaturated polycyclic hydrocarbon compounds: camphene ($C_{10}$), limonene ($C_{10}$), pinene ($C_{10}$); polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

The term "heterocyclyl group", as used herein, refers to an substituted or unsubstituted monovalent moiety obtained by removing a hydrogen atom from a ring atom of a heterocyclic compound, which moiety has from 3 to 20 ring atoms (unless otherwise specified), of which from 1 to 10 are ring heteroatoms. Heterocyclic compounds include aromatic heterocyclic compounds and non-aromatic heterocyclic compounds. Preferably, each ring has from 3 to 7 ring atoms, of which from 1 to 4 are ring heteroatoms. When a $C_{3-20}$ heterocyclyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, phosphoric acid, phosphate ester, phosphonic acid and phosphonate ester and sulfonyl. Typically a substituted $C_{3-20}$ heterocyclyl group carries 1, 2 or 3 substituents, for instance 1 or 2.

Examples of groups of heterocyclyl groups include $C_{3-20}$ heterocyclyl, $C_{5-20}$ heterocyclyl, $C_{3-15}$ heterocyclyl, $C_{5-15}$ is heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of (non-aromatic) monocyclic $C_{3-20}$ heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of $C_{3-20}$ heterocyclyl groups which are also aryl groups are described below as heteroaryl groups.

The term "aryl group", as used herein, refers to a substituted or unsubstituted, monocyclic or polycyclic (for instance bicyclic) aromatic group which typically contains from 6 to 14 carbon atoms, preferably from 6 to 10 carbon atoms in the ring portion. Examples include phenyl, naphthyl, indenyl, indanyl, anthracenyl and pyrenyl groups. An aryl group is substituted or unsubstituted. When an aryl group is substituted it typically bears one or more substituents selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. Typically it carries 0, 1, 2 or 3 substituents. A substituted aryl group may be substituted in two positions with a single $C_{1-6}$ alkylene group, or with a bidentate group represented by the formula —X—$C_{1-6}$ alkylene, or —X—$C_{1-6}$ alkylene-X—, wherein X is selected from O, S and NR, and wherein R is H, aryl or $C_{1-6}$ alkyl. Thus a substituted aryl group may be an aryl group fused with a cycloalkyl group or with a heterocyclyl group. The term "aralkyl" as used herein, pertains to an aryl group in which at least one hydrogen atom (e.g., 1, 2, 3) has been substituted with a $C_{1-6}$ alkyl group. Examples of such groups include, but are not limited to, tolyl (from toluene), xylyl (from xylene), mesityl (from mesitylene), and cumenyl (or cumyl, from cumene), and duryl (from durene).

The ring atoms of an aryl group may include one or more heteroatoms (as in a heteroaryl group). Such an aryl group is a heteroaryl group, and is a substituted or unsubstituted monocyclic or polycyclic (for instance bicyclic) heteroaromatic group which typically contains from 6 to 14 atoms, for instance 6 to 10 atoms, in the ring portion including one or more heteroatoms. It is generally a 5- or 6-membered ring, containing at least one heteroatom selected from O, S, N, P, Se and Si. It may contain, for example, 1, 2 or 3 heteroatoms. Examples of heteroaryl groups include pyridyl, pyrazinyl, pyrimidinyl, pyridazinyl, furanyl, thienyl, pyrazolidinyl, pyrrolyl, oxazolyl, oxadiazolyl, isoxazolyl, thiadiazolyl, thiazolyl, isothiazolyl, imidazolyl, pyrazolyl, quinolyl and isoquinolyl. A heteroaryl group may be substituted or unsubstituted, for instance, as specified above for aryl.

Typically it carries 0, 1, 2 or 3 substituents.

The term "alkylene group" as used herein, refers to an substituted or unsubstituted bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below. Typically it is $C_{1-10}$ alkylene, for instance $C_{1-6}$ alkylene. Typically it is $C_{1-4}$ alkylene, for example methylene, ethylene, i-propylene, n-propylene, t-butylene, s-butylene or n-butylene. It may also be pentylene, hexylene, heptylene, octylene and the various branched chain isomers thereof. An alkylene group may be substituted or unsubstituted, for instance, as specified above for alkyl. Typically a substituted alkylene group carries 1, 2 or 3 substituents, for instance 1 or 2.

In this context, the prefixes (e.g., $C_{1-4}$, $C_{1-7}$, $C_{1-20}$, $C_2$-7, $C_3$-7, etc.) denote the number of carbon atoms, or range of number of carbon atoms. For example, the term "$C_{1-4}$alkylene," as used herein, pertains to an alkylene group having from 1 to 4 carbon atoms. Examples of groups of alkylene groups include $C_{1-4}$ alkylene ("lower alkylene"), $C_{1\_7}$ alkylene, $C_{1-10}$ alkylene and $C_{1-20}$ alkylene.

Examples of linear saturated $C_{1-7}$ alkylene groups include, but are not limited to, $—(CH_2)_n—$ where n is an integer from 1 to 7, for example, $—CH_2—$ (methylene), $—CH_2CH_2—$ (ethylene), $—CH_2CH_2CH_2—$ (propylene), and $—CH_2CH_2CH_2CH_2—$ (butylene).

Examples of branched saturated $C_{1-7}$ alkylene groups include, but are not limited to, $—CH(CH_3)—$, $—CH(CH_3)CH_2—$, $—CH(CH_3)CH_2CH_2—$, $—CH(CH_3)CH_2CH_2CH_2—$, $—CH_2CH(CH_3) CH_2—$, $—CH_2CH(CH_3)CH_2CH_2—$, $—CH(CH_2CH_3)—$, $—CH(CH_2CH_3)CH_2—$, and $—CH_2CH(CH_2CH_3)CH_2—$.

Examples of linear partially unsaturated $C_{1\_7}$ alkylene groups include, but is not limited to, —CH═CH— (vinylene), $—CH═CH—CH_2—$, $—CH_2—CH═CH_2—$, $—CH═CH—CH_2—CH_2—$, $—CH═CH—CH_2—CH_2—CH_2—$, —CH═CH—CH═CH—, $—CH═CH—CH═CH—CH_2—$, $—CH═CH—CH═CH—CH_2—CH_2—$, $—CH═CH—CH_2—CH═CH—$, and $—CH═CH—CH_2—CH_2—CH═CH—$.

Examples of branched partially unsaturated $C_{1-7}$ alkylene groups include, but is not limited to, $—C(CH_3)═CH—$, $—C(CH_3)═CH—CH_2—$, and $—CH═CH—CH(CH_3)—$.

Partially unsaturated alkylene groups comprising one or more double bonds may be referred to as alkenylene groups. Partially unsaturated alkylene groups comprising one or more triple bonds may be referred to as alkynylene groups (for instance —C≡C—, $CH_2—C≡C—$, and $—CH_2—C≡C≡CH_2—$).

Examples of alicyclic saturated $C_{1-7}$ alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

$C_{1-20}$ alkylene and $C_{1-20}$ alkyl groups as defined herein are either uninterrupted or interrupted by one or more heteroatoms or heterogroups, such as S, O or N(R") wherein R" is H, $C_{1-6}$ alkyl or aryl (typically phenyl), or by one or more arylene (typically phenylene) groups, or by one or more —C(O)— or —C(O)N(R")— groups. The phrase "optionally interrupted" as used herein thus refers to a $C_{1-20}$ alkyl group or an alkylene group, as defined above, which is uninterrupted or which is interrupted between adjacent carbon atoms by a heteroatom such as oxygen or sulfur, by a heterogroup such as N(R") wherein R" is H, aryl or $C_1$-$C_6$ alkyl, or by an arylene group, or by a —C(O)— or —C(O)N(R")— group, again wherein R" is H, aryl or $C_1$-$C_6$ alkyl.

For instance, a $C_{1-20}$ alkyl group such as n-butyl may be interrupted by the heterogroup N(R") as follows: $—CH_2N(R")CH_2CH_2CH_3$, $—CH_2CH_2N(R")CH_2CH_3$, or $—CH_2CH_2CH_2N(R")CH_3$. Similarly, an alkylene group such as n-butylene may be interrupted by the heterogroup N(R") as follows: $—CH_2N(R")CH_2CH_2CH_2—$, $—CH_2CH_2N(R")CH_2CH_2—$, or $—CH_2CH_2CH_2N(R")CH_2—$. Typically an interrupted group, for instance an interrupted $C_{1-20}$ alkylene or $C_{1-20}$ alkyl group, is interrupted by 1, 2 or 3 heteroatoms or heterogroups or by 1, 2 or 3 arylene (typically phenylene) groups. More typically, an interrupted group, for instance an interrupted $C_{1-20}$ alkylene or $C_{1-20}$ alkyl group, is interrupted by 1 or 2 heteroatoms or heterogroups or by 1 or 2 arylene (typically phenylene) groups. For instance, a $C_{1-20}$ alkyl group such as n-butyl may be interrupted by 2 heterogroups N(R") as follows: $—CH_2N(R")CH_2N(R")CH_2CH_3$.

An arylene group is an substituted or unsubstituted bidentate moiety obtained by removing two hydrogen atoms, one from each of two different aromatic ring atoms of an aromatic compound, which moiety has from 5 to 14 ring atoms (unless otherwise specified).

Typically, each ring has from 5 to 7 or from 5 to 6 ring atoms. An arylene group may be substituted or unsubstituted, for instance, as specified above for aryl.

In this context, the prefixes (e.g., $C_5$-20, $C_{6-20}$, $C_{5-14}$, $C_{5-7}$, $C_5$-6, etc.) denote the number of ring atoms, or range of number of ring atoms, whether carbon atoms or heteroatoms. For example, the term "$C_{5-6}$ arylene," as used herein, pertains to an arylene group having 5 or 6 ring atoms. Examples of groups of arylene groups include $C_{5-20}$ arylene, $C_{6-20}$ arylene, $C_{5-14}$ arylene, $C_{6-14}$ arylene, $C_{6-10}$ arylene, $C_{5-12}$ arylene, $C_{5-10}$ arylene, $C_{5-7}$ arylene, $C_{5-6}$ arylene, $C_5$ arylene, and $C_6$ arylene.

The ring atoms may be all carbon atoms, as in "carboarylene groups" (e.g., $C_{6-20}$ carboarylene, $C_{6-14}$ carboarylene or $C_{6-10}$ carboarylene).

Examples of $C_{6-20}$ arylene groups which do not have ring heteroatoms (i.e., $C_{6-20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., $C_{5-10}$ heteroarylene).

Examples of $C_{5-10}$ heteroarylene groups include, but are not limited to, those derived from the compounds discussed above in regard to heteroaryl groups.

As used herein the term "oxo" represents a group of formula: =O

As used herein the term "acyl" represents a group of formula: —C(=O)R, wherein R is an acyl substituent, for example, a substituted or unsubstituted $C_{1-20}$ alkyl group, substituted or unsubstituted $C_{2-20}$ alkenyl group, substituted or unsubstituted $C_{2-20}$ alkynyl group, a substituted or unsubstituted $C_{3-20}$ heterocyclyl group, a substituted or unsubstituted aryl group or a substituted or unsubstituted heteroaryl group, for instance a substituted or unsubstituted $C_{1-6}$ alkyl group. Examples of acyl groups include, but are not limited to, $—C(=O)CH_3$ (acetyl), $—C(=O)CH_2CH_3$ (propionyl), $—C(=O)C(CH_3)_3$ (t-butyryl), and —C(=O)Ph (benzoyl, phenone).

As used herein the term "acyloxy" (or reverse ester) represents a group of formula: —OC(=O)R, wherein R is an acyloxy substituent, for example, a substituted or unsubstituted $C_{1-20}$ alkyl group, substituted or unsubstituted $C_{2-20}$ alkenyl group, substituted or unsubstituted $C_{2-20}$ alkynyl group, a substituted or unsubstituted $C_{3-20}$ heterocyclyl group, a substituted or unsubstituted aryl group or a substituted or unsubstituted heteroaryl group, for instance a substituted or unsubstituted $C_{1-6}$ alkyl group. Examples of acyloxy groups include, but are not limited to, $—OC(=O)CH_3$ (acetoxy), $—OC(=O)CH_2CH_3$, $—OC(=O)C(CH_3)_3$, —OC(=O)Ph, and $—OC(=O)CH_2Ph$.

As used herein the term "ester" (or carboxylate, carboxylic acid ester or oxycarbonyl) represents a group of formula: —C(=O)OR, wherein R is an ester substituent, for example, a substituted or unsubstituted $C_{1-20}$ alkyl group, substituted or unsubstituted $C_{2-20}$ alkenyl group, substituted or unsubstituted $C_{2-20}$ alkynyl group, a substituted or unsubstituted $C_{3-20}$ heterocyclyl group, a substituted or unsubstituted aryl group or a substituted or unsubstituted heteroaryl group, for instance a substituted or unsubstituted $C_{1-6}$ alkyl group. Examples of ester groups include, but are not limited to, $C(=O)OCH_3$, $C(=O)OCH_2CH_3$, $C(=O)OC(CH_3)_3$, and C(=O)OPh.

As used herein the term "amino" represents a group of formula $—NH_2$. The term "$C_1$-$C_{10}$ alkylamino" represents a group of formula —NHR' wherein R' is a $C_{1-10}$ alkyl group, preferably a $C_{1-6}$ alkyl group, as defined previously. The term "di($C_{1-10}$)alkylamino" represents a group of formula —NR'R" wherein R' and R" are the same or different and represent $C_{1-10}$ alkyl groups, preferably $C_{1-6}$ alkyl groups, as defined previously. The term "arylamino" represents a group of formula —NHR' wherein R' is an aryl group, preferably a phenyl group, as defined previously. The term "diarylamino" represents a group of formula —NR'R" wherein R' and R" are the same or different and represent aryl groups, preferably phenyl groups, as defined previously. The term "arylalkylamino" represents a group of formula —NR'R" wherein R' is a $C_{1-10}$ alkyl group, preferably a $C_{1-6}$ alkyl group, and R" is an aryl group, preferably a phenyl group.

A halo group is chlorine, fluorine, bromine or iodine (a chloro group, a fluoro group, a bromo group or an iodo group). It is typically chlorine, fluorine or bromine.

As used herein the term "amido" represents a group of formula: —C(=O)NR'R", wherein R' and R" are independently amino substituents, as defined for di($C_{1-10}$)alkylamino groups.

Examples of amido groups include, but are not limited to, $—C(=O)NH_2$, $—C(=O)NHCH_3$, $—C(=O)N(CH_3)_2$, $—C(=O)NHCH_2CH_3$, and $—C(=O)N(CH_2CH_3)_2$, as well as amido groups in which R' and R", together with the nitrogen atom to which they are attached, form a heterocyclic structure as in, for example, piperidinocarbonyl, morpholinocarbonyl, thiomorpholinocarbonyl, and piperazinocarbonyl. As used herein the term "acylamido" represents a group of formula: —$NR^1C$(=O)$R^2$, wherein $R^1$ is an amide substituent, for example, hydrogen, a $C_{1-20}$ alkyl group, a $C_{3-20}$ heterocyclyl group, an aryl group, preferably hydrogen or a $C_{1-20}$ alkyl group, and $R^2$ is an acyl substituent, for example, a $C_{1-20}$ alkyl group, a $C_{3-20}$ heterocyclyl group, or an aryl group, preferably hydrogen or a $C_{1-20}$ alkyl group. Examples of acylamide groups include, but are not limited to, —NHC(=O)$CH_3$, —NHC(=O)$CH_2CH_3$, —NHC(=O)Ph, —NHC(=O)$C_{15}H_{31}$ and —NHC(=O)$C_9H_{19}$. Thus, a substituted $C_{1-20}$ alkyl group may comprise an acylamido substituent defined by the formula —NHC(=O)—$C_{1-20}$ alkyl, such as —NHC(=O)$C_{15}H_{31}$ or —NHC(=O)$C_9H_{19}$. $R^1$ and $R^2$ may together form a cyclic structure, as in, for example, succinimidyl, maleimidyl, and phthalimidyl:

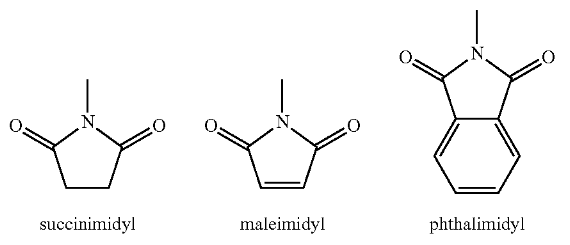

succinimidyl maleimidyl phthalimidyl

A $C_{1-10}$ alkylthio group is a said $C_{1-10}$ alkyl group, preferably a $C_{1-6}$ alkyl group, attached to a thio group. An arylthio group is an aryl group, preferably a phenyl group, attached to a thio group.

A $C_{1-20}$ alkoxy group is a said substituted or unsubstituted $C_{1-20}$ alkyl group attached to an oxygen atom. A $C_{1-6}$ alkoxy group is a said substituted or unsubstituted $C_{1-6}$ alkyl group attached to an oxygen atom. A $C_{1-4}$ alkoxy group is a substituted or unsubstituted $C_{1-4}$ alkyl group attached to an oxygen atom. Said $C_{1-20}$, $C_{1-6}$ and $C_{1-4}$ alkyl groups are optionally interrupted as defined herein. Examples of $C_{1-4}$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). Further examples of $C_{1-20}$ alkoxy groups are —O(Adamantyl), —O—$CH_2$-Adamantyl and —O—$CH_2$—$CH_2$-Adamantyl. An aryloxy group is a substituted or unsubstituted aryl group, as defined herein, attached to an oxygen atom. An example of an aryloxy group is —OPh (phenoxy).

Unless otherwise specified, included in the above are the well known ionic, salt, solvate, and protected forms of these substituents. For example, a reference to carboxylic acid or carboxyl group (—COOH) also includes the anionic (carboxylate) form (—COO'), a salt or solvate thereof, as well as conventional protected forms. Similarly, a reference to an amino group includes the protonated form (—N+$HR^1R^2$), a salt or solvate of the amino group, for example, a hydrochloride salt, as well as conventional protected forms of an amino group. Similarly, a reference to a hydroxyl group also includes the anionic form (—O'), a salt or solvate thereof, as well as conventional protected forms.

Certain compounds may exist in one or more particular geometric, optical, enantiomeric, diastereomeric, epimeric, atropic, stereoisomeric, tautomeric, conformational, or anomeric forms, including but not limited to, cis- and trans-forms; $E^-$ and Z-forms; c-, t-, and r- forms; endo- and exo-forms; R-, S-, and meso-forms; D- and L-forms; d- and 1-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto, enol, and enolate forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

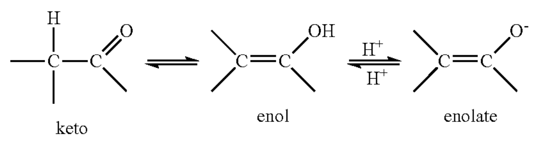

keto enol enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like, unless otherwise specified. However, reference to an isotope of fluorine refers only to that isotope of fluorine. In particular, reference to $^{18}F$ includes only $^{18}F$. Reference to fluorine without specifying the isotope may refer to $^{18}F$ or $^{19}F$ depending on context. Typically, reference to "F" (i.e. without defining the isotope) refers to the $^{19}F$, i.e. stable fluorine.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting known methods, in a known manner.

The term "substituted", as used herein, may be as defined above for particular groups. However, in some instances, the term substituted may refer to a group substituted with a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. In other instances, the term "substituted" may refer to a group substituted with a group selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted heteroaryl, cyano, amino, $C_{1-6}$ alkylamino, di($C_{1\_6}$)alkylamino, arylamino, diarylamino, arylalkylamino, amido, acylamido, hydroxy, oxo, halo, carboxy, ester, acyl, acyloxy, $C_{1-6}$ alkoxy, aryloxy, haloalkyl, sulfonic acid, thiol, $C_{1-6}$ alkylthio, arylthio, sulfonyl, phosphoric acid, phosphate ester, phosphonic acid and phosphonate ester. For example, the term "substituted" may refer to a group substituted with a group selected unsubstituted $C_{1-6}$ alkyl, unsubstituted $C_{2-6}$ alkenyl, unsubstituted $C_{2-6}$ alkynyl, unsubstituted aryl, unsubstituted heteroaryl, cyano, amino, unsubstituted $C_{1-6}$ alkylamino, unsubstituted di($C_{1-6}$)alkylamino, unsubstituted arylamino, unsubstituted diarylamino, unsubstituted arylalkylamino, unsubstituted amido, unsubstituted acylamido, hydroxy, oxo, halo, carboxy, unsubstituted ester, unsubstituted acyl, unsubstituted acyloxy, unsubstituted $C_{1-6}$ alkoxy, unsubstituted aryloxy, sulfonic acid, thiol, unsubstituted $C_{1-6}$ alkylthio, unsubstituted arylthio, sulfonyl, phosphoric acid, unsubstituted phosphate ester, unsubstituted phosphonic acid and unsubstituted phosphonate ester.

The term "$^{18}F$" refers to an atom of the specific isotope of fluorine having 9 protons and 9 neutrons. The term "$^{18}F^-$" refers to an anion of the atom of the specific isotope of fluorine having 9 protons and 9 neutrons.

The term "boronic ester group", as used herein, refers to a group of formula —$B(OR)_2$ wherein R is H or an organic group, for instance a substituted or unsubstituted alkyl group. The term "boronic acid group", as used herein, refers to a group of formula —$B(OH)_2$. The term "boronate group", as used herein, refers to a group of formula —$B(OR)_3^-$ wherein R is H or an organic group, for instance a substituted or unsubstituted alkyl group. As boronate groups are negatively charged, a cation is typically present, for instance a metal cation such as $Na^+$ or $K^+$. The term "trifluoroborate group", as used herein, refers to a group of formula —$BF_3^-$. As trifluoroborate groups are negatively charged, a cation is typically present, for instance a metal cation such as $Na^+$ or $K^+$.

The term "ligand", as used herein, refers to a species capable of binding to a central atom (in this case a copper atom or ion) to form a complex. Ligands may be charged or neutral species. Typically, as referred to herein, a ligand is a neutral species.

The term "halide", as used herein, refers to fluoride, chloride, bromide, iodide and astatide. Typically, a halide is fluoride, chloride, bromide or iodide.

The term "protecting group", as used herein, takes its normal meaning in the art. Thus, a protecting group is a group which is introduced into a compound so that a subsequent step is chemoselective and does not affect the protected group. Protecting groups may be categorised as those suitable for protecting specific functional groups. Thus a protecting group may, for instance, be an alcohol protecting group, an amine protecting group or a carboxylic acid protecting group.

The detailed discussion below relating to features of the process of the invention for producing a compound of formula (I) applies equally to the above-defined process for producing a compound of formula (Ia). Thus, unless it is otherwise apparent from the context, the preferences outlined below for the process of the invention for producing a compound of formula (I) apply also to the above-defined process for producing a compound of formula (Ia).

Process

The invention provides a process for producing a compound of formula (I)

(I)

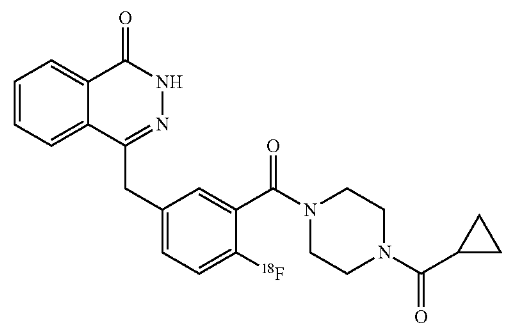

which process comprises:

(i) treating an organoboron compound of formula (II) with $^{18}F^-$ and a copper compound:

(II)

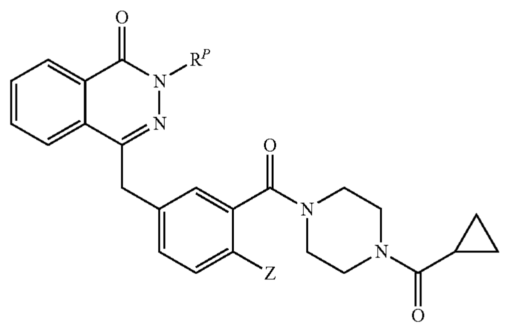

wherein

Z is a boronic ester group, a boronic acid group, a boronate group or a trifluoroborate group; and $R^P$ is a protecting group of formula (III)

(III)

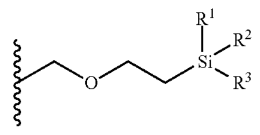

wherein $R^1$ is $C_{1-6}$ alkyl;

$R^2$ is $C_{1-6}$ alkyl; and $R^3$ is $C_{1-6}$ alkyl;

and (ii) removing the protecting group $R^P$ to produce the compound of formula (I).

Typically the organoboron compound of formula (II) is treated with both $^{18}F^-$ and the copper compound simultaneously. Thus, typically the process comprises treating the organoboron compound with $^{18}F^-$ in the presence of the copper compound. Equivalently, the process may comprise treating the organoboron compound with the copper compound in the presence of $^{18}F^-$. $^{18}F^-$ may refer to any suitable source of $18F^-$, as discussed below. Often $^{18}F$ will be solvated.

Copper Compound

Any suitable copper compound may be used in the process of the invention. The copper compound is often a copper salt. The copper salt may be a copper (I) salt, a copper (II) salt, or a copper (III) salt. Preferably, the copper compound is a copper (II) salt or a copper (III) salt. More preferably, the copper compound is a copper (II) salt. The copper compound may be a simple salt comprising $Cu^{n+}$ (n=1, 2, or 3) and one or more anions or may be a salt comprising a complex copper cation and one or more cations. Thus, the copper compound may be a copper salt comprising one or more X groups, wherein each X group is the same or different and is an anion. For instance, the copper compound may be a salt of formula $CuX_2$, where X is an anion and the salt may further comprise one or more neutral ligands.

In one embodiment, the copper compound comprises a compound of formula $[L_nCuX_m]$, wherein: each L is the same or different and is a ligand, optionally wherein two or more L groups are bonded together to form one or more rings; each X is the same or different and is an anion, optionally wherein two or more X groups are bonded together to form one or more rings; n is an integer from 0 to 6; and m is an integer from 0 to 4. Often the copper compound is a compound of formula $[L_nCuX_m]$.

The compound of formula $[L_nCuX_m]$ may be charged or neutral. Thus it may be a complex copper cation. If the compound of formula $[L_nCuX_m]$ is charged, the copper compound may further comprise one or more counterions. For instance, if the compound of formula $[L_nCuX_m]$ is positively charged, the copper compound may further comprise one or more anions. The one or more anions may be selected from any anion described herein. The one or more anions may be selected from halide, hydroxide, sulfate, and nitrate. The copper complex may be cationic or anionic, and associated with one or more counter-ions. The copper compound may for instance be cationic, and associated with one or more counter-anions. The compound of formula $[L_nCuX_m]$ may be a monocation, a dication, or a trication for example. Any suitable counter-anion may be employed; a wide range of suitable counter anions is well known to the skilled person. The counter-anion or -anions may for instance be selected from halide, hydroxide, sulfate, nitrate, hexafluorophosphate, chlorate or tetrafluoroborate anions. Alternatively, the metal complex may be anionic, and associated with one or more counter-cations. Again, any suitable counter-cation may be employed; many such cations are known to the skilled person.

In the formula $[L_nCuX_m]$, the copper atom Cu may be a neutral copper atom or a copper (I), (II) or (III) ion. Often, formula $[L_nCuX_m]$ comprises a Cu(II) ion.

n is often an integer from 0 to 4, for instance 3 or 4. m is typically an integer from 1 to 3, for instance 2.

In the formula $[L_nCuX_m]$, one or more of the L groups is often a ligand comprising one or more N atoms, one or more O atoms or one or more S atoms. Examples of ligands comprising one or more N atoms include ammonia, an alkylamine, a dialkylamine, a trialkylamine, an arylamine, a diarylamine, a triarylamine, an alkylenediamine and a heterocyclic compound comprising one or more N atoms. Alky, aryl, alkylene and heterocyclic groups in ligands comprising one or more N atoms may be as described anywhere herein, and such groups may be unsubstituted. Examples of ligands comprising one or more O atoms include water, an alcohol, a carboxylic acid (including a carboxylate), a dialkylether, an alkylenediol and a heterocyclic compound comprising one or more O atoms. An alcohol ligand may be a compound of formula ROH wherein R is a substituted or unsubstituted alkyl compound as described anywhere herein. A carboxylic acid ligand may be a compound of formula RCOOH or $RCOO^-$ wherein R is a substituted or unsubstituted alkyl group as described anywhere herein. Alkyl, alkylene and heterocyclic groups in ligands comprising one or more O atoms may be as described anywhere herein. Examples of ligands comprising one or more S atoms include $H_2S$, a alkylthiol, a dialkylthio ether and a heterocyclic compound comprising one or more S atoms. Alkyl and heterocyclic groups in ligands comprising one or more S atoms may be as described anywhere herein.

Often, one or more of the L groups is a neutral ligand selected from a heterocyclic compound comprising one or more N atoms, a heterocyclic compound comprising one or more O atoms, a heterocyclic compound comprising one or more S atoms, an amine, and water.

Preferably, one or more of the L groups is a neutral ligand which is a fused bicyclic aromatic heterocyclic compound comprising one or more N atoms, preferably from 1 to 4 N atoms.

Examples of heterocyclic compounds comprising one or more N atoms include aziridine, azetidine, pyrrolidine (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, azepine, imidazolidine, pyrazolidine (diazolidine), imidazoline, pyrazoline (dihydropyrazole), piperazine, tetrahydrooxazole, dihydrooxazole, tetrahydroisoxazole, dihydroisoxazole, morpholine, tetrahydrooxazine, dihydrooxazine, oxazine, thiazoline, thiazolidine, thiomorpholine, oxadiazine, pyridine, pyrazine, pyrimidine, pyridazine, pyrazolidine, pyrrole, oxazole, isoxazole, thiadiazole, thiazolyl, isothiazole, imidazole, pyrazole, quinoline, isoquinoline, oxadiazole, phenanthroline and 2,2'-bipyridyl.

Examples of heterocyclic compounds comprising one or more O atoms include oxirane, oxetane, oxolane (tetrahydrofuran), oxole (dihydrofuran), oxane (tetrahydropyran), dihydropyran, pyran, oxepin, dioxolane, dioxane, dioxepane, trioxane, tetrahydrooxazole, dihydrooxazole, tetrahydroisoxazole, dihydroisoxazole, morpholine, tetrahydrooxazine, dihydrooxazine, oxazine, oxadiazine, oxathiole, oxathiane (thioxane), oxathiazine, a saccharide, furan, oxazole, oxadiazole, and isoxazole.

Examples of heterocyclic compounds comprising one or more S atoms include thiophene, tetrahydrothiophene, thiazole, isothiazole, thiazoline, dithiane, and thiomorpholine. The amine may be ammonia, an alkylamine, a dialkylamine, a trialkylamine, an arylamine, a diarylamine, a triarylamine, or an alkylenediamine.

In one embodiment, one or more of the L groups is a ligand selected from substituted or unsubstituted imidazo[1,2-b]pyridazine, substituted or unsubstituted pyridine, substituted or unsubstituted pyrrole, substituted or unsubstituted pyrrolidine, substituted or unsubstituted imidazole, substituted or unsubstituted imidazoline, substituted or unsubstituted imidazolidine, substituted or unsubstituted pyrazole, substituted or unsubstituted pyrazoline, substituted or unsubstituted pyrazolidine, substituted or unsubstituted pyridazine, substituted or unsubstituted pyrimidine, substituted or unsubstituted pyrazine, substituted or unsubstituted triazine, substituted or unsubstituted oxazole, substituted or unsubstituted isoxazole, substituted or unsubstituted thiazole, and substituted or unsubstituted isothiazole, or wherein two of the L groups are bonded together to form a ligand selected from substituted or unsubstituted $C_{1-6}$ alkylene diamine, substituted or unsubstituted 2,2'-bipyridine, and substituted or unsubstituted phenanthroline. For instance, one or more of the L groups may be a ligand selected from substituted or unsubstituted imidazo[1,2-b]pyridazine, substituted or unsubstituted pyridine, substituted or unsubstituted 2,2'-bipyridine, and substituted or unsubstituted phenanthroline. Often, one or more of the L groups is substituted or substituted pyridine. Preferably, one or more of the L groups is substituted or unsubstituted imidazo[1,2-b]pyridazine.

Often, one or more of the L groups is a ligand of formula (IVa) or (Va)

(IVa)

(Va)

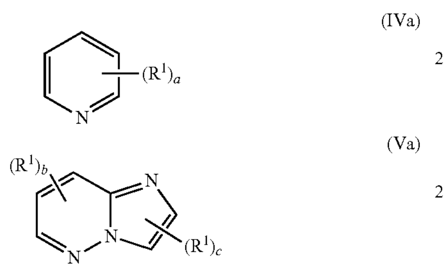

wherein: each $R^1$ is the same or different and is a substituent selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-10}$ alkoxy, aryloxyaloalkyl, sulfonic acid, thiol, $C_{1-10}$ alkylthio, arylthio, sulfonyl, phosphoric acid, phosphate ester, phosphonic acid and phosphonate ester; a is 0 or an integer from 1 to 5; b is 0 or an integer from 1 to 3; and c is 0, 1 or 2.

For example, each $R^1$ may be selected from unsubstituted $C_{1-6}$ alkyl, unsubstituted $C_{2-6}$ alkenyl, unsubstituted $C_{2-6}$ alkynyl, unsubstituted aryl, unsubstituted heteroaryl, cyano, amino, unsubstituted $C_{1-6}$ alkylamino, unsubstituted di($C_{1-6}$)alkylamino, unsubstituted arylamino, unsubstituted diarylamino, unsubstituted arylalkylamino, unsubstituted amido, unsubstituted acylamido, hydroxy, oxo, halo, carboxy, unsubstituted ester, unsubstituted acyl, unsubstituted acyloxy, unsubstituted $C_{1-6}$ alkoxy, unsubstituted aryloxy, sulfonic acid, thiol, unsubstituted $C_{1-6}$ alkylthio, unsubstituted arylthio, sulfonyl, phosphoric acid, unsubstituted phosphate ester, unsubstituted phosphonic acid and unsubstituted phosphonate ester.

Thus, each $R^1$ may be selected from unsubstituted $C_{1-6}$ alkyl. a is often 0, 1 or 2, for instance 0 or 1. b is often 0, 1 or 2, for instance 0 or 1. c is often 0, 1 or 2, for instance 0 or 1.

Often, one or more of the L groups is unsubstituted pyridine. For instance, every L group may be unsubstituted pyridine.

Preferably, however, one or more of the L groups is a ligand of formula (Va). For instance, each L may be a ligand of the formula (Va).

Preferably, one or more of the L groups is unsubstituted imidazo[1,2-b]pyridazine. For instance, every L group may be unsubstituted imidazo[1,2-b]pyridazine.

As described above, the copper compound is often a copper salt comprising one or more anions X.

Often, one or more of the X groups is an anion selected from halide anions and anions of formula $[\text{—OS(O)}_2\text{Y}]^-$, $[\text{—S(O)}_2\text{Y}]^-$, and $[\text{—OC(O)Y}]^-$, wherein Y is a group selected from halide, substituted or unsubstituted $C_{1-10}$ alkyl, substituted or unsubstituted $C_{2-10}$ alkenyl, substituted or unsubstituted $C_{2-10}$ alkynyl, perfluoroalkyl, substituted or unsubstituted $C_{3-10}$ cycloalkyl groups, substituted or unsubstituted aryl groups and substituted or unsubstituted heterocyclyl groups. For instance, Y may be methyl, benzyl, toluenyl, or perfluoroalkyl. Y may be a perfluoroalkyl group selected from trifluoromethyl, pentafluoroethyl, heptafluoropropyl, perfluorobutyl (including perfluoro-n-butyl, perfluoro-sec-butyl and perfluoro-tert-butyl), perfluoropentyl, perfluorohexyl, perfluoroheptyl, perfluorooctyl, perfluorononyl, perfluorodecyl, perfluoroundecyl and perfluorododecyl, including straight chained and branched isomers thereof.

Preferably, one or more of the X groups is an anion selected from triflate (—OTf), triflyl (-Tf), nonaflate, fluorosulfonate, sulfonate, tosyl, mesylate, pivalate, acetate, trifluoroacetate, fluoride, chloride, bromide, iodide, and hydroxide. One or more of the X groups may be an anion selected from triflate (—OTf), triflyl (-Tf), nonaflate, fluorosulfonate, sulfonate, tosyl, mesylate, pivalate, acetate, trifluoroacetate, chloride, bromide, iodide, and hydroxide. For example, one or more of the X groups may be selected from triflate, nonaflate, fluorosulfonate, sulfonate, and tosyl. Preferably, each X is an anion of formula $[\text{—OS(O)}_2\text{Y}]^-$ wherein Y is F or perfluoroalkyl. For instance, each X may be triflate. The copper compound may be a compound of formula $[L_nCu(OTf)_2]$, wherein each L is the same or different and is a ligand, optionally wherein two or more L groups are bonded together to form one or more rings; n is an integer from 0 to 4. L may as defined anywhere herein, for instance substituted or unsubstituted pyridine, or preferably, for instance imidazo[1,2-b]pyridazine (impy). n is often an integer from 2 to 4, for instance 4.

In one embodiment, the copper compound is a compound of formula $[(Py)_4Cu^{II}(OTf)_2]$. Here "Py" represents unsubstituted pyridine.

Preferably, the copper compound is a compound of formula $[(impy)_4Cu^{II}(OTf)_2]$. Here, "impy" represents unsubstituted imidazo[1,2-b]pyridazine.

The $[(impy)_4Cu^{II}(OTf)_2]$ may be formed in situ from impy and a compound of formula $[L_nCu(OTf)_2]$, wherein n is an integer from 0 to 4 and each L is a ligand as defined anywhere herein other than impy. Thus, treating the organoboron compound of formula (II) with the copper compound may comprise treating the organoboron compound with impy and a compound of formula $[L_nCu(OTf)_2]$, wherein n is an integer from 0 to 4 and each L is a ligand as defined anywhere herein other than impy.

For instance, the $[(impy)_4Cu^{II}(OTf)_2]$ may be formed in situ from impy and a compound of formula $[L_nCu(OTf)_2]$, wherein n is an integer from 0 to 4 and each L is a ligand of formula (IVa) as defined herein. Thus, treating the organoboron compound of formula (II) with the copper compound may comprise treating the organoboron compound with impy and a compound of formula $[L_nCu(OTf)_2]$, wherein n is an integer from 0 to 4 and each L is a ligand of formula (IVa) as defined herein.

The $[(impy)_4Cu^{II}(OTf)_2]$ may for instance be formed in situ from impy and $[(Py)_4Cu^{II}(OTf)_2]$. Thus, treating the organoboron compound of formula (II) with the copper compound may comprise treating the organoboron compound with impy and $[(Py)_4Cu^{II}(OTf)_2]$.

Preferably, however, the $[(impy)_4Cu^{II}(OTf)_2]$ is not formed in situ. Thus, usually, treating the organoboron compound of formula (II) with the copper compound comprises treating the organoboron compound with $[(impy)_4Cu^{II}(OTf)_2]$.

Organoboron Compound

The organoboron compound treated in the process of the invention is a compound of formula (II) as defined above wherein Z is a boronic ester group, a boronic acid group, a boronate group or a trifluoroborate group, and $R^P$ is a protecting group of formula (III) as defined above.

The boronic ester group, boronic acid group, boronate group or trifluoroborate group, Z, usually contains only one boron atom. Z is typically a boronic ester group. The boron atom of the group Z is bonded to the carbon atom in the phenyl ring to which Z is attached in the compound of formula (II).

$R^1$ in the protecting group of formula (III) is typically unsubstituted $C_{1-6}$ alkyl. $R^1$ may for instance be unsubstituted $C_{1-4}$ alkyl, for instance $R^1$ may be methyl, ethyl, i-propyl, n-propyl, t-butyl, s-butyl or n-butyl. $R^1$ may for instance be methyl, ethyl, i-propyl or n-propyl. $R^1$ is often methyl or ethyl. Usually, $R^1$ is methyl.

$R^2$ in the protecting group of formula (III) is typically unsubstituted $C_{1-6}$ alkyl. $R^2$ may for instance be unsubstituted $C_{1-4}$ alkyl, for instance $R^2$ may be methyl, ethyl, i-propyl, n-propyl, t-butyl, s-butyl or n-butyl. $R^2$ may for instance be methyl, ethyl, i-propyl or n-propyl. $R^2$ is often methyl or ethyl. Usually, $R^2$ is methyl.

$R^3$ in the protecting group of formula (III) is typically unsubstituted $C_{1-6}$ alkyl. $R^3$ may for instance be unsubstituted $C_{1-4}$ alkyl, for instance $R^3$ may be methyl, ethyl, i-propyl, n-propyl, t-butyl, s-butyl or n-butyl. $R^3$ may for instance be methyl, ethyl, i-propyl or n-propyl. $R^3$ is often methyl or ethyl. Usually, $R^3$ is methyl.

$R^1$, $R^2$ and $R^3$ are typically independently selected from unsubstituted $C_{1-6}$ alkyl groups. $R^1$, $R^2$ and $R^3$ may for instance be independently selected from unsubstituted $C_{1-4}$ alkyl groups, i.e. from methyl, ethyl, i-propyl, n-propyl, t-butyl, s-butyl and n-butyl. $R^1$, $R^2$ and $R^3$ may for instance be independently selected from methyl, ethyl, i-propyl and n-propyl. $R^1$, $R^2$ and $R^3$ are often independently selected from methyl and ethyl.

Typically, $R^1$ is methyl, $R^2$ is methyl and $R^3$ is methyl.

Thus, the protecting group $R^P$ is typically -[2-(trimethylsilyl)ethoxy]methyl](SEM).

Z may be a group of formula (IV):

(IV)

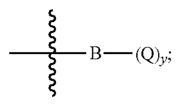

wherein:

each Q is the same or different and is a group selected from —$OR^E$, —OH, and fluoride;

each $R^E$ is the same or different and is a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, acyl, ester, amido, and haloalkyl, wherein two or more $R^E$ groups may be bonded together to form one or more rings; and y is 2 or 3.

$R^E$ may be selected from substituted or unsubstituted $C_{1-10}$ alkyl, wherein two or more $R^E$ groups may be bonded together to form one or more rings. For instance, two $R^E$ groups may together form a substituted or unsubstituted $C_{1-10}$ alkylene group as described herein. Z is often a group of formula —$B(OR^E)_2$. Thus, Z is often a boronic ester group. Z is often a cyclic boronic ester group. For example, Z may be a group of formula (V):

(V)

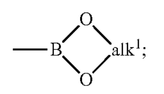

wherein $alk^1$ is a substituted or unsubstituted alkylene group, optionally interrupted with one or more —O— or —$N(R^F)$— groups, wherein $R^F$ is a group selected from H, substituted or unsubstituted $C_{1-10}$ alkyl, acyl, ester, amido and acyloxy. Often, $alk^1$ is a substituted or unsubstituted $C_{1-10}$ alkylene group, optionally interrupted with one —O— or —$N(R^F)$— groups, wherein $R^F$ is a group selected from H, substituted or unsubstituted $C_{1-10}$ alkyl, acyl, ester, amido and acyloxy. $alk^1$ may be a substituted or unsubstituted $C_{2-5}$ alkylene group which is uninterrupted.

For example, Z may be a group of formula (VI) or (VII):

(VI)

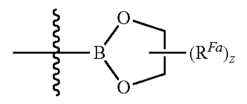

(VII)

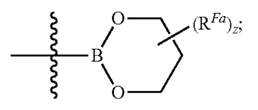

wherein: each $R^{Fa}$ is independently a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-10}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester; and z is an integer from 0 to 6.

In formula (VI) and (VII), each $R^{Fa}$ may be bonded to any one of the alkylene carbon atoms bridging the two O atoms. Each $R^{Fa}$ may be a group independently selected from substituted or unsubstituted $C_{1-10}$ alkyl groups. For example, $R^{Fa}$ may be methyl or ethyl.

Often, Z is a group selected from

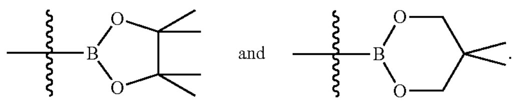

Thus, Z may be a pinacol boronic ester or a neopentyl glycol boronic ester.

Often, Z is:

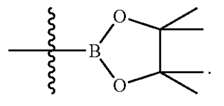 [SMILES: *B1OC(C)(C)C(C)(C)O1]

Process Conditions

The amount of the copper compound may be any suitable amount. The ratio of the amount of the organoboron compound to the amount of the copper compound (i.e. the molar ratio) may be from 1:40 to 40:1, for instance from 1:20 to 20:1, for example from 1:5 to 5:1, for instance from 1:3 to 3:1.

Typically, the amount of the organoboron compound is less than the amount of the copper compound. Thus, the ratio of the amount of the organoboron compound to the amount of the copper compound (i.e. the molar ratio) is typically from 1:40 to 10:11, for instance from 1:20 to 6:7. The ratio of the amount of the organoboron compound to the amount of the copper compound may for instance be from 1:10 to 5:6, for instance from preferably from 1:5 to 4:5, for instance from or for example from 1:2 to 4:5, or from 5:9 to 4:5. For instance, the ratio of the amount of the organoboron compound to the amount of the copper compound may be from 3:5 to 3:4, or for example from 5:8 to 5:7. Typically it is about 2:3.

The process of the invention is typically carried out in solution. The process may be carried out in solution in any suitable solvent.

Thus, step (i), of treating the organoboron compound of formula (II) with the $^{18}F^-$ and the copper compound, is typically carried out in the presence of a solvent. Typically, the solvent comprises a polar aprotic solvent. Usually, the solvent is a polar aprotic solvent, or a mixture of two, or more than two (for instance three or four) polar aprotic solvents. Typically, the solvent (e.g. the polar aprotic solvent, or the mixture of two or more polar aprotic solvents) is anhydrous. Polar aprotic solvents are well known to the skilled person, and include 1,3-dimethyl-2-imidazolidinone (DMI), dimethyl formamide (DMF), N,N-dimethyl acetamide and acetonitrile. Thus, treating the organoboron compound of formula (II) with the $^{18}F^-$ and the copper compound may be carried out in the presence of a solvent selected from 1,3-dimethyl-2-imidazolidinone (DMI), dimethyl formamide (DMF), N,N-dimethyl acetamide and acetonitrile, or a mixture of two or more thereof.

The presence of DMI is particularly preferred, because as demonstrated in the Example herein, the use of DMI unexpectedly led to a significantly improved radiochemical yield for [$^{18}$F]olaparib. Thus, typically, treating the organoboron compound of formula (II) with the $^{18}F^-$ and the copper compound is carried out in the presence of a solvent which comprises 1,3-dimethyl-2-imidazolidinone (DMI). The solvent may be DMI or a mixture of DMI and one or more other polar aprotic solvents. For instance, the solvent may be a mixture of DMI and acetonitrile. Typically the solvent is anhydrous. Thus, typically, treating the organoboron compound of formula (II) with the $^{18}F^-$ and the copper compound is carried out in the presence of an anhydrous solvent which comprises anhydrous 1,3-dimethyl-2-imidazolidinone (DMI). The solvent may be anhydrous DMI or a mixture of anhydrous DMI and one or more other anhydrous polar aprotic solvents. For instance, the solvent may be a mixture of anhydrous DMI and anhydrous acetonitrile.

Often, the solvent comprises 1,3-dimethyl-2-imidazolidinone (DMI), the copper compound is $[(impy)_4Cu^{II}(OTf)_2]$, Z is a boronic ester group as defined herein, and the ratio of the amount of the organoboron compound to the amount of the copper compound is from 3:5 to 3:4.

The organoboron compound, the copper compound and the $^{18}F^-$ (and, when present, the solvent) are typically heated at a temperature of from 80° C. to 150° C. For instance, the organoboron compound, the copper compound and the $^{18}F^-$ (and, when present, the solvent) may be heated at a temperature of from 100° C. to 140° C., or from 100° C. to 130° C., for instance at about 120° C. The aforementioned reagents may be heated at said temperature for a length of time of at least 1 minute, for instance at least 10 minutes, or for instance at least 20 minutes. The reagents may for instance be heated at said temperature for a length of time of from 1 minute to 1 hour, for instance from 10 minutes to 30 minutes, or from 20 minutes to 40 minutes.

Often, the step of (i) treating the organoboron compound of formula (II) with $^{18}F^-$ and a copper compound comprises:

(a) mixing the organoboron compound of formula (II), the copper compound, the $^{18}F^-$ and the solvent as defined above (e.g. the polar aprotic solvent, or the mixture of two or more polar aprotic solvents); and (b) heating the resulting mixture to at a temperature of from 80° C. to 150° C. for from 10 to 30 minutes.

Often (b) comprises heating the resulting mixture in a sealed container. The components and steps in this process may be as described anywhere herein.

The $^{18}F^-$ used in the process of the invention may be in any suitable form. Typically, the $^{18}F^-$ is present as a salt. Thus, the process of the invention may comprise treating the organoboron compound with (i) a salt of $^{18}F^-$ and (ii) said copper compound. Typically the concentration of $^{18}F^-$ is less than or equal to $10^{-4}$ M, for instance less than or equal to $10^{-5}$ M. In some cases, the concentration of $^{18}F^-$ will be nanomolar or less, for instance less than or equal to $10^{-8}$ M. $^{19}F^-$ may also be present. In such a case, the total fluoride concentration (including $^{18}F^-$ and $^{19}F^-$) may be less than or equal to $10^{-4}$ M, for instance less than or equal to $10^{-5}$ M.

Any suitable source of $^{18}F^-$ may be used. As will be understood by the skilled person the $^{18}F^-$ will typically be present in the form of a salt, with a counter cation. Any suitable counter cation may be used. Typically, the counter cation is a quaternary ammonium cation, for instance tetrabutylammonium, or an alkali metal cation, for instance $Cs^+$ or $K^+$, or a proton, $H^+$. Typically, when an alkali metal cation is employed, the alkali metal is cation complexed in a cryptand, for instance aminopolyether 2.2.2 ($K_{222}$), which is commercially available as Kryptofix-222. Advantageously, the addition of such a cryptand enables the fluoride ion $^{18}F^-$ to be solubilized in a polar aprotic solvent, for instance acetonitrile or DMF.

It also enables the formation of a 'naked fluoride ion' as a KF—$K_{222}$ complex. In one embodiment, therefore, the source of $^{18}F^-$ is a [$^{18}$F]KF—$K_{222}$ complex. Alternatively, the source of $^{18}F^-$ may be [$^{18}$F]CsF, or [$^{18}$F]HF. Typically, $^{18}F^-$ is present as $[^{18}F]KF—K_{222}$ or $[^{18}F]HF$. More typically, $^{18}F^-$ is present as $[^{18}F]KF—K_{222}$.

The process, and in particular the step (i) of treating the organoboron compound of formula (II) with $^{18}F^-$ and a copper compound, may be performed under any suitable atmosphere. For instance, the process, and in particular the step of (i) treating the organoboron compound of formula (II) with $^{18}F^-$ and a copper compound, may be performed under an inert atmosphere such as nitrogen or argon, or it may be performed in the presence of oxygen, for instance in air. Often, the process, and in particular the step of (i) treating the organoboron compound of formula (II) with $^{18}F^-$ and a copper compound, is performed in air.

Deprotection Step

The step of treating the organoboron compound of formula (II) with $^{18}F^-$ and a copper compound is thought to produce an intermediate of the following formula wherein Z in formula (II) has been replaced by $^{18}F$ but the phthalazone nitrogen still bears the protecting group $R^P$:

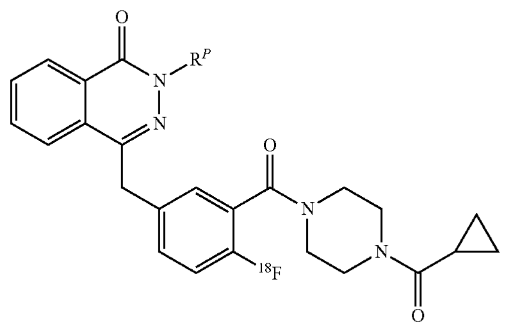

The step of (ii) removing the protecting group $R^P$, to produce the compound of formula (I), $^{18}F$ olaparib, may be referred to as the deprotection step. The deprotection step (removing the protecting group) is generally performed after the step of treating the organoboron compound with the copper compound and the $^{18}F^-$. The deprotection step may be performed by any suitable method for removing an N-[2-(trialkylsilyl)ethoxy]methyl] protecting group of formula (III). Such methods are known to the skilled chemist. Three alternative methods that are often employed in the art to remove a [2-(trialkylsilyl)ethoxy]methyl] group, such as SEM, are (a) treatment with an acid, (b) treatment with a source of boron trifluoride, or (c) treatment with a quaternary ammonium fluoride salt. Thus, typically, removing the protecting group $R^P$ comprises treatment with an acid, a source of boron trifluoride or a quaternary ammonium fluoride salt (see http://www.commonorganicchemistry.com/Rxn_Pages/SEM_Protection/SEM_Protection_In dex.htm).

Usually, in the present invention, removing the protecting group $R^P$ comprises treatment with an acid. The acid may be an organic acid, for instance trifluoroacetic acid (TFA), or a mineral acid, for instance HCl. Typically, however, an organic acid is employed, usually TFA.

Treatment with an acid, for instance TFA, may be performed at room temperature but is typically carried out at an elevated temperature, for instance at a temperature of from 50° C. to 150° C. Conveniently, in the present invention, the treatment with an acid is carried out at the same temperature as step (i) of treating the organoboron compound of formula (II) with $^{18}F^-$ and a copper compound. Thus, often, the step (ii) of removing the protecting group $R^P$ to produce the compound of formula (I) comprises treatment with an acid (which is typically an organic acid such as, for instance, TFA) at a temperature of from 80° C. to 150° C. Thus, if the step (i) is performed at a temperature as defined hereinbefore for step (i), for instance at a temperature of from 80° C. to 150° C., and for a certain period of time as defined above for step (i), then step (ii) may simply comprise adding the acid, for instance TFA, and maintaining said temperature for a further period of time. The further period of time may for instance be at least 1 minute, more typically at least 10 minutes, or for instance at least 20 minutes. The further period of time may for instance be from 1 minute to 1 hour, for instance from 10 minutes to 30 minutes, or from 20 minutes to 40 minutes.

Preferably, removing the protecting group $R^P$ comprises treatment with trifluoroacetic acid (TFA). Often, removing the protecting group $R^P$ comprises treatment with trifluoroacetic acid at a temperature of from 80° C. to 150° C., for instance at a temperature of from 100° C. to 140° C., or 100° C. to 130° C., for instance at about 120° C. The treatment with TFA at said temperature may be for a length of time of at least 1 minute, for instance at least 10 minutes, or for instance at least 20 minutes. The treatment with TFA at said temperature may for instance be for a length of time of from 1 minute to 1 hour, for instance from 10 minutes to 30 minutes, or from 20 minutes to 40 minutes.

Alternatively, however, removing the protecting group $R^P$ may comprise treatment with a source of boron trifluoride. The source of boron trifluoride may be boron trifluoride itself, i.e. $BF_3$. However, a more convenient, easy to handle, source of boron trifluoride is boron trifluoride diethyl etherate ($BF_3—OEt_2$), which is a liquid at room temperature. Typically, therefore, the source of boron trifluoride is boron trifluoride diethyl etherate. The treatment with boron trifluoride diethyl etherate is often performed at from 0° C. to room temperature.

As a further alternative, removing the protecting group $R^P$ may comprise treatment with a quaternary ammonium fluoride salt, for instance with tetra-n-butylammonium fluoride (TBAF), tetra-n-propylammonium fluoride or tetraethylammonium fluoride. TBAF is commonly employed. The treatment with a quaternary ammonium fluoride salt is typically performed at elevated temperature, for instance at a temperature of from 50° C. to 150° C. Conveniently, in the present invention, the treatment with a quaternary ammonium fluoride salt may be carried out at the same temperature as step (i) of treating the organoboron compound of formula (II) with $^{18}F^-$ and a copper compound. Thus, the step (ii) of removing the protecting group $R^P$ to produce the compound of formula (I) may comprise treatment with quaternary ammonium fluoride salt (e.g. TBAF) at a temperature of from 50° C. to 150° C. or from 80° C. to 150° C. Thus, if the step (i) is performed at a temperature as defined hereinbefore for step (i), for instance at a temperature of from 80° C. to 150° C., and for a certain period of time as defined above for step (i), then step (ii) may simply comprise adding the quaternary ammonium fluoride salt (e.g. TBAF), and maintaining said temperature for a further period of time. The further period of time may for instance be at least 1 minute, more typically at least 10 minutes, or for instance at least 20 minutes. The further period of time may for instance be from 1 minute to 1 hour, for instance from 10 minutes to 30 minutes, or from 20 minutes to 40 minutes.

Removing the protecting group $R^P$ yields the compound of formula (I), $[^{18}F]$olaparib.

After removal of the protecting group $R^P$, the process may optionally further comprise (iii) quenching the reaction by addition of a polar protic solvent, for instance water. This step is typically carried out at room temperature. Thus, after removal of the protecting group $R^P$, but prior to addition of the polar protic solvent, a step of cooling to room temperature may be needed. Thus, the process may optionally for instance comprise (iii) cooling to room temperature, quenching with $H_2O$, eluting over an Oasis HLB Plus cartridge (preconditioned with 1:5 vol/vol MeOH and $H_2O$), and eluting the product with $CH_3CN$. The $CH_3CN$ solution may then be concentrated by evaporating some of the $CH_3CN$.

The process typically further comprises (iv) recovering the compound of formula (I). Recovering the compound of formula (I) means isolating it from the reaction mixture or, if the reaction is quenched, from the quenched reaction mixture. The compound of formula (I) is typically recovered by preparative high-performance liquid chromatography (i.e. by preparative HPLC) or by semi-preparative HPLC. Indeed, the inventors have found that preparative or semi-preparative HPLC can be used to recover the compound of formula (I) in pure form. Thus, recovering the compound of formula (I) typically comprises performing preparative or semi-preparative HPLC.

For instance, the above-mentioned $CH_3CN$ solution of the product is diluted with 28% MeCN/72% 25 mM $NH_4HCO_2$ in $H_2O$ and loaded directly onto a 2 mL HPLC loop and injected on a semi-Prep HPLC column and eluted with 28% MeCN/72% 25 mM $NH_4HCO_2$ in $H_2O$. The [$^{18}$F]olaparib may be collected in $H_2O$ and eluted over a Oasis HLB Plus cartridge (preconditioned with 1:5 v/v $MeOH:H_2O$). The cartridge may then be washed with $H_2O$, and the product eluted with EtOH. The ethanol may then be removed (e.g. by evaporation under a flow of $N_2$ while heating at 100° C.) to produce [$^{18}$F]olaparib as a dry residue.

The recovered [$^{18}$F]olaparib may then be re-dissolved for further use, for instance in a pharmaceutically acceptable solution. Pharmaceutically acceptable solutions for injection or infusion may contain as carrier, for example, sterile water or preferably they may be in the form of sterile, aqueous, isotonic saline solutions. The recovered [$^{18}$F]olaparib may for instance be re-dissolved in phosphate buffered saline, which is generally sterile. Typically, the pH of the solution is from 6.9 to 7.9, more typically about 7.4. Dimethylsulfoxide (DMSO) may also be present with the PBS. Thus, the recovered [$^{18}$F]olaparib may be re-dissolved in a mixture of phosphate buffered saline and DMSO. The recovered [$^{18}$F] olaparib may for instance be re-dissolved in 10 vol. % DMSO in PBS, with a pH of 7.4.

The process of the invention may further comprise using the recovered [$^{18}$F]olaparib in any of the methods of use defined herein. For instance, the process of the invention may further comprise administering to a subject the recovered [$^{18}$F]olaparib, or a pharmaceutically acceptable salt thereof, and imaging the subject by positron emission tomography (PET). Alternatively, the process of the invention may further comprise contacting a cell sample or tissue sample with the recovered [$^{18}$F]olaparib or a pharmaceutically acceptable salt thereof, and imaging the cell sample or tissue sample by positron emission tomography (PET).

Automated Process

In one embodiment of the invention, the process of the invention as defined herein for producing [$^{18}$F]olaparib is conducted in an automated synthesizer. The automated synthesizer may be any suitable automated synthesizer, as are well known to the skilled person. Automated synthesizers may include one or more means for performing the process of the invention. For instance, an automated synthesizer may comprise one or more of (i) a means for mixing the reagents used in the process of the invention, (ii) a means for heating the mixed reagents of the invention and (iii) means for isolating the compound of formula (I), [$^{18}$F]olaparib. Such automated synthesizers may be used for the production of [$^{18}$F]olaparib. Thus, the automated synthesizer may be suitable for use in a clinical setting, for instance in a imaging centre equipped with PET imaging and/or scanning apparatus.

An automated synthesizer may comprise one or more reagents used in the process of the invention. For example, the automated synthesizer may be pre-loaded with one or more reagents, for instance an organoboron compound as described anywhere herein or a copper compound as described anywhere herein. Alternatively, the process of the invention may be conducted in an automated synthesizer, which process further comprises loading the automated synthesizer with one or more reagents. The reagents may be loaded into the automated synthesizer by inserting a pre-packaged amount of the reagent, for instance in the form of a capsule. For instance, the process of the invention may further comprise (prior to treating the organoboron compound with the copper compound and $^{18}F^-$) inserting a pre-packaged sample of a copper compound as defined anywhere herein or an organoboron compound as defined anywhere herein into an automated synthesizer.

Precursor Compounds and their Production

The invention also provides an organoboron compound of formula (II)

(II)

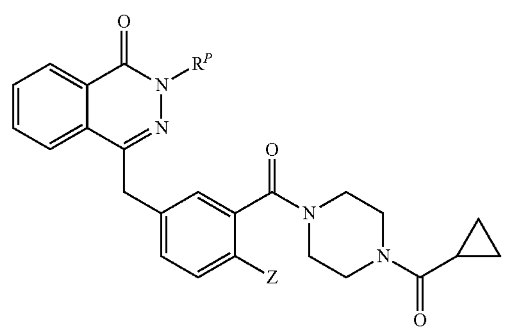

wherein Z is a boronic ester group, a boronic acid group, a boronate group or a trifluoroborate group; and $R^P$ is a group of formula (III)

(III)

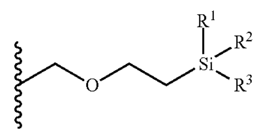

wherein $R^1$ is $C_{1-6}$ alkyl; $R^2$ is $C_{1-6}$ alkyl; and $R^3$ is $C_{1-6}$ alkyl.

In the organoboron compound of formula (II), any of Z, $R^1$, $R^2$ and $R^3$ may be as further defined hereinbefore for the compound of formula (II) used in the process of the invention for producing [$^{18}$F]olaparib. Thus, for example, Z may be a boronic ester group, which may itself be as further defined herein, and $R^1$, $R^2$ and $R^3$ may all be methyl groups.

The organoboron compound of formula (II) may be produced by (i) treating a compound of formula (X)

(X)

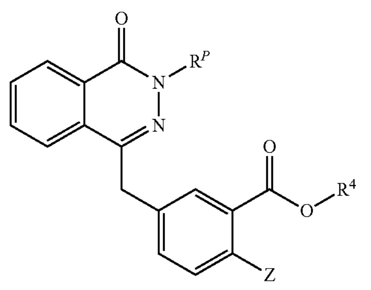

wherein Z is a boronic ester group, a boronic acid group, a boronate group or a trifluoroborate group; $R^P$ is a group of formula (III)

(III)

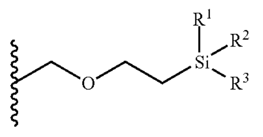

wherein $R^1$ is $C_{1-6}$ alkyl; $R^2$ is $C_{1-6}$ alkyl; $R^3$ is $C_{1-6}$ alkyl; and wherein $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl, and $R^4$ is preferably $C_{1-6}$ alkyl;

with a solution of lithium hydroxide in an organic solvent, such as for instance tetrahydrofuran, typically at 0° C.; and (ii) extracting the resulting mixture with an organic solvent, for instance EtOAc, and then removing the solvent to produce a residue; and (iii) treating the residue with dichloromethane (DCM), 2-(1H-benzotriazol-1-yl)-1,1,3,3-tetramethyluronium hexafluorophosphate (HBTU) and N,N-Diisopropylethylamine (DIPEA), and subsequently treating the resulting mixture with N-cyclopropylcarbonylpiperazine.

Typically, producing the organoboron compound of formula (II) further comprises: (iv) performing a solvent removal step; (v) recovering the crude product, typically by column chromatography; and (vi) performing a purification step to recover the organoboron compound of formula (II), wherein the purification step typically comprises reverse phase HPLC.

This reaction is exemplified hereinbelow.

The invention also therefore provides a compound of formula (X)

(X)

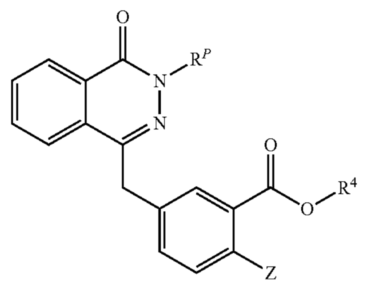

wherein Z is a boronic ester group, a boronic acid group, a boronate group or a trifluoroborate group; $R^P$ is a group of formula (III)

(III)

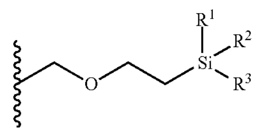

wherein $R^1$ is $C_{1-6}$ alkyl; $R^2$ is $C_{1-6}$ alkyl; $R^3$ is $C_{1-6}$ alkyl; and $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl, and preferably $R^4$ is $C_{1-6}$ alkyl.

Any of Z, $R^1$, $R^2$ and $R^3$ in the compound of formula (X) may be as further defined hereinbefore for the compound of formula (II) used in the process of the invention for producing [$^{18}$F]olaparib. Thus, for example, Z may be a boronic ester group, which may itself be as further defined herein, and $R^1$, $R^2$ and $R^3$ may all be methyl groups.

Usually, in the compound of formula (X), $R^4$ is $C_{1-4}$ alkyl, for instance methyl or ethyl. Often, $R^4$ is methyl.

The compound of formula (X) may be produced by (i) treating a compound of formula (XI)

(XI)

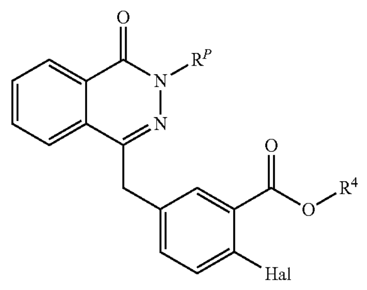

wherein Hal is Br, Cl, I or At; $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl, and preferably $R^4$ is $C_{1-6}$ alkyl; and $R^P$ is a group of formula (III)

(III)

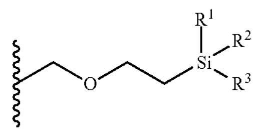

wherein $R^1$ is $C_{1-6}$ alkyl; $R^2$ is $C_{1-6}$ alkyl; and $R^3$ is $C_{1-6}$ alkyl, with a precursor to Z in the presence of a palladium (II) catalyst.

Typically, treating the compound of formula (XI) with the precursor to Z in the presence of the palladium (II) catalyst is performed in the presence of a solvent. The solvent is typically a polar aprotic solvent, for instance DMF, and is typically a dry, degassed solvent. A metal acetate salt, for instance potassium acetate, is typically also present. Usually, treating the compound of formula (XI) with the precursor to Z in the presence of the palladium (II) catalyst (and optionally the solvent and metal acetate salt) is performed at an elevated temperature, for instance at from 50° C. to 110° C., or for example from 70° C. to 90° C. Usually, the process comprises heating at said elevated temperature for at least 6 hours, for instance at least 12 hours, for example at least 15 hours. The reaction is usually performed in an inert atmosphere, for instance under argon or nitrogen, typically argon. Upon completion, the reaction is typically cooled and passed through a plug of Celite before extracting with an organic solvent (e.g. EtOAc) and washing (for example with a lithium chloride solution). The organic phases are typically then collected and excess solvent removed in vacuo. The crude material can then purified by flash column chromatography The palladium (II) catalyst is a compound comprising palladium (II). The catalyst is typically soluble in any solvent which is employed for the reaction. Often, a polar aprotic solvent such as DMF is employed as the solvent and the palladium (II) catalyst is soluble in said solvent. The palladium (II) catalyst is typically a palladium (II) complex, for instance a complex of the formula $[Pd(L)_2]X_2$ wherein each L is a neutral bidentate ligand and each X is a monoanion. Each X may for instance be Br, Cl or I. Each L may for instance be a diphosphine ligand, for instance 1,1'-bis(diphenylphosphanyl)ferrocene (dppf) or 1,2-bis(diphenylphosphino)ethane (dppe). Often, dppf is employed. Often X is Cl. The palladium (II) catalyst may for instance be $Pd(dppf)_2Cl_2$.

If the Z group in the compound of formula (X) being produced is a boronic ester group or a boronic acid group, the precursor to Z is typically the corresponding diboron compound, i.e. a compound Z—Z wherein each Z is the same boronic ester group or the same boronic acid group and the bond between Z and Z in Z—Z is a boron-boron bond.

Thus, for example, when the Z group in the compound of formula (X) being produced is a boronic ester group or a boronic acid group, the precursor to Z may be $(Q)_y$-B—B-$(Q)_y$ wherein each y is 2 and each Q is a group selected from —$OR^E$ and —OH, wherein each $R^E$ is a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, acyl, ester, amido, and haloalkyl, wherein two or more $R^E$ groups may be bonded together to form one or more rings.

For instance, each Z in Z—Z may be the same group of formula $B(OR^E)_2$ as defined herein, where the Z group desired is a boronic ester group. Alternatively, each Z in Z—Z may be the same group of formula (V) as defined herein, the same group of formula (VI) as defined herein or same group of formula (VII) as defined herein. For instance, each Z in Z—Z may be a group of formula:

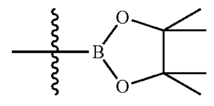 [SMILES: *B1OC(C)(C)C(C)(C)O1]

(in which case the precursor to Z is bis(pinacolato) diboron) or each Z in Z—Z may be a group of formula:

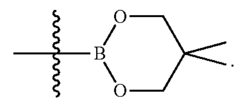 [SMILES: *B1OCC(C)(C)CO1]

When the Z group in the compound of formula (X) being produced is a trifluoroborate group, a reaction to add a boronic acid moiety, $B(OH)_2$, at Z may first be performed as outlined above, using for example the reagent bisboronic acid (also known as tetrahydroxydiboron, which is commercially available). The resulting boronic acid group at Z on the phenyl ring can then be reacted with potassium bifluoride $K[HF_2]$ to form a trifluoroborate —$[BF_3]^+$ at Z.

Similarly, when the desired Z group is a boronate group, a reaction to add a boronic acid or boronic ester moiety, $B(OR^E)_2$ as defined above, at Z may first be performed as outlined above, using for example the bis-boron reagent $(Q)_y$-B—B-$(Q)_1$ as defined above. The resulting boronic acid group or boronic acid ester group at Z on the phenyl ring can then be oxidised to form a boronate group at Z.

The reaction to produce a compound of formula (X) is exemplified hereinbelow.

The invention also provides a compound of formula (XI)

(XI)

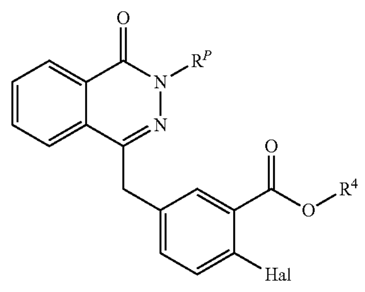

wherein Hal is Br, Cl, I or At; $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl, and preferably $R^4$ is $C_{1-6}$ alkyl; and $R^P$ is a group of formula (III)

(III)

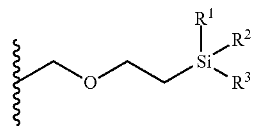

wherein $R^1$ is $C_{1-6}$ alkyl; $R^2$ is $C_{1-6}$ alkyl; and $R^3$ is $C_{1-6}$ alkyl.

Any of $R^1$, $R^2$ and $R^3$ in the compound of formula (XI) may be as further defined hereinbefore for the compound of formula (II) used in the process of the invention for producing [$^{18}$F]olaparib. Thus, for example, $R^1$, $R^2$ and $R^3$ may all be methyl groups. Usually, in the compound of formula (XI), $R^4$ is $C_{1-4}$ alkyl, for instance methyl or ethyl. Often, $R^4$ is methyl. Hal is often Br, Cl or I, more typically Br.

The compound of formula (XI) may be produced by treating a compound of formula (XII)

(XII)

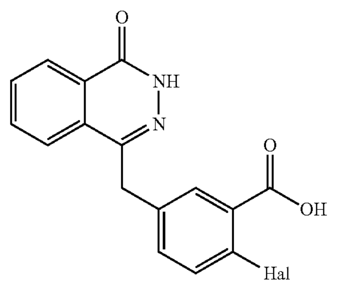

wherein Hal is Br, Cl, I or At, with: (i) $R^4$I, wherein $R^4$ is substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, or substituted or unsubstituted heteroaryl, and preferably $R^4$ is $C_{1-6}$ alkyl (and $R^4$ may be as further defined above for the compound of formula XI); and subsequently (ii) a 2-(trialkylsilyl)ethoxymethyl halide.

The 2-(trialkylsilyl)ethoxymethyl halide is typically a compound of the following formula:

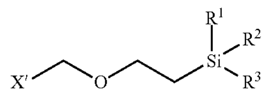

wherein $R^1$ is $C_{1-6}$ alkyl; $R^2$ is $C_{1-6}$ alkyl; $R^3$ is $C_{1-6}$ alkyl; and X' is halo. Typically, X' is Br, Cl or I. X' is usually Cl. $R^1$, $R^2$ and $R^3$ may be as further defined hereinbefore for the compound of formula (II) used in the process of the invention for producing [$^{18}$F]olaparib. Thus, for example, $R^1$, $R^2$ and $R^3$ may all be methyl groups.

Treatment of the compound of formula (XII) with $R^4$I is typically performed in the presence of a solvent, for instance a polar aprotic solvent such as DMF, and usually the solvent is anhydrous. An anhydrous metal carbonate, for instance anhydrous potassium carbonate, is typically also present. Usually, this step is performed at elevated temperature, for instance at from 35° C. to 80° C., or for example from 40° C. to 70° C. Usually, the process comprises heating at said elevated temperature for at least 6 hours, for instance at least 12 hours. Upon completion, excess solvent is typically removed in vacuo and water is added to the crude material. The precipitate formed is then typically filtered and washed (e.g. with $Et_2O$) and typically dried in vacuo.

The subsequent treatment with the 2-(trialkylsilyl)ethoxymethyl halide is typically performed in the presence of a solvent, for instance a polar aprotic solvent such as THF, and usually the solvent is anhydrous. Sodium hydride is typically also present. Usually, the solvent and sodium hydride are added first, e.g. at 0° C., and then the 2-(trialkylsilyl)ethoxymethyl halide is added subsequently, usually dropwise. The reaction is typically then stirred for at least 6 hours, for instance at least 12 hours, or for example at least 15 hours. Upon completion, excess solvent is typically removed in vacuo and the product—the compound of formula (XI)—may be purified directly by flash column chromatography.

These reaction steps to produce a compound of formula (XI) are exemplified hereinbelow.

[$^{18}$F]Olaparib and Pharmaceutically Acceptable Salts and Compositions Thereof The invention further provides a compound which is [$^{18}$F]olaparib or a pharmaceutically acceptable salt thereof. [$^{18}$F]olaparib has the following formula (I)

(I)

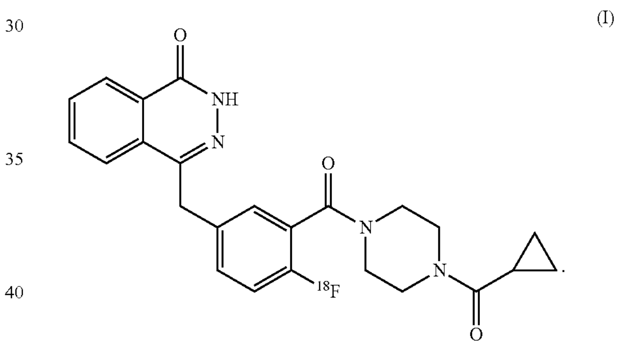

The term "pharmaceutically acceptable salt" as used herein, means a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

The invention further provides a pharmaceutical composition comprising (a) a compound which is [$^{18}$F]olaparib or a pharmaceutically acceptable salt thereof, and (b) a pharmaceutically acceptable carrier or diluent.

The compound which is [$^{18}$F]olaparib or a pharmaceutically acceptable salt thereof may in principle be administered in a variety of dosage forms. The compound of the invention is typically however administered parenterally, whether subcutaneously, intravenously, intramuscularly, intrasternally, transdermally or by infusion techniques. It is often administered by injection or infusion. In principle, however, it could be administered orally, for example as tablets, troches, lozenges, aqueous or oily suspensions, dispersible powders or granules, or as a suppository.

The compound which is [$^{18}$F]olaparib or a pharmaceutically acceptable salt thereof is typically formulated for administration with a pharmaceutically acceptable carrier or diluent.

Solutions for injection or infusion may contain as carrier, for example, sterile water or preferably they may be in the form of sterile, aqueous, isotonic saline solutions.

Thus, often, the pharmaceutical composition comprises (a) said compound which is [isF]olaparib or a pharmaceutically acceptable salt thereof, and (b) a pharmaceutically acceptable carrier or diluent, wherein the pharmaceutically acceptable carrier or diluent comprises sterile water or a sterile, aqueous, isotonic saline solution. The pharmaceutically acceptable carrier or diluent may for instance comprise phosphate buffered saline (PBS), which is typically sterile. Usually, the pH of the PBS solution is from 6.9 to 7.9, more typically about 7.4. Dimethylsulfoxide (DMSO) may also be present with the PBS. Thus, the pharmaceutically acceptable carrier or diluent may comprise phosphate buffered saline and DMSO, for instance 10 vol. % DMSO in PBS, with a pH of 7.4.

In terms of other possible dosage forms, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes. Liquid dispersions for oral administration may be syrups, emulsions and suspensions. The syrups may contain as carriers, for example, saccharose or saccharose with glycerine and/or mannitol and/or sorbitol. Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Uses of [$^{8}$F]Olaparib

The present inventors have demonstrated that [$^{18}$F]olaparib can be used to measure the distribution, uptake, and PARP-binding of olaparib using PET imaging in mouse models of pancreatic ductal adenocarcinoma (PDAC). Furthermore, the use of [$^{18}$F]olaparib for detecting DNA damage following external beam irradiation has been demonstrated, as well as its relationship with tumour hypoxia. [$^{18}$F]olaparib was found to have great potential for non-invasive tumour imaging and monitoring of radiation damage. Thus, the invention has provided, for the first time, successful in vivo translation of [$^{18}$F]olaparib for PET imaging. Imaging of PARP using the radiolabelled inhibitor is proposed for patient selection, outcome prediction, dose optimisation, genotoxic therapy evaluation, and target engagement imaging of novel PARP-targeting agents. When translated to the clinic, PET imaging with [$^{18}$F]olaparib will allow: (a) better patient selection, by determining tumour drug uptake; (b) measurement of the biological effects of genotoxic cancer treatment, such as chemo- and radiotherapy; and (c) allow better patient stratification, making the use of PARP inhibitors even more effective.

Accordingly, the invention provides a method of imaging a subject, comprising administering to the subject a compound which is [$^{18}$F]olaparib or a pharmaceutically acceptable salt thereof, and imaging the subject by positron emission tomography (PET).

The subject may be a mammal, for instance a human.

The subject may for instance have cancer. The method in that case may be a method of imaging the cancer in the subject. In principle any cancer type may be imaged. However, sensitivity to PARP inhibition has been observed in cells with defects in homologous recombination other than BRCA deficiency. These include defects in phosphatase and tensin homolog (PTEN), ataxia telangiectasia mutation (ATM), and Aurora A, and may include other genotypic or phenotypic changes conveying a 'brca-ness' state to the tumour. This may e.g. include hypoxic tumours. Parp inhibitors are currently used in ovarian and breast cancer patients with BRCA (BRCA1 or BRCA2) mutations. (FDA and EMA approved). Also, PARP inhibitors have been extensively studied as cancer drugs, either as single agents, as radiation sensitizers, or as part of combination therapies, and are especially effective in tumours with BRCA mutations. Accordingly, the cancer may be a cancer with a BRCA mutation. Non-limiting examples of cancer types include pancreatic cancer, brain cancer, breast cancer or ovarian cancer. Typically, the cancer is brain cancer. It may for instance be glioblastoma.

Accordingly, the cancer may be a cancer which comprises cells having a defect in homologous recombination, optionally wherein the defect is a defect in phosphatase and tensin homolog (PTEN), Aurora A or an ataxia telangiectasia mutation (ATM), or is a genotypic or phenotypic change which conveys a 'brca-ness' state. The cancer may be one which is platinum therapy sensitive. The cancer may comprise a tumour with a BRCA mutation. The cancer may for instance be ovarian cancer or breast cancer, with a BRCA (BRCA1 or BRCA2) mutation. The cancer may comprise a tumour which comprises cells having a defect in homologous recombination, for instance a defect in PTEN, Aurora A or ATM, or a genotypic or phenotypic change which conveys a 'brca-ness' state. The tumour may be platinum therapy sensitive.

The cancer may comprise a hypoxic tumour.

Administering to the subject said compound typically comprises administering to the subject a composition which comprises said compound and a pharmaceutically acceptable diluent or carrier. It may for instance comprise administering to the subject a pharmaceutical composition of the invention comprising (a) a compound which is [$^{18}$F]olaparib or a pharmaceutically acceptable salt thereof, and (b) a pharmaceutically acceptable carrier or diluent. The pharmaceutical composition of the invention may be as further defined herein.

The method of the invention may further comprise determining, by the imaging: the distribution of the compound in the subject, for instance the distribution of the compound between normal tissue and tumour tissue, or otherwise diseased tissue, in the subject; the accumulation of the compound at a site of cancer in the subject; the level of PARP expression in the subject or at a site of cancer in the subject; the level of uptake or binding (for instance the level of PARP-binding) of the compound in the subject or at a site of cancer in the subject; the cellular effects or cellular response (for instance the extent of damage to DNA) in the subject following a genotoxic cancer treatment of the subject; the extent of radiation damage in a subject caused by radiotherapy; the ability of a candidate PARP inhibitor to bind to PARP in the subject; or an optimum dose of a PARP inhibitor, for instance olaparib for the subject.

The invention also provides an in vitro method of imaging a cell sample or a tissue sample, comprising contacting the cell sample or tissue sample with a compound which is [$^{18}$F]olaparib or a pharmaceutically acceptable salt thereof, and imaging the cell sample or tissue sample by positron emission tomography (PET).

In the in vitro method, the cell sample or tissue sample may comprise one or more cancer cells. It may for instance be a sample, e.g. a biopsy sample, obtained previously from a subject having cancer. The method in that case may be a method of imaging the cancer in the sample. In principle any cancer type may be imaged. The cancer may be a cancer which comprises cells having a defect in homologous recombination, optionally wherein the defect is a defect in phosphatase and tensin homolog (PTEN), Aurora A or an ataxia telangiectasia mutation (ATM), or is a genotypic or phenotypic change which conveys a 'brca-ness' state. The cancer may be one which is platinum therapy sensitive. The cancer may be a cancer with a BRCA mutation. It may for example be pancreatic cancer, brain cancer, breast cancer or ovarian cancer. The cancer may for example be brain cancer. It may for instance be glioblastoma.

The cancer may comprise a tumour with a BRCA mutation. The cancer may for instance be ovarian cancer or breast cancer, with a BRCA (BRCA1 or BRCA2) mutation.

Alternatively, the tumour may be one which comprises cells having a defect in homologous recombination, for instance a defect in PTEN, Aurora A or ATM, or a genotypic or phenotypic change which conveys a 'brca-ness' state. The cancer may comprise a tumour which is platinum therapy sensitive. The tumour may be one without a BRCA mutation, i.e. a non-BRCA-mutated tumour (beit somatic or germline).

The cancer may comprise a hypoxic tumour.

When the cell sample or tissue sample is a cell sample or a tissue sample that was previously obtained from a subject having cancer, the in vitro method may further comprise estimating, by the imaging: the level of accumulation of the compound at a site of cancer in the subject; the level of PARP expression in the subject or at a site of cancer in the subject; the level of uptake or binding (for instance the level of PARP-binding) of the compound in the subject or at a site of cancer in the subject; the cellular effects or cellular response (for instance the extent of damage to DNA) in the subject following a genotoxic cancer treatment of the subject; the extent of radiation damage in a subject caused by radiotherapy; the ability of a candidate PARP inhibitor to bind to PARP in the subject; or an optimum dose of a PARP inhibitor, for instance olaparib, for the subject.

Further provided is a method of diagnosing cancer in a subject, which method comprises (a) administering to the subject a compound which is [$^{18}$F]olaparib or a pharmaceutically acceptable salt thereof; (b) imaging the subject by PET; and (c) determining from the imaging whether or not the subject has cancer.

The invention also provides a compound which is [$^{18}$F]olaparib or a pharmaceutically acceptable salt thereof, for use in a method of diagnosing cancer in a subject, which method comprises (a) administering to the subject a compound which is [$^{18}$F]olaparib or a pharmaceutically acceptable salt thereof; (b) imaging the subject by PET; and (c) determining from the imaging whether or not the subject has cancer.

Further provided is an in vitro method of diagnosing cancer in a subject, which method comprises (a) contacting a cell sample or a tissue sample previously obtained from the subject with a compound which is [$^{18}$F]olaparib or a pharmaceutically acceptable salt thereof; (b) imaging the cell sample or the tissue sample by PET; and (c) determining from the imaging whether or not the subject has cancer.

The method of detection in any of the in vitro methods described herein may comprise autoradiography. Thus, autoradiography may be used instead of, or in addition to, PET, in any of the in vitro methods described herein.

The invention also provides a method of evaluating the suitability of a PARP inhibitor for treating cancer in a subject. The PARP inhibitor being evaluated may for instance be olaparib, rucaparib or talazoparib, and may for instance be olaparib itself, or a pharmaceutically acceptable salt thereof. Alternatively, the PARP inhibitor being evaluated may be other than olaparib and pharmaceutically acceptable salts thereof, for instance it may be selected from rucaparib or talazoparib and pharmaceutically acceptable salts thereof. The method of the invention for evaluating the suitability of a PARP inhibitor for treating cancer in a subject typically comprises:

(a) administering to a subject that has cancer a compound which is [$^{18}$F]olaparib or a pharmaceutically acceptable salt thereof;
(b) detecting the compound by imaging the subject by PET imaging; and
(c) determining from the imaging the suitability of the PARP inhibitor for treating the cancer in the subject.

The step of: (c) determining from the imaging the suitability of the PARP inhibitor for treating the cancer in the subject may comprises determining, from the imaging, the level of accumulation of the compound at a site of the cancer. Additionally or alternatively, step (c) may comprise observing, from the imaging, the distribution of the compound in the subject, for instance the distribution of the compound between normal tissue and tumour tissue, or otherwise diseased tissue, in the subject. Additionally or alternatively, step (c) may comprise determining, from the imaging, the level of uptake or binding (for instance the level of PARP-binding) of the compound.

The step of: (c) determining from the imaging the suitability of the PARP inhibitor for treating the cancer in the subject may for instance comprise: determining, from the imaging, the level of accumulation of the compound at a site of the cancer, wherein the site of the cancer is a tumour. The tumour may be a hypoxic tumour. Additionally or alternatively the tumour may be a tumour with a BRCA mutation. Thus, the tumour may be a hypoxic tumour with a BRCA mutation. The tumour may be one which comprises cells having a defect in homologous recombination, for instance a defect in PTEN, Aurora A or ATM, or a genotypic or phenotypic change which conveys a 'brca-ness' state. The tumour may for instance be is a pancreatic adenocarcinoma, a brain tumour, a brain metastasis, a breast tumour or an ovarian tumour. The tumour may be one which is platinum therapy sensitive. The tumour may be one without a BRCA mutation, i.e. a non-BRCA-mutated tumour (beit somatic or germline).

The step of: (c) determining from the imaging the suitability of the PARP inhibitor for treating the cancer in the subject may comprise determining, from the imaging, the level of PARP-1-binding of the inhibitor being evaluated.

The invention also provides a method of evaluating the effect of a genotoxic cancer treatment, which method comprises:

- administering to a subject that has cancer a compound which is [$^{18}$F]olaparib or a pharmaceutically acceptable salt thereof;
- detecting the compound by imaging the subject by PET imaging;
- performing a genotoxic cancer treatment on the subject;
- detecting the compound by imaging the subject by PET imaging after performing the genotoxic cancer treatment on the subject; and
- evaluating changes in the image of the subject or the detected amount of the compound before and after performing the genotoxic cancer treatment.

The method typically comprises:

- administering to a subject that has cancer a compound which is [$^{18}$F]olaparib or a pharmaceutically acceptable salt thereof;
- detecting the compound by imaging the subject by PET imaging;
- subsequently performing a genotoxic cancer treatment on the subject;
- after performing the genotoxic cancer treatment on the subject, administering to the subject the compound which is [$^{18}$F]olaparib or a pharmaceutically acceptable salt thereof and detecting the compound by imaging the subject by PET imaging; and
- evaluating changes in the image of the subject or the detected amount of the compound before and after performing the genotoxic cancer treatment.

Typically, an increased response arising from the compound in the image of the subject obtained after performing the genotoxic cancer treatment on the subject compared to that obtained before performing the genotoxic cancer treatment on the subject is indicative of efficacy of the genotoxic cancer treatment in terms of causing DNA damage. In a similar manner, an increased detected amount of the compound after performing the genotoxic cancer treatment on the subject compared to that obtained before performing the genotoxic cancer treatment on the subject is indicative of efficacy of the genotoxic cancer treatment in terms of causing DNA damage.

Typically, the genotoxic cancer treatment comprises radiotherapy or chemotherapy. The radiotherapy may be external radiotherapy, for instance external beam radiotherapy, or it may be internal radiotherapy. The genotoxic cancer treatment typically comprises external beam radiotherapy.

Evaluating changes in the image of the subject or the detected amount of the compound before and after performing the genotoxic cancer treatment typically comprises determining, from the imaging, a change in the level of accumulation of the compound at a site of the cancer.

Often, the site of the cancer is a tumour. The tumour may be a hypoxic tumour. Additionally or alternatively the tumour may be a tumour with a BRCA mutation. Thus, the tumour may be a hypoxic tumour with a BRCA mutation. The tumour may for instance be is a pancreatic adenocarcinoma, a brain tumour, a brain metastasis, a breast tumour or an ovarian tumour. The tumour may for instance be a brain tumour. The tumour may for instance be glioblastoma.

The invention also provides a method of evaluating a candidate PARP-targeting agent in a subject, which method comprises:

- administering to a subject a compound which is [$^{18}$F]olaparib or a pharmaceutically acceptable salt thereof;
- detecting the compound by imaging the subject by PET imaging;
- administering to the subject a candidate PARP-targeting agent;
- detecting the compound by imaging the subject by PET imaging after administering the candidate PARP-targeting agent; and
- evaluating changes in the image of the subject or the detected amount of the compound before and after administering the candidate PARP-targeting agent.

The method typically comprises:

- administering to a subject a compound which is [$^{18}$F]olaparib or a pharmaceutically acceptable salt thereof;
- detecting the compound by imaging the subject by PET imaging;
- subsequently administering to the subject a candidate PARP-targeting agent;
- after administering the candidate PARP-targeting agent, administering to the subject the compound which is [$^{18}$F]olaparib or a pharmaceutically acceptable salt thereof and detecting the compound by imaging the subject by PET imaging; and
- evaluating changes in the image of the subject or the detected amount of the compound before and after administering the candidate PARP-targeting agent.

Typically, a decreased response arising from the compound in the image of the subject obtained after administering the candidate PARP-targeting agent to the subject compared to that obtained before administering the candidate PARP-targeting agent to the subject is indicative of efficacy of the candidate PARP-targeting agent. In a similar manner, a decreased detected amount of the compound after administering the candidate PARP-targeting agent to the subject compared to that detected before administering the candidate PARP-targeting agent to the subject is indicative of efficacy of the candidate PARP-targeting agent.

The step of evaluating changes in the image of the subject or the detected amount of the compound before and after administering the candidate PARP-targeting agent may comprise: determining, from the imaging, a change in the level of PARP-binding by the compound before and after after administering the candidate PARP-targeting agent.

The step of evaluating changes in the image of the subject or the detected amount of the compound before and after administering the candidate PARP-targeting agent may comprise: determining, from the imaging, a change in the level of PARP-1-binding by the compound before and after after administering the candidate PARP-targeting agent.

The invention further provides [$^{18}$F]olaparib or a pharmaceutically acceptable salt thereof, for use in a method as defined anywhere herein.

The invention further provides the use of [$^{18}$F]olaparib or a pharmaceutically acceptable salt thereof in the manufacture of a medicament for use in a method as defined anywhere herein.

The invention further provides the use of [$^{18}$F]olaparib or a pharmaceutically acceptable salt thereof as a prognostic marker of outcome (overall survival (OS), in general). PARP1 expression levels in tumour tissue have been reported as independent prognostic markers of OS, especially in high grade serous ovarian carcinoma.

The invention is further described in the following Examples.

Example 1

1. General Experimental Information

All chemicals were purchased from Acros, Alfa Aesar, Fluorochem, Sigma-Aldrich and used as received without further purification. Solvents were purchased from Fisher, Rathburn or Sigma-Aldrich. When anhydrous solvents were required they were purified by expression through an activated alumina column built as described by Pangborn and Grubbs (Pangborn, A. B., Giardello, M. A., Grubbs, R. H., Rosen, R. K. & Timmers, F. J. Safe and convenient procedure for solvent purification. Organometallics 15, 1518-1520, 1996). Reactions were monitored by thin-layer chromatography (TLC) carried out on Merck Kiesegel 60 F254 plates, silica gel column chromatography was performed over Merck silica gel C60 (40-60 μm). All NMR spectra were recorded on Bruker DPX200, AV400, AVB400, AVC500, AVB500 and DRX500 spectrometers. Proton and carbon-13 NMR spectra are reported as chemical shifts (δ) in parts per million (ppm) relative to the solvent peak using the Bruker internal referencing procedure (edlock). Fluorine-19 NMR spectra are referenced relative to $CFCl_3$ in $CDCl_3$. Coupling constants (J) are reported in units of hertz (Hz). The following abbreviations are used to describe multiplicities—s (singlet), d (doublet), t (triplet), q (quartet), m (multiplet), brs (broad singlet). High resolution mass spectra (HRMS, m/z) were recorded on a Bruker MicroTOF spectrometer using positive electrospray ionization ($ESI^+$) or on a Micromass GCT spectrometer using filed ionization ($FI^+$) or chemical ionization ($CI^+$). Infrared spectra were recorded either as the neat compound or in a solution using a Bruker Tensor 27 FT-IR spectrometer. Absorptions are reported in wavenumbers ($cm^{-1}$) and only peaks of interest are reported. Optical rotations were measured on a PerkinElmer Polarimeter model 341 Specific rotations are reported in $10^{-1}$ deg $cm^2$ $g^{-1}$ and concentrations in g/100 mL. Melting points of solids were measured on a Griffin apparatus and are uncorrected. IUPAC names were obtained using the ACD/I-Lab service.

2. Synthesis Methods

Dimethyl (3-oxo-1,3,-dihydroisobenzofuran-1-yl)phosphonate

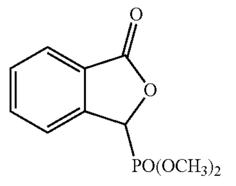

Dimethylphosphite (0.92 mL, 10.0 mmol) was added dropwise to a solution of sodium (0.58 g, 10.8 mmol) in MeOH (15 mL) at 0° C. To the solution, 2-carboxybenzaldehyde (1.00 g, 6.66 mmol) was added portionwise while stirring. The mixture was gradually warmed to room temperature and stirred for 6 hours. Methanesulfonic acid (0.77 mL, 11.9 mmol) was added dropwise and the mixture was stirred for another 30 minutes. The solution was concentrated in vacuo to produce a white solid, to which water was added (30 mL) and the crude product was extracted into DCM (3×30 mL). The organic layer was washed with water (2×30 mL), dried with $MgSO_4$ and filtered. The filtrate was concentrated in vacuo and washed with $Et_2O$ (3×20 mL), affording Dimethyl-(3-oxo-1,3-dihydrobenzofuran-1-yl) phosphonate (1.54 g, 96%) as a white solid.

$^1$H NMR (400 MHz, $CD_3OD$) δ=7.94 (d, J=7.5 Hz 1H), 7.83 (t, J=7.5 Hz, 1H), 7.75 (d, J=7.5 Hz, 1H), 7.68 (t, J=7.5 Hz, 1H), 6.10 (d, J=10.8, 1H), 3.91 (d, J=10.8 Hz, 3H), 3.72 (d, J=10.8 Hz, 3H). Data is in accordance with known literature; Mp: 90-92° C. (Menear, K. A., et al. 4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1. J Med Chem 51, 6581-6591, 2008).

2-Fluoro-5-((3-oxoisobenzofuran-1(3H)-ylidene) methyl)benzonitrile

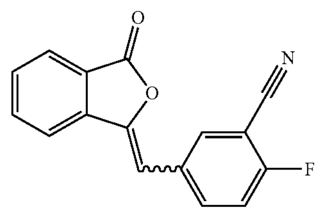 [SMILES: N#Cc1cc(C=C2OC(=O)c3ccccc32)ccc1F]

A solution of Dimethyldimethyl-(3-oxo-1,3-dihydrobenzofuran-1-yl)phosphonate (1.00 g, 4.13 mmol) and 2-fluoro-5-formylbenzonitrile (0.62 g, 4.13 mmol) in THF (50 mL) was prepared at room temperature. The solution was then cooled to 0° C. followed by the addition of $Et_3N$ (0.69 mL, 4.96 mmol). The reaction mixture was allowed to warm up to room temperature and was stirred for 48 h, followed by concentration in vacuo to produce a white solid. The solid was suspended in water, collected by vacuum filtration and washed with hexane (2×20 mL), $Et_2O$ (2×20 mL), and MeOH (2×20 mL) affording 2-Fluoro-5-((3-oxoisobenzofuran-1(3H)-ylidene)methyl)benzonitrile (0.88 g, 80%) as a white solid.

NMR spectra showed a 3:1 mixture of E and Z isomers. Where possible, shifts are assigned to each respective isomer. $^1$H NMR (400 MHz, DMSO-$d_6$) δ=8.21-8.12 (m, 1H), 8.08 (dt, J 8.0, 1.0 Hz, 1H), 8.00-7.97 (m, 1H), 7.92 (t, J 7.6 Hz, 1H), 7.75-7.67 (m, 1H), 7.65 (t, J 9.0 Hz, 1H), 6.98 (s, 1H); Mp: 163-165° C. Data is in accordance with known literature (Menear, K. A., et al., ibid.).

2-Fluoro-5-((4-oxo-3,4,-dihydrophthalazin-1-yl) methyl)benzoic acid

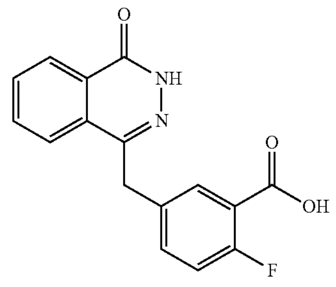 [SMILES: O=C(O)c1cc(Cc2n[nH]c(=O)c3ccccc23)ccc1F]

2-Fluoro-5-[(3'-oxo-2'-benzofuran-1'-ylidene)methyl] benzonitrile (0.50 g, 1.89 mmol) was suspended in water (3 mL) and 13 M NaOH was added (0.67 mL). The mixture was heated to 90° C. and stirred for 24 h, after which it was cooled to 70° C., followed by the addition of hydrazine monohydrate (1.34 mL, 26.9 mmol) and a further 72 h of stirring. The mixture was then cooled to room temperature and acidified with 8 M HCl to an approximate pH of 4. The solid precipitate was collected by vacuum filtration and washed with water (3×25 mL) and $Et_2O$ (4×25 mL) affording 2-Fluoro-5-((4-oxo3,4-dihydrophthalazin-1-yl)methyl) benzoic acid (0.38 g, 67%) as a red solid (Menear, K. A., et al., ibid.).

$^1H$ NMR (400 MHz, DMSO-$d_6$) δ=12.57 (s, 1H), 8.26 (dd, J=7.8, 0.8 Hz, 1H), 7.98 (d, J=7.9 Hz, 1H), 7.93-7.86 (m, 1H), 7.86-7.79 (m, 2H), 7.61-7.54 (m, 1H), 7.23 (dd, J 10.8, 8.5 Hz, 1H), 4.35 (s, 2H); {$^1H$}$^{19}F$ NMR (376 MHz, DMSO-$d_6$) δ=−114.0; Mp: 217-219° C. Data is in accordance with known literature (Menear, K. A., et al., ibid.).

4-(3-(4-(cyclopropanecabonyl)piperazine-1-carbnonyl)-4-fluorobenzyl)phthalazin-1(2H)-one (Olaparib)

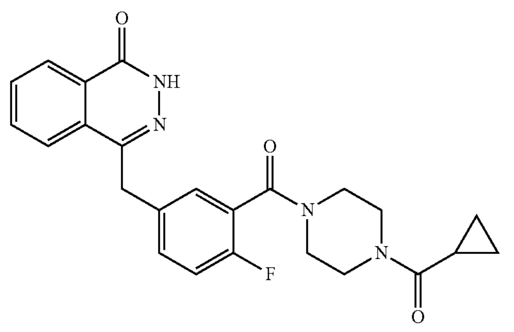 [SMILES: O=C(c1cc(Cc2n[nH]c(=O)c3ccccc23)ccc1F)N1CCN(C(=O)C2CC2)CC1]

To a solution of 2-Fluoro-5-((4-oxo3,4-dihydrophthalazin-1-yl)methyl)benzoic acid (50 mg, 0.168 mmol) in DMA (1 mL) was added DIPEA (56 μL, 0.336 mmol) and HBTU (64 mg, 0.170 mmol). The reaction mixture was stirred for 1 hour before addition of cyclopropylpiperazine-1-ylmethanone (0.170 mmol) was carried out. The reaction mixture was stirred at room temperature for 48 h. The reaction mixture was then extracted with DCM (3×5 mL) and washed with water (3×20 mL). The organic layers were collected, dried with $MgSO_4$ and the excess solvent removed in vacuo. Purification via reverse phase HLPC was carried out affording 4-(3-(4 (cyclopropanecarbonyl) piperazine-1-carbonyl)-4-fluorobenzyl)phthalazin-1(2H)-one (olaparib) (25 mg, 34%) as a white solid.

$^1H$ NMR (400 MHz, $CDCl_3$) δ=10.65 (s, 1H), 8.44-8.37 (m, 1H), 7.75-7.61 (m, 3H), 7.34-7.22 (m, 2H), 6.97 (t, J=8.9 Hz, 1H), 4.22 (s, 2H), 3.90-3.09 (m, 8H), 1.79-1.52 (s, 3H), 0.99-0.88 (m, 2H), 0.81-0.63 (s, 2H); {$^1H$}$^{19}F$ NMR (376 MHz, $CDCl_3$) δ=−117.6; Mp: 69-71° C. Data is in accordance with known literature (Menear, K. A., et al., ibid.).

2-Amino-5-formylbenzonitrile

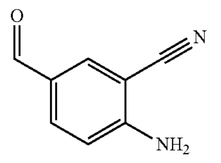 [SMILES: N#Cc1cc(C=O)ccc1N]

To a flame-dried round bottom flask was added 2-amino-5-bromo-benzonitrile (1.00 g, 5.08 mmol) and THE (30 mL). The solution was cooled to −78° C. before n-BuLi in THF (2.5 M, 2.23 mL, 5.59 mmol) was added dropwise. The reaction was left to stir at −78° C. for 2 hours before quenching with DMF (0.55 mL, 7.11 mmol) and allowed to warm to room temperature. The solution was then extracted with $NaHCO_3$ (40 mL) and washed with DCM (3×30 mL). The organic layers were collected, dried with $MgSO_4$, and the excess solvent removed in vacuo. The crude material was then purified via flash column chromatography (n-Pent: EtOAc 4:1) affording 2-amino-5-formylbenzonitrile (0.53 g, 71%) as a pale yellow solid.

$^1H$ NMR (400 MHz, $CDCl_3$) δ=9.76 (s, 1H), 7.92 (d, J=1.8 Hz, 1H), 7.87 (dd, J=8.6, 1.8 Hz, 1H), 6.82 (d, J=8.6 Hz, 1H), 5.00 (bs, 2H); $^{13}C$ NMR (101 MHz, $CDCl_3$) δ=188.6, 153.7, 136.5, 134.3, 127.4, 116.2, 115.1, 95.9. The data is in accordance with known literature (Ravat, P., Borozdina, Y., Ito, Y., Enkelmann, V. & Baumgarten, M. Crystal Engineering of Tolane Bridged Nitronyl Nitroxide Biradicals: Candidates for Quantum Magnets. Cryst. Growth Des. 14, 5840-5846, 2014).

2-Bromo-5-formylbenzonitrile

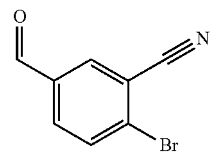 [SMILES: N#Cc1cc(C=O)ccc1Br]

To a round bottom flask containing 2-Amino-5-formylbenzonitrile (17.95 g, 126 mmol) at 0° C. was added 6M HCl (107 mL) and fuming $H_2SO_4$ (107 mL). After being allowed to cool, a solution of sodium nitrite (18.5 g, 268 mmol) in $H_2O$ (40 mL) was added dropwise before allowing the reaction to stir for 30 minutes. The reaction mixture was then added dropwise to a solution of copper(II) bromide (40.1 g, 179 mmol) in 48% HBr (107 mL) at 0° C. The reaction was then stirred at 0° C. for 60 minutes before being allowed to warm to room temperature and being stirred for another hour. Upon completion, the reaction was poured into an ice/water mixture before the organic layer was extracted with DCM (3×150 mL). The organic layer was then dried with $MgSO_4$ and the excess solvent removed in vacuo. The crude material was purified by flash column chromatography (n-Pent:EtOAc 10:1) to afford 2-Bromo-5-formylbenzonitrile as a pale yellow solid (16.8 g, 80.6 mmol, 64%).

$^1H$ NMR (400 MHz, $CDCl_3$) δ=10.00 (s, 1H), 8.14 (s, 1H), 7.95 (d, 8.4, 1H), 7.90 (d, J=8.3 Hz, 1H); $^{13}C$ NMR (101 MHz, $CDCl_3$) δ=188.9, 135.4, 135.1, 134.3, 133.7, 131.9, 117.2, 116.1; IR (ν, $cm^{-1}$): 1702, 1562, 1174, 1008; HRMS (ESI) for $C_8H_5{}^{79}BrNO$ $[M+H]^+$ requires 209.9549 found 209.9551; Mp: 108-110° C.

2-Bromo-5-((3-oxoisobenzofuran-1(3H)-ylidene) methyl)benzonitrile

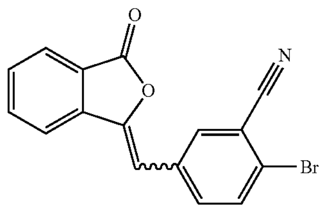 [SMILES: N#Cc1cc(C=C2OC(=O)c3ccccc32)ccc1Br]

A solution of dimethyl-(3-oxo-1,3-dihydrobenzofuran-1-yl)phosphonate (5.00 g, 20.7 mmol) and 2-bromo-5-formylbenzonitrile (3.58 g, 17.2 mmol) in THF (100 mL) was prepared at room temperature. The solution was cooled to 0° C. followed by the addition of $Et_3N$ (4.78 mL, 34.4 mmol). The reaction mixture was warmed to room temperature and was stirred for 48 h, followed by concentration in vacuo to produce a white solid. The solid was suspended in water, collected by vacuum filtration and washed with hexane (2×20 mL) and $Et_2O$ (3×20 mL) affording 2-Bromo-5-((3-oxoisobenzofuran-1(3H)-ylidene)methyl)benzonitrile (5.14 g, 15.8 mmol, 92%) as a white solid in an mixture of e:z stereoisomers (10:1) and a purity of 90%. NMR spectra showed a 10:1 mixture of E and Z isomers.

$^1H$ NMR (400 MHz, DMSO-$d_6$) δ=8.24-8.06 (m, 2H, 2H*), 8.01-7.90 (m, 3H, 3H*), 7.83-7.50 (m, 2H, 2H*), 7.00 (s, 1H*), 6.97 (s, 1H) (Where possible, shifts are assigned to each respective isomer); $^{13}C$ NMR (100 MHz, DMSO-$d_6$) δ=166.3, 146.6, 140.0, 135.9, 135.7, 135.4, 134.3, 134.1, 132.0, 131.6, 125.9, 123.9, 121.5, 117.5, 115.5, 103.9 (only those peaks corresponding to the major isomer are reported); IR (v, $cm^{-1}$): 2980, 1771, 1472, 1394, 970, 760, 689; HRMS (ESI) for $C_{16}H_9{}^{79}BrNO_2$ $[M+H]^+$ requires 325.9746 found 325.9745; Mp: 118-120° C.

2-Bromo-5-((4-oxo-3,4-dihydrophthalazin-1-yl) methyl)benzoic acid

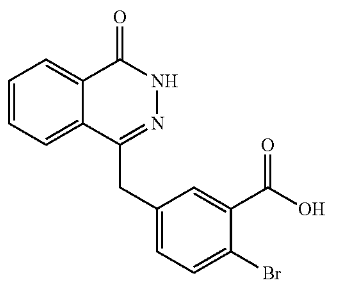

2-Bromo-5-[(3'-oxo-2'-benzofuran-1'-ylidene)methyl] benzonitrile (12.0 g, 36.9 mmol) was suspended in water (75 mL) and 13 M NaOH was added (19 mL, 247 mmol). The mixture was heated to 90° C. and stirred for 24 h, after which it was warmed to reflux (140° C.), followed by the addition of hydrazine monohydrate (25.0 mL, 780 mmol) and a further 48 h of stirring. The mixture was then cooled to room temperature and acidified with 5 M HCl to an approximate pH of 2. The solid precipitate was collected by vacuum filtration and washed with water (50 mL) and $Et_2O$ (3×50 mL) affording 2-Bromo-5-((4-oxo3,4-dihydrophthalazin-1-yl)methyl)benzoic acid (12.27 g, 88%) as a red solid.

$^1H$ NMR (400 MHz, DMSO-$d_6$) δ=12.61 (s, 1H), 8.25 (dd, J=7.7, 1.4 Hz, 1H), 7.99-7.94 (m, 1H), 7.89 (ddd, J=8.1, 7.1, 1.5 Hz, 1H), 7.83 (td, J=7.5, 1.2 Hz, 1H), 7.71 (d, J=2.3 Hz, 1H), 7.62 (d, J=8.2 Hz, 1H), 7.36 (dd, J=8.2, 2.3 Hz, 1H), 4.33 (s, 2H); $^{13}C$ NMR (100 MHz, DMSO-$d_6$) δ=167.7, 159.8, 145.2, 138.5, 134.3, 134.1, 133.4, 132.1, 131.4, 129.5, 128.3, 126.5, 125.9, 118.4, 100.0, 36.9; IR (v, $cm^{-1}$): 2890, 1771, 1472, 1394, 970, 760, 689; HRMS (ESI) for $C_{16}H_{10}{}^{79}BrN_2O_3$ $[M-H]^-$ requires 356.9945 found 356.9948; Mp: >250° C.

Methyl-2-bromo-5-((4-oxo-3,4-dihydrophthalazin-1-yl)methyl)benzoate

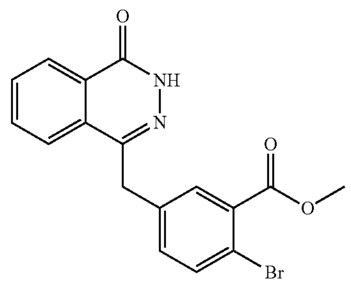 [SMILES: COC(=O)c1cc(Cc2n[nH]c(=O)c3ccccc23)ccc1Br]

To a solution of 2-Bromo-5-((4-oxo-3,4,-dihydrophthalazin-1-yl)methyl)benzoic acid (12.32 g, 34.4 mmol) in anhydrous DMF (100 mL) was added iodomethane (6.38 mL, 103.2 mmol) and anhydrous potassium carbonate (5.70 g, 41.3 mmol). The reaction was then heated to 50° C. and stirred overnight. Upon completion, the excess solvent was removed in vacuo and water (100 mL) was added to the crude material. The precipitate formed was filtered and washed with $Et_2O$ (3×100 mL) before drying in vacuo affording Methyl-2-bromo-5-((4-oxo-3,4-dihydrophthalazin-1-yl)methyl) benzoate as a dull brown solid (11.4 g, 30.6 mmol, 89%).

$^1H$ NMR (400 MHz, DMSO-$d_6$) δ=12.60 (s, 1H), 7.99-7.93 (m, 1H), 7.90 (ddd, J=8.1, 7.1, 1.5 Hz, 1H), 7.83 (ddd, J=8.4, 7.2, 1.3 Hz, 1H), 7.73 (d, J=2.2 Hz, 1H), 7.67 (d, J=8.2 Hz, 1H), 4.35 (s, 2H), 3.83 (s, 3H); $^{13}C$ NMR (100 MHz, DMSO-$d_6$) δ=166.6, 159.8, 145.1, 138.6, 134.4, 134.1, 134.0, 132.8, 132.1, 131.6, 129.5, 128.3, 126.5, 125.9, 118.5, 53.1, 36.9; IR (v, $cm^{-1}$): 2983, 1650, 1250, 1205, 1104, 772; HRMS (ESI) for $C_{17}H_{13}{}^{79}BrN_2{}^{23}NaO_3$ [M+Na] requires 395.0002 found 395.0001; Mp: 211-213° C.

Methyl-2-bromo-5-((4-oxo-((2-(trimethylzilyl) ethoxy)methyl)-3,4-dihydro phthalazin-1-yl)methyl) benzoate

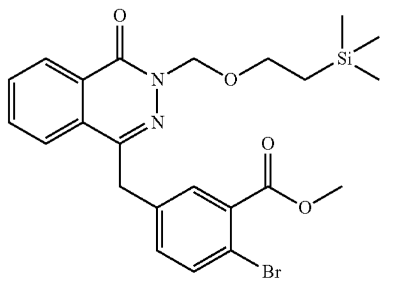 [SMILES: COC(=O)c1cc(Cc2nn(COCC[Si](C)(C)C)c(=O)c3ccccc23)ccc1Br]

To a round bottom flask under an atmosphere of argon containing Methyl-2-bromo-5-((4-oxo-((2-(trimethylzilyl) ethoxy)methyl)-3,4-dihydro phthalazin-1-yl)methyl) benzoate (11.0 g, 29.6 mmol) at 0° C. was added anhydrous THF (200 mL) and sodium hydride (60% in dispersion oil, 3.55 g, 88.8 mmol). The reaction was stirred at 0° C. for 30 min before warming to room temperature upon which 2-(trimethylsilyl)ethoxymethyl chloride (6.25 mL, 35.6 mmol) was added dropwise. The reaction was stirred overnight before the excess solvent was removed in vacuo and purified directly via flash column chromatography (n-Pent:EtOAc 10:3) affording Methyl-2-bromo-5-((4-oxo-((2-(trimethylzilyl)ethoxy)methyl)-3,4-dihydro phthalazine-1-yl)methyl) benzoate as a white solid (10.7 g, 72%, 21.3 mmol).

$^{1}$H NMR (400 MHz, $CDCl_3$) δ=8.52-8.45 (m, 1H), 7.77-7.68 (m, 3H), 7.66-7.58 (m, 1H), 5.58 (s, 2H), 4.28 (s, 2H), 3.91 (s, 3H), 3.79-3.73 (m, 2H), 1.02-0.97 (m, 2H), 0.01 (s, 9H); $^{13}$C NMR (100 MHz, $CDCl_3$) δ=167.8, 161.3, 145.7, 138.6, 136.0, 134.9, 133.9, 133.8, 133.0, 132.6, 130.5, 129.8, 129.2, 126.3, 121.3, 80.4, 68.6, 54.0, 39.5, 19.5, 0.00 (3C); IR (v, $cm^{-1}$): 2952, 1721, 1652, 1431, 1294, 1223, 1074, 1027, 854, 832, 745; HRMS (ESI) for $C_{23}H_{27}{}^{79}BrN_2{}^{23}NaO_4{}^{28}Si$ $[M+Na]^+$ requires 525.0826 found 525.0827; Mp: 85-87° C.

4-(3-(4-(cyclopropanecarbonyl)piperazine-1-carbonyl)-4-(4,4,5,5-tetramethyl-1,3,2-dioxaborolan-2-yl) benzyl)-2-((2-trimethlsilyl)ethoxy)methyl)phthalazin-1(2H)-one

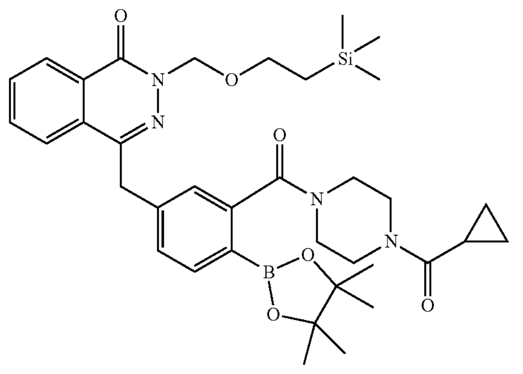 [SMILES: CC1(C)OB(c2ccc(Cc3nn(COCC[Si](C)(C)C)c(=O)c4ccccc34)cc2C(=O)N2CCN(C(=O)C3CC3)CC2)OC1(C)C]

To a Schlenk tube under an atmosphere of argon was added, Methyl-2-bromo-5-((4-oxo-((2-(trimethylsilyl) ethoxy) methyl)-3,4-dihydro phthalazin-1-yl)methyl)benzoate (1.48 g, 2.94 mmol), bis(pinacolato)diboron (1.49 g, 5.89 mmol), $Pd(dppf)Cl_2$ (72 mg, 0.09 mmol) and potassium acetate (0.87 g, 8.88 mmol). The reaction flask was then backfilled with argon and placed in an oil bath at 90° C. upon which degassed DMF (13 mL) was added and the reaction left to stir overnight. Upon completion, the reaction was cooled and passed through a plug of Celite before extracting with EtOAc (100 mL) and washing with Lithium Chloride solution (3×50 mL). The organic phases were then collected and the excess solvent was removed in vacuo. The crude material was then purified by flash column chromatography (10:3 n-Pent: EtOAc) to afford a mixture of Methyl-5-((4-oxo-3-((2-(trimethylsilyl)ethoxy)methyl)-3,4-dihydro phthalazin-1-yl)methyl)-2-(4,4,5,5-tetramethyl-1,3,2-dioxaborolan-2-yl)benzoate and bis(pinacolato)diboron (2.00 g) with the following $^{1}$H NMR spectra being observed.

$^{1}$H NMR (400 MHz, $CDCl_3$) δ=8.43 (d, J=7.8 Hz, 1H), 7.85 (s, 1H), 7.76-7.57 (m, 2H), 7.53 (d, J=8.0 Hz, 1H), 7.38 (s, 2H), 5.58 (s, 2H), 4.32 (s, 2H), 3.86 (s, 3H), 3.76 (t, J=7.3 Hz, 1H), 0.99 (t, J=7.6 Hz, 2H), −0.03 (s, 9H). Peaks reported only correspond to the product. The crude material was taken forward without further purification.

To a round bottom flask containing Methyl-5-((4-oxo-3-((2-(trimethylsilyl)ethoxy) methyl)-3,4-dihydrophthalazin-1-yl) methyl)-2-(4,4,5,5-tetramethyl-1,3,2-dioxa borolan-2-yl)benzoate and bis(pinacolato) diboron (2.00 g) was added THF (100 mL) before cooling to 0° C. Upon cooling, 2M lithium hydroxide (7 mL, 14 mmol) was added dropwise before allowing to reaction to stir for 30 minutes at 0° C. 1M HCl was then added dropwise to the reaction mixture at 0° C. until reaching pH 4. The mixture was then extracted with EtOAc (3×80 mL) and washed with Brine (3×50 mL). The organic phases were combined and the excess solvent removed in vacuo. The crude material (1.4 g) was transferred to a round bottom flask upon which DCM (100 mL), HBTU (2.97 g, 7.84 mmol) and DIPEA (1.36 mL, 7.84 mmol) was added. After stirring at room temperature for 30 minutes, N-cyclopropylcarbonylpiperazine (1.11 mL, 7.85 mmol) was added and the reaction stirred overnight. After stirring for 16 hours, the excess solvent was removed in vacuo and the crude material isolated by flash column chromatography (Pure EtOAc) before purification by reverse phase HPLC was carried out to afford 4-(3-(4-(cyclopropanecarbonyl) piperazine-1-carbonyl)-4-(4,4,5,5-tetramethyl-1,3,2-dioxaborolan-2-yl)benzyl)-2-((2-trimethlsilyl) ethoxy)methyl)phthalazin-1(2H)-one (419 mg, 0.62 mmol, 22%—three steps) as a white solid in a mixture of rotamers. In each case the shift relating to the minor rotamer has been donated with an asterisk.*

$^{1}$H NMR (400 MHz, $CDCl_3$) δ=8.46 (dd, J=7.8, 1.6 Hz, 1H+1H*), 7.79-7.55 (m, 4H+4H*), 7.32-7.28 (m, 1H+1H*), 7.14 (bs, 1H+1H*), 5.59 (s, 2H+2H*), 4.33 (s, 2H+2H*), 3.87-3.04 (m, 10H+10H*), 1.28 (s, 12H+12H*), 1.04-0.97 (m, 4H+4H*), 0.90-0.85 (m, 1H+1H*), 0.83-0.71 (m, 2H+2H*), 0.00 (s, 9H+9H*); $^{13}$C NMR (100 MHz, $CDCl_3$) δ=172.3 (1C+1C*), 171.0 (1C+1C*), 160.0 (1C+1C*), 144.7 (1C+1C*), 142.9 (1C+1C*), 141.3 (1C+1C*), 136.3 (1C+1C*), 133.3 (1C+1C*), 131.5 (1C+1C*), 129.2 (1C+1C*), 128.4 (1C+1C*), 128.2 (1C+1C*), 127.7 (1C+1C*), 125.4 (1C+1C*), 125.2 (1C+1C*), 84.1 (2C+2C*), 79.0 (1C+1C*), 67.3 (1C+1C*), 47.3 (1C*), 46.9 (1C), 45.2 (1C*), 44.8 (1C), 41.9 (1C*), 41.7 (2C), 41.4 (1C*), 39.1 (1C+1C*), 24.9 (4C+4C*), 18.1 (1C+1C*), 11.1 (1C+1C*), 7.66 (2C+2C*), −1.36 (3C+3C*) (the carbon bearing the boron substituent is not observed); IR (v, $cm^{-1}$): 2981, 2889, 2360, 2341, 1641, 1382, 1354, 1146, 1087, 956; HRMS (ESI) for $C_{36}H_{49}N_4O_6{}^{10}B^{23}Na^{28}Si$ $[M+Na]^+$ requires 694.34429 found 694.34418; Mp: 78-80° C.

2-Methylphthalazin-1(2H)-one

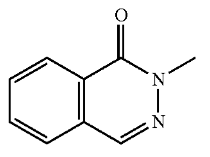

To a round bottom flask containing DMF (10 mL) under an atmosphere of argon was added, phthalazone (300 mg, 2.05 mmol). To solution was then cooled to 0° C. before sodium hydride (60% in dispersion oil, 61 mg, 2.53 mmol) was added portion wise. iodomethane (119 μL, 1.92 mmol). The reaction was stirred overnight before the solvent was removed in vacuo and the crude material purified directly via flash column chromatography using n-pentane:EtOAc (10:1) affording 2-2-Methylphthalazin-1(2H)-one as a white solid (210 mg, 1.31 mmol, 64%).

$^1H$ NMR (400 MHz, $CDCl_3$) δ=8.42-8.38 (m, 1H), 8.12 (s, 1H), 7.81-7.70 (m, 2H), 7.69-7.65 (m, 1H), 3.83 (s, 3H); $^{13}C$ NMR (100 MHz, $CDCl_3$) δ=159.7, 137.6, 133.0, 131.6, 129.8, 127.8, 126.5, 126.0, 39.5. The data is in accordance with known literature (Outerbridge, V. M., Landge, S. M., Tamaki, H. & Török, B. Microwave-Promoted Solid-Acid Catalyzed One-Pot Synthesis of Phthalazinones. Synthesis 11, 1801-1806, 2009).

tert-Butyl 1-oxophthalazine-2(1H)-carboxylate

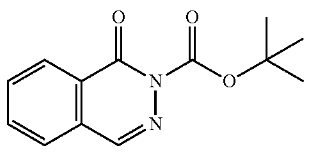 [SMILES: CC(C)(C)OC(=O)n1ncc2ccccc2c1=O]

To a round bottom flask containing THF (10 mL) under an atmosphere of nitrogen was added, phthalazone (500 mg, 3.41 mmol), di-tert-butyl dicarbonate (1.11 g, 5.12 mmol) and DMAP (620 mg, 5.12 mmol). The reaction was stirred overnight at room temperature before the solvent was removed in vacuo and the crude material purified directly via flash column chromatography using n-pentane:EtOAc (5:1) tert-Butyl 1-oxophthalazine-2(1H)-carboxylate as a white solid (765 mg, 3.11 mmol, 91%).

$^1H$ NMR (400 MHz, $CDCl_3$) δ=8.43 (dd, J=7.9, 1.3 Hz, 1H), 7.83 (td, J=7.5, 1.4 Hz, 1H), 7.77 (td, J=7.6, 1.3 Hz, 1H), 7.68 (dd, J=7.5, 1.3 Hz, 1H), 1.66 (s, 9H); $^{13}C$ NMR (100 MHz, $CDCl_3$) δ=158.3, 150.9, 138.9, 134.2, 132.3, 129.2, 128.7, 127.5, 126.4, 85.9, 27.8 (3C); IR (v, $cm^{-1}$): 2980, 1720, 1641, 1470, 1325, 1130; HRMS (ESI) for $C_{13}H_{14}N_2O_3$ $[M+H]^+$ requires 247.1012 found 247.1015; Mp: 81-83° C.

2-allylphthalazin-1(2H)-one

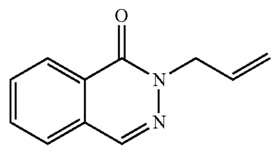

To a round bottom flask containing DMF (30 mL) under an atmosphere of nitrogen was added, phthalazone (500 mg, 3.42 mmol), anhydrous potassium carbonate (708 mg, 5.12 mmol) and allyl bromide (442 μL, 5.12 mmol). The reaction was stirred overnight at room temperature before the solvent was removed in vacuo and the crude material purified directly via flash column chromatography using n-pentane: EtOAc (3:1) affording 2-allylphthalazin-1(2H)-one as a brown oil (222 mg, 1.20 mmol, 35%)

$^1H$ NMR (400 MHz, $CDCl_3$) δ=8.42 (ddd, J=7.5, 1.7, 0.7 Hz, 1H), 8.17 (d, J=0.8 Hz, 1H), 7.83-7.72 (m, 2H), 7.71-7.67 (m, 1H), 6.04 (ddt, J=17.2, 10.3, 5.9 Hz, 1H), 5.30-5.22 (m, 2H), 4.85 (dt, J=5.9, 1.5 Hz, 2H); $^{13}C$ NMR (100 MHz, $CDCl_3$) δ=159.2, 138.1, 133.1, 132.5, 131.7, 129.7, 128.0, 126.8, 126.0, 118.0, 53.5. Data is in accordance with literature values (Nezhawy, A. O. H., Gaballah, S. T. & Radwan, M. A. A. Studying the reactivity of (phthalazin-1(2H)-on-2-yl)methyl trichloroacetimidate towards different C- and O-nucleophiles. Tetrahedron Letters 50, 6646-6650, 2009).

2-((2-trimethylsilyl)ethoxyl)methyl)phthalazin-1 (2H)-one

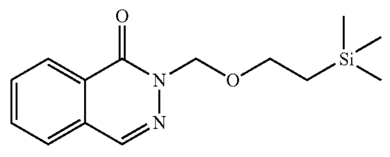 [SMILES: C[Si](C)(C)CCOCn1ncc2ccccc2c1=O]

To a round bottom flask containing THF (10 mL) under an atmosphere of argon was added, phthalazone (480 mg, 3.28 mmol). To solution was then cooled to 0° C. before sodium hydride (60% in dispersion oil, 97 mg, 4.04 mmol) was added portion wise. The reaction was then stirred for 30 minutes at 0° C. before warming to room temperature after which 2-(trimethylsilyl)ethoxymethyl chloride (0.70 mL, 3.97 mmol mmol) was added dropwise. The reaction mixture was left to stir overnight after which the solvent was removed in vacuo. The crude mixture was then extracted with DCM (3×10 mL) and washed with brine (3×10 mL). The organic layer was collected, dried with magnesium sulfate and the excess solvent removed in vacuo. The crude material was then purified by flash column chromatography (2:3 n-Pent:EtOAc) to afford 2-((2-trimethylsilyl)ethoxyl) methyl) phthalazin-1(2H)-one as a colourless oil (435 mg, 1.57 mmol, 46%).

$^1H$ NMR (400 MHz, $CDCl_3$) δ=8.41 (d, J=7.8 Hz, 1H), 8.15 (s, 1H), 7.76 (dt, J=21.7, 7.6 Hz, 2H), 7.67 (d, J=7.7 Hz, 1H), 5.55 (s, 2H), 3.74-3.68 (m, 2H), 0.99-0.92 (m, 2H), −0.05 (s, 9H); $^{13}C$ NMR (100 MHz, $CDCl_3$) δ=161.4, 139.6, 134.9, 133.2, 131.2, 129.4, 128.4, 127.6, 80.4, 68.5, 19.5, 0.00 (3C); IR (v, $cm^{-1}$): 1661, 1081, 833, 758; HRMS (ESI) for $C_{14}H_{20}N_2{}^{23}NaO_2{}^{28}Si$ $[M+Na]^+$ requires 299.1186 found 299.1185.

2-(4,4,5,5-Tetramethyl-1,3,2-dioxaborolan-2-yl)benzoic acid

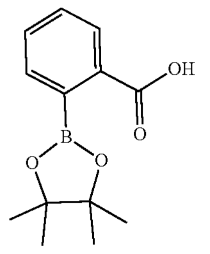 [SMILES: CC1(C)OB(c2ccccc2C(=O)O)OC1(C)C]

To a solution of anhydrous THF (20 mL) under an atmosphere of argon was added 2-boronobenzoic acid (1.00 g, 6.02 mmol), pinacol (0.71 g, 6.02 mmol) and magnesium sulfate (1.44 g, 12.04 mmol). The reaction was left to stir overnight at room temperature. Upon completion, the reaction was filtered and the excess solvent removed in vacuo affording 2-(4,4,5,5-Tetramethyl-1,3,2-dioxaborolan-2-yl) benzoic acid as a white solid (1.49 g, 6.00 mmol, 99%).

$^1H$ NMR (400 MHz, DMSO-$d_6$) δ=7.83 (dd, J=7.6, 0.9 Hz, 1H), 7.55 (td, J=7.3, 1.3 Hz, 1H), 7.46 (td, J=7.5, 1.4, 1H), 7.43-7.39 (m, 1H), 1.29 (s, 12H); $^{13}C$ NMR (100 MHz, DMSO-$d_6$) δ=169.6, 134.7, 132.2, 131.9, 129.2, 128.3, 83.4 (2C), 25.0 (4C) (the carbon bearing the boron substituent is not observed); IR (v, $cm^{-1}$): 2972, 1679, 1344, 1304, 1141, 754; HRMS (ESI) for $C_{13}H_{16}{}^{10}BO_4$ $[M-H]^-$ requires 247.1212 found 247.1215; Mp: 118-120° C.

(4-(Cyclopropanecarbonyl)piperazin-1-yl)(2-(4,4,5,5-tetramethyl-1,3,2-dioxaborolan-2-yl)phenyl)methanone

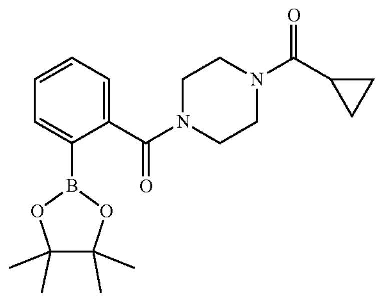 [SMILES: CC1(C)OB(c2ccccc2C(=O)N2CCN(C(=O)C3CC3)CC2)OC1(C)C]

To a round bottom flask containing 2-(4,4,5,5-Tetramethyl-1,3,2-dioxaborolan-2-yl)benzoic acid (1.00 g, 4.03 mmol) was added DCM (40 mL), diisopropylethylamine (1.05 mL, 6.04 mmol) and HBTU (2.29 g, 6.04 mmol). The reaction mixture was stirred for 30 min before adding cyclopropylpiperazine-1-ylmethanone (0.86 mL, 6.04 mmol). The reaction was stirred overnight before the excess solvent with removed in vacuo and the crude material purified via flash column chromatography (EtOAc:MeOH 10:1) affording (4-(Cyclopropanecarbonyl)piperazin-1-yl) (2-(4,4,5,5-tetramethyl-1,3,2-dioxaborolan-2-yl)phenyl) methanone as a white solid (1.08 g, 2.82 mmol, 70%) in a mixture of rotamers (2:1). The shifts relating to the minor rotamer has been donated with an asterisk.*

$^1H$ NMR (400 MHz, $CDCl_3$) δ=7.81 (d, J=7.4 Hz, 1H+1H*), 7.45 (td, J=7.6, 1.5 Hz, 1H+1H*), 7.35 (td, J=7.5, 1.3 Hz, 1H+1H*), 7.22 (d, J=7.5 Hz, 1H+1H*), 3.86-3.69 (m, 4H, 4H*), 3.67-3.50 (m, 2H, 2H*), 3.34-3.07 (m, 2H, 2H*), 1.81-1.52 (m, 1H+1H*), 1.29 (s, 12H+12H*), 1.04-0.95 (m, 2H+2H*), 0.67-0.87 (m, 2H+2H*); $^{13}C$ NMR (100 MHz, $CDCl_3$) δ=172.3 (1C+1C*), 171.3 (1C+1C*), 142.3 (1C+1C*), 135.7 (1C+1C*), 131.2 (1C+1C*), 128.2 (1C+1C*), 125.4 (1C+1C*), 84.1 (2C+2C*), 47.3 (1C*), 47.0, 45.2 (1C*), 44.9, 41.9 (2C), 41.6 (2C*) 24.9 (4C+4C*), 11.0 (1C+1C*), 7.65 (2C+2C*) (the carbon bearing the boron substituent is not observed); IR (v, $cm^{-1}$): 2970, 1634, 1467, 1213, 1014, 741; HRMS (ESI) for $C_{21}H_{30}{}^{10}BN_2O_4[M+H]^+$ requires 384.2220 found 384.2218; Mp: 85-87° C.

(4-(Cyclopropanecarbonyl)piperazin-1-yl)(2-fluorophenyl)methanone

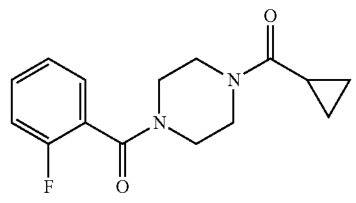 [SMILES: O=C(c1ccccc1F)N1CCN(C(=O)C2CC2)CC1]

To a round bottom flask was added, 2-fluorobenzoic acid (1.00 g, 7.14 mmol), DCM (40 mL), diisopropylethylamine (1.86 mL, 10.7 mmol) and HBTU (4.06 g, 10.7 mmol). The reaction mixture was then stirred for 30 minutes at room temperature before adding cyclopropylpiperazine-1-yl-methanone (1.52 mL, 10.7 mmol). The reaction was stirred overnight before the excess solvent with removed in vacuo and the crude material purified via flash column chromatography (EtOAc:MeOH 10:1) affording (4-(Cyclopropanecarbonyl)piperazin-1-yl)(2-(4,4,5,5-tetramethyl-1,3,2-dioxaborolan-2-yl)phenyl)methanone as a white solid (1.32 g, 4.78 mmol 67%) in a mixture of rotamers (2:1). In each case the shift relating to the minor rotamer has been donated with an asterisk.*

$^1H$ NMR (400 MHz, $CDCl_3$) δ=7.40-7.29 (m, 2H+2H*), 7.16 (td, J=7.5, 1.1 Hz, 1H+1H*), 7.04 (ddd, J=9.4, 8.3, 1.1 Hz, 1H+1H*), 3.88-3.46 (m, 6H+6H*), 3.38-3.20 (m, 2H+2H*), 1.76-1.58 (m, 1H+1H*), 0.98-0.88 (m, 2H+2H*), 0.83-0.62 (m, 2H+2H*); $^{13}C$ NMR (100 MHz, $CDCl_3$) δ=172.3 (1C+1C*), 165.4 (1C+1C*), 158.0 (d, J=247.7 Hz, 1C+1C*), 131.7 (d, J=8.0 Hz, 1C+1C*), 129.1 (1C+1C*), 124.9 (d, J=3.5 Hz, 1C+1C*), 123.5 (d, J=17.4, 1C+1C*), 115.8 (d, J=21.3, 1C+1C*), 47.0 (1C*), 46.7 (1C), 45.6 (1C*), 45.1 (1C), 42.2 (2C), 41.9 (1C*), 41.7 (1C*), 11.0 (1C+1C*), 7.64 (2C+2C*); $\{^1H\}^{19}F$ NMR (376 MHz, $CDCl_3$) δ=−115.0 (s, 1F*), −115.1 (s, 1F); IR (v, $cm^{-1}$): 1630, 1460, 1219, 1004, 727; HRMS (ESI) for $C_{15}H_{18}{}^{19}FN_2O_2$ $[M+H]^+$ requires 277.1282 found 277.1285; Mp: 65-67° C.

3-((4-oxo-3,4-dihydrophthalazin-1-yl)methyl)benzoic acid

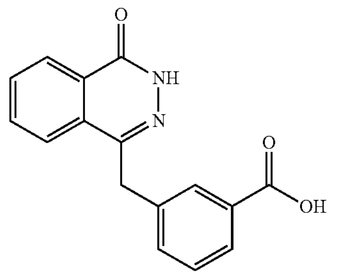 [SMILES: O=C(O)c1cccc(Cc2n[nH]c(=O)c3ccccc23)c1]

A solution of Dimethyl-(3-oxo-1,3-dihydrobenzofuran-1-yl)phosphonate (7.25 g, 30.0 mmol) and 3-formylbenzonitrile (2.62 g, 20.0 mmol) in THF (250 mL) was prepared at room temperature. The solution was then cooled to 0° C. followed by the addition of $Et_3N$ (6.10 mL, 30.0 mmol). The reaction mixture was warmed to room temperature and was stirred for 48 h, followed by concentration in vacuo to produce a white solid. The solid was suspended in water, collected by vacuum filtration and washed with hexane (2×20 mL) and $Et_2O$ (3×20 mL) affording 3-((3-oxoisobenzofuran-1(3H)-ylidene)methyl)benzonitrile (4.40 g) as a crude white solid which was then taken through to the next step without further purification. 3-((3-oxoisobenzofuran-1(3H)-ylidene)methyl)benzonitrile (4.40 g, 17.8 mmol) was suspended in water (100 mL) and 13 M NaOH was added (26.4 mL, 238 mmol). The mixture was heated to 90° C. and stirred for 2 h, after which it was warmed to reflux (140° C.), followed by the addition of hydrazine monohydrate (7.48 mL, 240 mmol) and a further 16 h of stirring. The mixture was then cooled to room temperature and acidified with 5 M HCl to an approximate pH of 2. The solid precipitate was collected by vacuum filtration and washed with water (100 mL) and $Et_2O$ (3×100 mL) affording 3-((4-oxo-3,4-dihydrophthalazin-1-yl)methyl)benzoic acid (4.18 g, 15.0 mmol, 50%, two steps) as a white solid.

$^1$H NMR (400 MHz, DMSO-$d_6$) δ=12.64 (s, 1H), 8.25 (dd, J=7.9, 1.4 Hz, 1H), 7.96 (d, J=7.9 Hz, 1H), 7.91-7.85 (m, 2H), 7.82 (dd, J=7.6, 1.2 Hz, 1H), 7.80-7.75 (m, 1H), 7.58 (dt, J=7.7, 1.5 Hz, 1H), 7.42 (t, J=7.7 Hz, 1H), 4.38 (s, 2H); $^{13}$C NMR (100 MHz, DMSO-$d_6$) δ=167.6, 159.8, 145.5, 139.1, 134.0, 133.7, 132.0, 131.4, 129.8, 129.5, 129.3, 128.3, 127.9, 126.5, 126.0; IR (v, $cm^{-1}$): 3004, 1686, 1457, 1270, 1082, 937, 762, 666; HRMS (ESI) for $C_{16}H_{11}N_2O_3$ $[M-H]^-$ requires 279.0840 found 279.0647; Mp: >250° C.

4-(3-(4-(cyclopropanecabonyl)piperazine-1-carbnonyl)benzyl)phthalazin-1(2H)-one

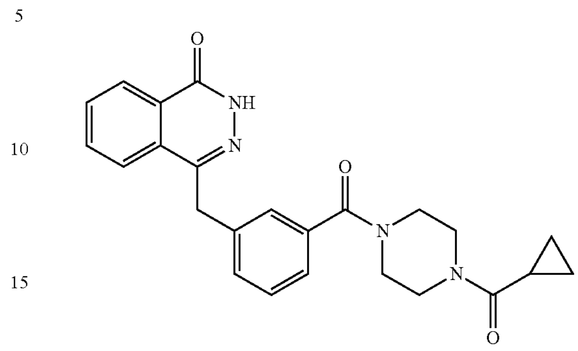

To a solution of 3-((4-oxo-3,4-dihydrophthalazin-1-yl)methyl)benzoic acid (1.00 g, 3.57 mmol) in DCM (100 mL) was added DIPEA (930 μL, 5.36 mmol) and HBTU (2.63 g, 5.36 mmol). The reaction mixture was stirred for 1 h before addition of cyclopropylpiperazine-1-ylmethanone (760 μL, 5.36 mmol) was carried out. The reaction mixture was then stirred at room temperature for 48 h, and the reaction mixture was extracted with DCM (3×50 mL) and washed with water (3×50 mL). The organic layers were collected, dried with $MgSO_4$ and the excess solvent removed in vacuo. Purification via reverse phase HLPC was then carried out affording 4-(3-(4-(cyclopropanecabonyl)piperazine-1-carbnonyl)benzyl)phthalazin-1(2H)-one (810 mg, 55%) as a white solid.

$^1$H NMR (400 MHz, $CDCl_3$) δ=11.83 (bs, 1H), 8.46-8.39 (m, 1H), 7.73-7.67 (m, 3H), 7.37-7.30 (m, 3H), 7.27-7.20 (m, 1H), 4.33 (s, 2H), 3.89-3.18 (m, 8H), 1.78-1.60 (m, 1H), 1.00-0.90 (m, 2H), 0.82-0.64 (m, 2H); $^{13}$C NMR (100 MHz, $CDCl_3$) δ=172.4, 170.4, 161.1, 145.7, 138.3, 135.5, 133.5, 131.5, 130.2, 129.6, 129.0, 128.2, 127.2, 127.0, 125.5, 125.1, 47.5, 45.3, 42.3 (2C), 38.5, 14.2, 11.0, 7.73; IR (v, $cm^{-1}$): 2925, 1632, 1430, 1353, 1101, 772; HRMS (ESI) for $C_{24}H_{25}N_4O_3$ $[M+H]^+$ requires 417.1856 found 417.2001; Mp: 82-84° C.

Synthesis of $[Cu(OTf)_2(Impy)_4]$ Complex

A solution of imidazo[1,2-b]pyridazine (impy) (758 mg, 6.36 mmol, 10 equiv.) in MeOH (1 mL) was added dropwise at 55° C. to a solution of $Cu(OTf)_2$ (230 mg, 0.636 mmol, 1.0 equiv.) in MeOH (1 mL). The blue precipitate which formed was washed with $Et_2O$ (3×2 mL), then recrystallized from hot MeOH to afford $[Cu(OTf)_2(impy)_4]$(324 mg, 0.387 mmol, 61%).

Anal. Calcd. for $C_{26}H_{20}CuF_6N_{12}O_6S_2$: C, 37.26; H, 2.41; N, 20.05. Found: C, 37.07; H, 2.33; N, 19.91; IR (ATR, neat): v ($cm^{-1}$)=2981, 1620, 1541, 1503, 1374, 1352, 1306, 1281, 1241, 1221, 1149, 1071, 1027, 950, 918, 879, 801, 755, 733, 632.

Boronic Ester Transformations

Bpin—$BF_3K$: Typical Conditions

To a stirred solution of boronic ester in methanol was added $KHF_2$ at ambient temperature and the reaction mixture was stirred. All volatile materials were removed on a rotary evaporator. The residue was re-dissolved in MeOH and all volatile materials were evaporated again. The solid residue was then triturated with dry acetone, the liquid phase was carefully decanted, and the residual inorganic salts were washed with additional acetone. The combined washings were collected and concentrated in vacuo to give the desired trifluoroborate as a colourless crystalline or amorphous solid.

Methyl-5-((4-oxo-3-((2-(trimethylsilyl)ethoxy) methyl)-3,4-dihydrophthalazin-1-yl)methyl)-2-(trifluoro-λ4-boraneyl)benzoate, potassium salt

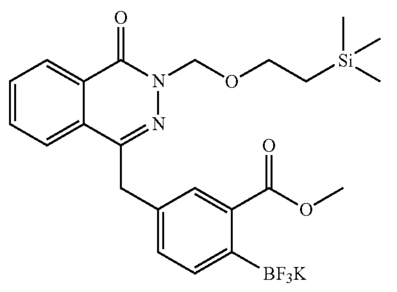

To a Schlenk tube under an atmosphere of argon was added, Methyl-2-bromo-5-((4-oxo-((2-(trimethylsilyl) ethoxy) methyl)-3,4-dihydro phthalazin-1-yl)methyl)benzoate (1.48 g, 2.94 mmol), bis(pinacolato)diboron (1.49 g, 5.89 mmol), $Pd(dppf)Cl_2$ (72 mg, 0.09 mmol) and potassium acetate (0.87 g, 8.88 mmol). The reaction flask was then backfilled with argon and placed in an oil bath at 90° C. upon which degassed DMF (13 mL) was added and the reaction left to stir overnight. Upon completion, the reaction was cooled and passed through a plug of Celite before extracting with EtOAc (100 mL) and washing with Lithium Chloride solution (3×50 mL). The organic phases were then collected and the excess solvent was removed in vacuo. The crude material was then purified by flash column chromatography (10:3 n-Pent:EtOAc) to afford a mixture of Methyl-5-((4-oxo-3-((2-(trimethylsilyl)ethoxy)methyl)-3,4-dihydro phthalazin-1-yl)methyl)-2-(4,4,5,5-tetramethyl-1,3,2-dioxaborolan-2-yl)benzoate and bis(pinacolato)diboron (2.00 g) with the following $^1H$ NMR spectra being observed.

To a round bottom flask containing a crude mixture of methyl-5-((4-oxo-3-((2-(trimethylsilyl)ethoxy)methyl)-3,4-dihydrophthalazin-1-yl)methyl)-2-(4,4,5,5-tetramethyl-1,3,2-dioxaborolan-2-yl)benzoate and bispinacolatodiboron (2.00 g) was added 1:1 $MeOH:H_2O$ (40 mL) and potassium bifluoride (2.26 g, 29.0 mmol). The reaction was stirred at room temperature overnight before the MeOH was removed in vacuo leading to precipitation. The precipitate was filtered and dried in vacuo affording Methyl-5-((4-oxo-3-((2-(trimethylsilyl)ethoxy)methyl)-3,4-dihydrophthalazin-1-yl) methyl)-2-(trifluoro-λ4-boraneyl)benzoate, potassium salt as a white solid (1.09 g, 2.06 mmol, 70%).

Mp: 203-205° C.; $^1H$ NMR (400 MHz, $CDCl_3$) δ 8.30 (d, J=7.8, 1H), 7.96-7.77 (m, 3H), 7.36 (d, J=7.5 Hz, 1H), 7.23-7.07 (m, 2H), 5.47 (s, 2H), 4.25 (s, 2H), 3.72 (t, J=7.9 Hz, 2H), 3.62 (s, 3H), 0.90 (t, J=7.9 Hz, 2H), −0.05 (s, 9H); $^{13}C$ NMR (100 MHz, $CDCl_3$) δ=172.9, 159.8, 146.1, 137.8, 135.2, 134.6, 134.0, 134.0, 132.7, 129.6, 129.1, 128.4, 127.5, 126.9, 126.3, 79.3, 66.9, 52.1, 38.4, 18.3, −0.05; $^{19}F$ NMR (376 MHz, $CDCl_3$) δ=−137.4 (s, 3F); IR (v, $cm^{-1}$): 1722, 1669, 1590, 1283, 1085, 891, 791, 682; HRMS (ESI) for $C_{23}H_{27}{}^{10}BF_3N_2O_4{}^{28}Si$ $[M-K]^-$ requires 491.1785 found 491.1779.

Bpin—$B(OH)_2$: Typical Conditions

To an aryl pinacol ester (1.00 equiv) in acetone/$H_2O$ was added $NH_4OAc$ (5.00 equiv) and $NaIO_4$ (5.00 equiv). After stirring for 48 hr at room temperature, the reaction mixture was concentrated in vacuo to remove acetone. To the residual solution was added EtOAc and the phases were separated. The aqueous phase was extracted with EtOAc. The combined organic phases were washed with brine and dried ($Na_2SO_4$). The filtrate was concentrated in vacuo and the residue was triturated with $Et_2O$ to afford the desired product.

REFERENCES FOR BORONIC ESTER TRANSFORMATIONS

J. M. Murphy, C. C. Tzschucke, J. F. Hartwig, Org. Lett., 2007, 9, 757-760.

T. Furuya, T. Ritter Org. Lett., 2009, 11, 2860-2863.

3. Radiochemical Synthesis Methods

Radiochemistry:

$^{18}F$-Fluoride was produced by Alliance Medical (UK) via the $^{18}O(p,n)^{18}F$ reaction and delivered as $^{18}F$-fluoride in $^{18}O$-enriched-water. Radiosynthesis and azeotropic drying was performed on a NanoTek microfluidic device (Advion).

Procedure for Preparation of a Solution of $[^{18}F]KF/K_{222}$ in MeCN

A solution of Kryptofix 222 (15 mg) and $K_2CO_3$ (3 mg) in 1 mL of $MeCN/H_2O$, 4:1 was freshly prepared. $^{18}F$-Fluoride (3.0-4.0 GBq) was separated from $^{18}O$-enriched-water using a Chromafix PSHCO3 $^{18}F$ separation cartridge (45 mg) and subsequently released with 900 μL (in 6×150 μL portions) of the $K_{222}/K_2CO_3$ solution into a 5 mL V-vial containing a magnetic stir bar in the concentrator. The solution was dried with five cycles of azeotropic drying with MeCN (5×200 μl) under a flow of $N_2$ at 105° C. The dried $[^{18}F]KF/K_{222}$ residue was redissolved in anhydrous MeCN (500-1000 L).

General Procedure for Small Scale Heterocycle Screening Experiments with 4-(4,4,5,5-tetramethyl-1,3,2-dioxaborolan-2-yl)benzonitrile A solution of $[^{18}F]KF/K_{222}$ in MeCN (20-30 MBq, 10-50 μL) was dispensed into a V-vial containing $Cu(OTf)_2(py)_4$ (0.0053 mmol), 4-(4,4,5,5-tetramethyl-1,3,2-dioxaborolan-2-yl)benzonitrile (13.7 mg, 0.06 mmol) and a magnetic stirrer bar. Air (20 mL) was flushed through the reaction vial using a syringe and then a solution containing the heterocycle (0.06 mmol) in DMF (300 μL) was added via syringe. The sealed vial was heated at 110° C. for 20 minutes. The reaction was quenched by addition of water (200 L). An aliquot was removed for analysis by radioTLC and HPLC for radiochemical conversion and product identity. Analysis was performed using a Waters Nova-Pak C18 column (4 m, 3.9×150 mm) at a flow rate 1 mL/min. Radio-TLC was performed on Merck Kiesegel 60 F254 plates, using n-hexane/EtOAc (1:1) as eluent. Analysis was performed using a plastic scintillator/PMT detector.

General Procedure for Small Scale $^{18}F^-$ Labeling of Arenes:

A solution of $[^{18}F]KF/K_{222}$ in MeCN (20-30 MBq, 10-50 μL) was dispensed into a V-vial containing Copper source (0.03 mmol), aryl pinacol boronate (0.02 mmol) and a magnetic stirrer bar. Air (20 mL) was flushed through the reaction vial using a syringe and then solvent (300 μL) was added via syringe. The sealed vial was heated at 110° C. for 20 minutes. The reaction was quenched by addition of water (200 μL). An aliquot was removed for analysis by radioTLC and HPLC for radiochemical conversion and product identity. Analysis was performed using the gradient given below with a Waters Nova-Pak C18 column (4 μm, 3.9×150 mm)

at a flow rate 1 mL/min. Radio-TLC was performed on Merck Kiesegel 60 F254 plates, using as eluent DCM/MeOH (9:1). Analysis was performed using a plastic scintillator/PMT detector.

HPLC Gradient for Small Scale Heterocycle Screening Experiments and Small Scale $^{18}F$-Labeling of Arenes:

Water/MeCN, 1 mL/min, Waters Nova-Pak C18 Column, 4 μm, 3.9×150 mm 0-1 min (5% MeCN) isocratic 1-10 min (5% MeCN to 95% MeCN) linear increase 10-14 min (95% MeCN) isocratic 14-15 min (95% MeCN to 5% MeCN) linear decrease 15-17 min (5% MeCN) isocratic.

Procedure for the Synthesis and Isolation of [$^{18}F$]Olaparib

A reaction scheme showing the synthesis of [$^{18}F$]olaparib in accordance with this Example is shown in FIG. 2. $^{18}F$-Fluoride was separated from $^{18}O$-enriched-water using an anion exchange cartridge (Sep-Pak Accell Plus QMA Carbonate Plus Light Cartridge, 46 mg Sorbent per Cartridge, 40 μm particle size, Waters) and released with 900 μL (in 6×150 μL portions) of a solution of $K_{222}/K_2C_2O_4/K_2CO_3$ (kryptofix 222 (6.3 mg), $K_2C_2O_4$ (1 mg) and $K_2CO_3$ (0.1 mg) in 1 mL of MeCN/$H_2O$, 4:1) into a 5 mL V-vial containing a magnetic stir bar in the concentrator. The solution was dried with five cycles of azeotropic drying with MeCN (5×200 μL) under a flow of $N_2$ at 105° C. The 5 mL vial containing the dried [$^{18}F$]KF/$K_{2.2.2}$ complex was purged with 30 mL of air using a syringe and then a solution of arylboronate precursor (13.4 mg, 0.02 mmol) and Cu(OTf)$_2$(impy)$_4$ (25 mg, 0.03 mmol) in anhydrous 1,3-dimethyl-2-imidazolidinone (DMI) (300 μL) was added. The mixture was heated at 120° C. for 20 min in a sealed vial with stirring. After 20 min, TFA (350 L) was added and stirring was continued at 120° C. for 20 min. The reaction was then cooled to room temperature before quenching with $H_2O$ (6 mL) and eluting over a Oasis HLB Plus cartridge (preconditioned with 2 mL MeOH and 10 mL $H_2O$). The vial was then rinsed with $CH_3CN$:$H_2O$ (1:9, 2.0 mL), and eluting over the Oasis HLB cartridge after which the product was eluted with $CH_3CN$ (2.0 mL) into a 5 mL V-vial. The MeCN was evaporated under a flow of $N_2$ at 100° C. until approximately 50 μL remained. The reaction mixture was then diluted with 28% MeCN/72% 25 mM $NH_4HCO_2$ in $H_2O$ and loaded directly onto a 2 mL HPLC loop and injected on a semi-Prep HPLC column (Synergi 4 μm Hydro-RP 250×10 mm) and eluted into a collection vial with 28% MeCN/72% 25 mM $NH_4HCO_2$ in $H_2O$ monitoring with UV (254 nm) and radioactive traces.

The [i$^{18}F$]Olaparib was collected in 10 mL of $H_2O$ and eluted over a Oasis HLB Plus cartridge (preconditioned with 2 mL MeOH and 10 mL $H_2O$). The cartridge was washed with $H_2O$ (1.0 mL), after which the product was eluted with EtOH (2.0 mL). The ethanol was evaporated under a flow of $N_2$ while heating at 100° C. The dry residue was then re-dissolved in 10% DMSO/PBS (pH=7.4).

Figures 9A, 9B:
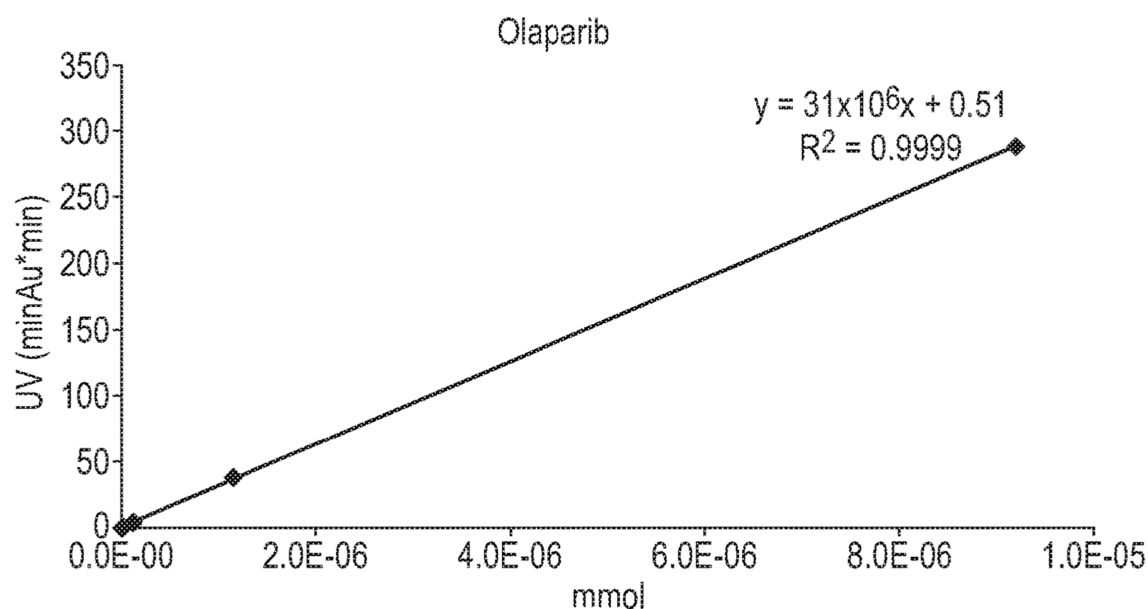
FIG. 9 shows (a) a graph and (b) a table of calculations of the molar activity of [$^{18}$F]olaparib as assessed by radio-HPLC, using an analytical Synergi 4 μm Hydro-RP 80A column, 150×4.6 mm eluted with 25% MeCN/75% $H_2O$ (isocratic 1 mL/min), monitoring with UV (220 nm) and radioactive traces. In the table of FIG. 9(*b*) the calculations are of the molar activity of [$^{18}$F]olaparib $^a$under oxalate drying conditions and $^b$under carbonate drying conditions.

The Molar Activity of [$^{18}F$]Olaparib was assessed by radio-HPLC, using an analytical Synergi 4 μm Hydro-RP 80A column, 150×4.6 mm eluted with 25% MeCN/75% $H_2O$ (isocratic 1 mL/min), monitoring with UV (220 nm) and radioactive traces (FIG. 9).

4. Radiosynthesis Results and Discussion

[$^{8}F$]Olaparib Synthesis Via Copper-Mediated $^{18}F$-Fluorodeboronation of Aryl Pinacol Boronic Esters

[$^{18}F$]Olaparib was prepared via copper-mediated $^{18}F$-fluorodeboronation of a N-[2-(trimethylsilyl)ethoxy]methyl]-protected boronic pinacol ester precursor (FIG. 2) in an activity yield of 18%±3% (non-decay corrected radiochemical yield, n=5) with molar activities up to 25.7 GBq/μmol.

It has previously been demonstrated that copper-mediated $^{18}F$-fluorodeboronation can be used to synthesise $^{18}F$-fluoroarenes (WO 2015/140572; Tredwell, M., et al., Angew Chem Int Ed Engl 53, 7751-7755, 2014; Preshlock, S., et al., Chem Commun (Camb) 52, 8361-8364, 2016; Preshlock, S., Tredwell, M. & Gouverneur, V., Chemical reviews 116, 719-766, 2016; Taylor, N. J., et al., Journal of the American Chemical Society 139, 8267-8276, 2017). In the case of [$^{18}F$]olaparib, however, a heterocycle screening experiment performed by the present inventors using 4-(4,4,5,5-tetramethyl-1,3,2-dioxaborolan-2-yl)benzonitrile as the substrate in the presence of phthalazone as the heterocycle (see Scheme 1 below) revealed that an unprotected boronic ester would be incompatible with such $^{18}F$-fluorodeboronation potentially due to interference of the phthalazone nitrogen with the Cu-complex catalyst. A tert-butyloxycarbonyl (BOC) protecting group was also found not to work. It was therefore necessary to develop a different strategy for an $^{18}F$-fluorodeboronation to produce [$^{18}F$]olaparib.

A number of protecting groups intended for the phthalazone nitrogen were tested in further heterocycle screening experiments, using 4-(4,4,5,5-tetramethyl-1,3,2-dioxaborolan-2-yl)benzonitrile as the substrate in the presence of phthalazone bearing various candidate protecting groups as the heterocycles (see Scheme 1 below). Amongst the protecting groups tested was N-[2-(trimethylsilyl)ethoxy]methyl](SEM), despite the fact that the inventors were not expecting SEM to be compatible with an $^{18}F$-fluorodeboronation reaction due to the known tendancy of silicon to be highly fluorophilic and of trialkylsilyl groups to be susceptible to cleavage upon treatment with fluoride to form the corresponding trialkylsilyl fluoride. The inventors therefore expected that the $^{18}F$-fluoride used in the $^{18}F$-fluorodeboronation would react with the SEM group itself, rather than with the aryl boronic ester group, and that the $^{18}F$-fluorodeboronation reaction would not therefore take place in the presence of SEM.

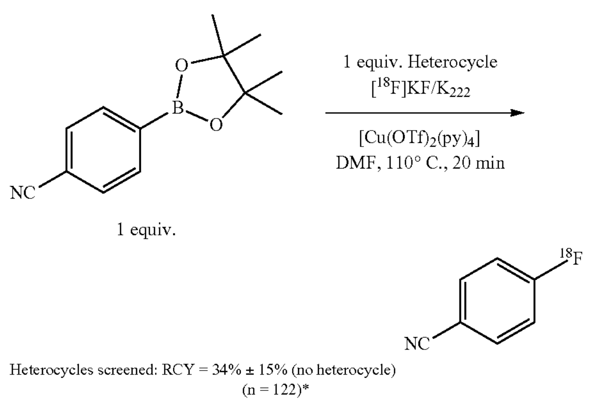

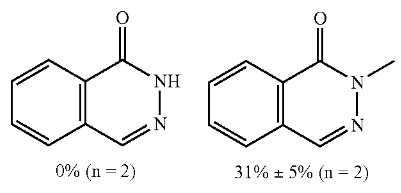

-continued

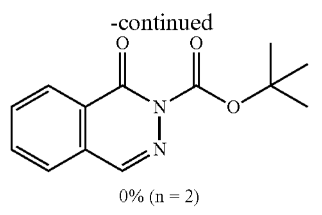

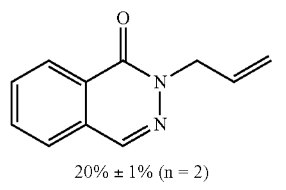

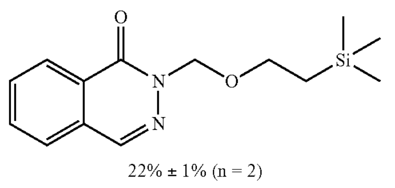

* Taylor, N. J., et al. Derisking the Cu-Mediated $^{18}F^{-}$ Fluorination of Heterocyclic Positron Emission Tomography Radioligands. J Am Chem Soc 139, 8267-8276 (2017).

Scheme 1: Heterocycle Screening Experiments: Screening of Protecting Groups

The heterocycle screening experiments predicted that protected boronic ester substrates bearing N-methyl protection, N-allyl protection, and, surprisingly, N-[2-(trimethylsilyl)ethoxy]methyl](SEM) protection, respectively, would undergo successful $^{18}F^{-}$ fluorodeboronation. In the case of SEM, it was surprisingly found that the $^{18}F^{-}$ did not preferentially react with the SEM group during the screening experiment, but instead reacted with the aryl boronic ester group to perform the $^{18}F$-fluorodeboronation successfully. The radiochemical yield (RCY) in the presence of SEM was similar to that in the absence of heterocycle.

The finding that N-[2-(trimethylsilyl)ethoxy]methyl] (SEM) might be an effective nitrogen protecting group for $^{18}F$-fluorodeboronation was unexpected, given the known tendancy of silicon to be highly fluorophilic, and of trialkylsilyl groups to be susceptible to cleavage upon treatment with fluoride to form the corresponding trialkylsilyl fluoride. Indeed, a SEM group would generally be expected to react with fluoride, to produce trimethylsilyl fluoride plus ethylene and formaldehyde as decomposition products (which is exactly what commonly occurs when tetrabutylammonium fluoride (TBAF) is used to remove a SEM group from a nitrogen atom in a deprotection reaction). For this reason, silicon-containing protecting groups are generally avoided by those skilled in the art of $^{18}F$ radiochemistry when radiolabelling compounds with $^{18}F$-fluoride. The fact that the $^{18}F$ did not preferentially react with the SEM group during the screening experiment, and the $^{18}F$-fluorodeboronation was instead performed successfully, was therefore entirely unexpected.

Furthermore, this led the inventors to select SEM as the candidate protecting group for the phthalazone nitrogen in the organoboron precursor to [$^{18}F$]olaparib, because the SEM protecting group has certain key advantages over N-methyl and N-allyl protecting groups in the context of producing an $^{18}F$-radiolabeled agent for in vivo administration. Unlike SEM, an N-methyl protecting group is very difficult to remove once deprotection is desired to produce the NH group in the final, radiolabelled compound. Also, unlike SEM, removal of an N-allyl protecting group to produce NH generally requires use of a palladium catalyst, and the use of a heavy metal in the final step of the synthesis of a radiopharmaceutical suitable for in vivo administration would be undesirable, owing to the need for subsequent purification to remove the metal. Such difficult, lengthy and/or complicated deprotection and purification steps are desirably avoided after the $^{18}F$ label has been introduced, owing to the need for quick administration of the radiolabelled compound to the patient after radiosynthesis due to the short half-life of $^{18}F$. SEM was therefore an advantageous, albeit counterintuititve, choice of protecting group given its propensity for facile removal under mild conditions.

SEM was therefore chosen by the inventors as the candidate protecting group for the phthalazone nitrogen in the organoboron precursor to [$^{18}F$]olaparib. The protected boronic ester substrate bearing N-[2-(trimethylsilyl)ethoxy]methyl](SEM) protection did indeed undergo successful $^{18}F$-fluorodeboronation as shown in FIG. 2, as predicted by the screening experiments (in Scheme 1 above).

The optimal catalyst for $^{18}F$-fluorodeboronation of this substrate, out of those tested, was shown to be $Cu(OTf)_2(impy)_4$ (impy=imidazo[1,2-b]pyridazine), while the use of 1,3-dimethyl-2-imidazolidinone (DMI) proved to be the solvent that led to the most optimal radiochemical yield (see Scheme 2 and Table 1 below).

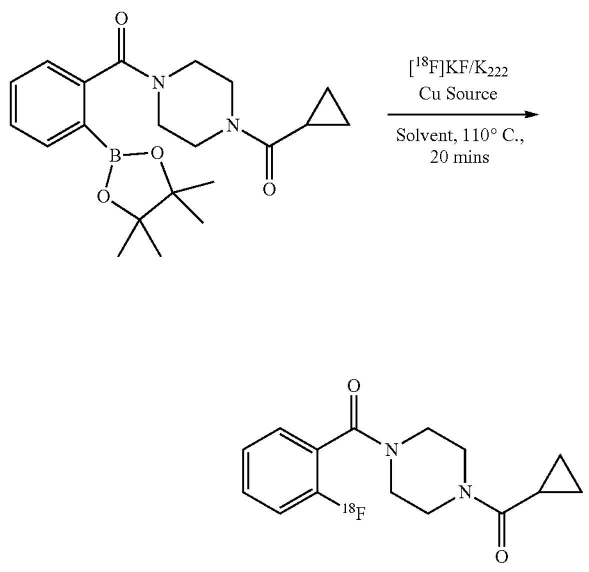

Scheme 2: Screening of Solvents and Cu Sources: Radiochemical Conversion of (4-(Cyclopropanecarbonyl) piperazin-1-yl)(2-(4,4,5,5-tetramethyl-1,3,2-dioxaborolan-2-yl)phenyl)methanone

TABLE 1

Radiochemical conversion of (4-(Cyclopropanecarbonyl)piperazin-1-yl)(2-(4,4,5,5-tetramethyl-1,3,2-dioxaborolan-2-yl)phenyl)methanone

| Cu Source | Solvent (400 μL) | RCC (n = 2) |
|---|---|---|
| $Cu(OTf)_2(py)_4$ | DMA | 17% ± 3% |
| $Cu(OTf)_2(impy)_4$ | DMA | 48% ± 1% |
| $Cu(OTf)_2(impy)_4$ | DMI | 82% ± 1% |

Figure 7:
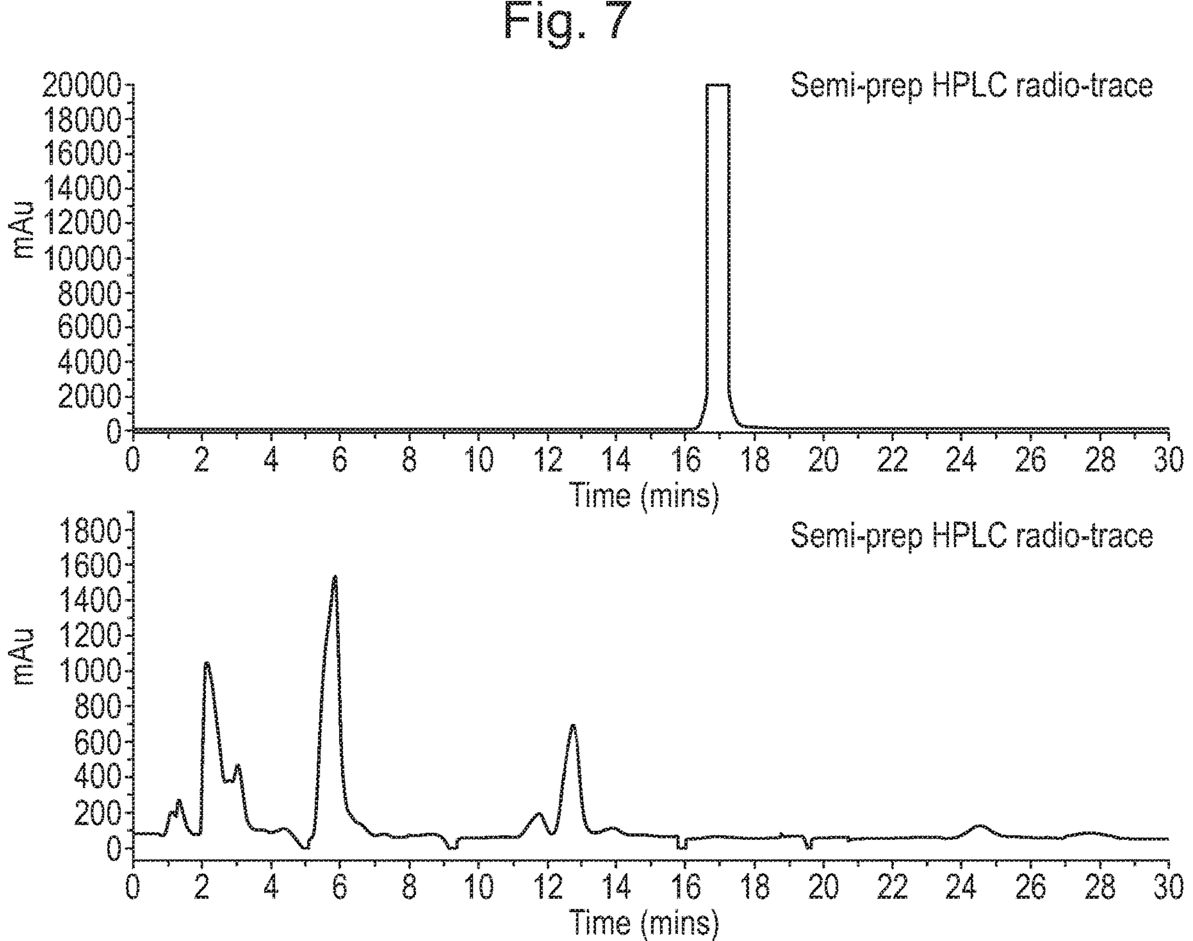
FIG. 7 shows a semi-prep HPLC radio-trace (top) and a semi-prep HPLC UV-trace (bottom) for the semi-prep radioHPLC purification of [$^{18}$F]olaparib.

The unwanted side product, 4-(3-(4-(cyclopropanecabonyl)piperazine-1-carbnonyl)benzyl)phthalazin-1(2H)-one, produced by proto-deboronation of the precursor 4-(3-(4-(cyclopropanecarbonyl)piperazine-1-carbonyl)-4-(4,4,5,5-tetramethyl-1,3,2-dioxaborolan-2-yl)benzyl)-2-((2-trimethlsilyl)ethoxy)methyl)phthalazin-1(2H)-one, could be separated from the desired product, [$^{18}$F]olaparib, HPLC (FIGS. 4, 5, 7 and 8), thus allowing for isolation of a highly pure product by semipreparative HPLC (see FIGS. 7 and 8).

The Molar Activity of [$^{18}$F]Olaparib was assessed by radio-HPLC, using an analytical Synergi 4 μm Hydro-RP 80A column, 150×4.6 mm eluted with 25% MeCN/75% $H_2O$ (isocratic 1 mL/min), monitoring with UV (220 nm) and radioactive traces. FIG. 9 shows (a) a graph and (b) a table of calculations of the molar activity of [$^{18}$F]olaparib as assessed by the radio-HPLC. In the table of FIG. 9(*b*) the calculations are of the molar activity of [$^{18}$F]olaparib [a]under oxalate drying conditions and [b]under carbonate drying conditions.

5. Biology

PARP1 levels in a limited selection of PDAC cell lines were determined using Western blot and confirmed by immunofluorescence microscopy. Uptake of [$^{18}$F]olaparib in cells was determined by exposing aliquots of cells growing in 24-well plates to external beam radiation (0-10 Gy; using a $^{137}$Cs irradiator (1 Gy/min)), after which the cells were incubated with [$^{18}$F]olaparib (50 kBq) for 30 min. Uptake was reported as a percentage of the total amount added, per mg of total protein recovered from the isolated cells, determined by BCA assay. Specificity of uptake was determined by blocking olaparib binding sites using an excess of cold, unlabeled olaparib, or other PARP inhibitors (rucaparib, talazoparib).

Cells

Panc-1, MiaPaCa-2, and Capan-1 human pancreatic duct adenocarcinoma cells were purchased from ATCC. Cells were maintained in Dulbecco's Modified Eagle Medium (DMEM), supplemented with 10% foetal bovine serum (FBS), 2 mM L-glutamine, 100 units/mL penicillin, and 0.1 mg/mL streptomycin. Cells were grown in a 37° C. environment containing 5% $CO_2$ and were harvested and passaged as required using Trypsin-EDTA solution. Cells were authenticated by the provider and the cumulative length of culture was less than 6 months following retrieval from liquid nitrogen storage.

Western Blot

Western blot probing for PARP1 was performed after cells were exposed to external beam radiation (0 or 10 Gy; $^{137}$Cs source, using a using an IBL-637 $^{137}$Cs irradiator, Cisbio International; 1 Gy/min) with 2 or 24 hours recovery.

Total protein preparations were produced at 4° C. on approximately $1\times10^7$ cells using RIPA lysis buffer (50 mM Tris, pH 8, 1% NP40, 0.5% sodium deoxycholate, 0.1% sodium dodecyl sulphate, 150 mM sodium chloride, cOmplete™ protease inhibitor cocktail [Sigma-Aldrich]). The cell lysates were isolated by centrifugation after lysis through a 21 G hypodermic syringe and 30 second sonication. Thirty microgram lysate samples were run on a 4-12% Bis-Tris MES gel (Novex), transferred to a PVDF membrane and exposed to a 1:500 dilution of anti-PARP1 antibody (Proteintech 13371-ap-1), followed by a 1:3000 dilution of the secondary goat anti-rabbit-HRP (Bio-Rad). The membrane was exposed to autoradiography film after development using an ECL western blot substrate solution (Pierce Thermo Scientific 32209). β-actin was used as the loading control.

Immunocytochemistry

Low-passage Capan-1, Panc-1 and U87 cells, obtained from ATCC and screened for *mycoplasma*-free status, were plated onto 8-chamber slides (Falcon CultureSlides) at $7\times10^4$ cells per chamber in 0.75 mL culture media and incubated overnight in a 37° C. $CO_2$ incubator until approximately 80% confluent. The slides were briefly in phosphate-buffered saline (PBS) pH7.4, and the cells fixed in 4% formaldehyde/PBS for 10 minutes. The slides were washed in PBS for 3×5 minutes, and cells permeabilized in 0.5% Triton X100 (Sigma) for 10 minutes. The cells were washed as before and non-specific binding was blocked by incubation of the slides in 2% BSA/PBS for 1 hour. To each appropriate section approximately 100 μl primary antibody diluted 1:100 and 1:250 in 2% BSA/PBS, or just 2% BSA/PBS, was applied, and incubated in a humid chamber for 2 hours. The primary antibodies used were anti-PARP-1 rabbit polyclonal (ProteinTech), or anti-PARP-1 monoclonal (Santa Cruz). The slides were washed in PBS for 3×5 minutes, and the secondary goat-anti-mouse IgG-488 antibody, or goat-anti-rabbit IgG-594 antibody (Life Technologies Alexa Fluor, 1:500 dilution in 2% BSA/PBS), was applied and incubated for 1 hour. The slides were then washed in PBS for 3×5 minutes, excess fluid removed with a tissue, and a drop of Vectashield+DAPI (Vector Laboratories) was applied to each section. Finally a coverslip was gently lowered onto each slide, and Covergrip (Biotium) used to seal the coverslips. Prepared slides were stored at 4° C. in the dark. The slides were analysed using a Leica SP8 confocal fluorescent microscope.

Cell Uptake Experiments

Cell uptake of $^{18}$F-olaparib in Panc-1, MiaPaCa-2 and Capan-1 cells was determined as previously described (Cornelissen, B., Hu, M., McLarty, K., Costantini, D. & Reilly, R. M.

Cellular penetration and nuclear importation properties of 111In-labeled and 123I-labeled HIV-1 tat peptide immunoconjugates in BT-474 human breast cancer cells. Nucl Med Biol 34, 37-46, 2007; Thurber, G. M., Reiner, T., Yang, K. S., Kohler, R. H. & Weissleder, R. Effect of small-molecule modification on single-cell pharmacokinetics of PARP inhibitors. Molecular cancer therapeutics 13, 986-995, 2014; Reiner, T., et al. Imaging therapeutic PARP inhibition in vivo through bioorthogonally developed companion imaging agents. Neoplasia 14, 169-177, 2012). Aliquots of Panc-1, MiaPaca-2, and Capan-1 cells ($1.5\times10^5$ cells/well) were seeded in 24-well plates in warm cell culture medium (500 μL) and the cells were allowed to adhere overnight. Cells were irradiated (10 Gy; dose rate 0.8 Gy/min) or sham-irradiated and then returned to an incubator (37° C., 5% $CO_2$) for 2 h. The cell culture medium was then removed and cells were washed once with fresh cell culture medium (500 μL). In 500 μL of cell culture medium (not supplemented with FBS, L-glutamine, or penicillin/streptomycin), [$^{18}$F]-olaparib (50 kBq) was added to each well and the cells were then incubated at 37° C. In the blocking groups, non-radioactive olaparib, talazoparib, or rucaparib were also added in increasing concentrations (10 pM-10 μM. After 30 or 60 minutes, the cell culture medium was removed and combined with two washes (500 μL) of cell culture medium. The remaining monolayer of cells was then lysed with 0.1 M sodium hydroxide for 20 minutes at room temperature. The amount of radioactivity contained within the cell culture medium and the cell lysate fractions was measured using a gamma counter. Protein levels from parallel plates were quantified using a Pierce BCA protein assay kit (Thermo Scientific) according to the manufacturer's recommendations and bovine serum albumin was used as the protein standard. Cell uptake levels of [$^{18}$F]-olaparib were normalised to percent of the total added radioactivity per milligram protein. These experiments were performed in triplicate on at least three separate occasions. IC50 values were calculated using GraphPad Prism software (GraphPad Software, San Diego, CA, USA). Data are presented as mean±SEM.

Radiation Dose Dependency

Aliquots of Panc-1, MiaPaca-2, and Capan-1 cells (7.5×$10^4$ cells/well) were seeded in 24-well plates in warm cell culture medium (500 μL). After 4 h, cells were irradiated (0, 2, 4, 6, 8, or 10 Gy; dose rate 0.8 Gy/min) and then returned to an incubator (37° C., 5% $CO_2$). After 24 or 48 h, the cell culture medium was then removed and cells were washed once with fresh cell culture medium (500 μL). In 500 μL of cell culture medium (not supplemented with FBS, L-glutamine, or penicillin/streptomycin), [$^{18}$F]-olaparib (50 kBq) was added to each well and the cells were then incubated at 37° C. In the blocking groups, non-radioactive olaparib was also added to each well to achieve a concentration of 10 μM. After 30 minutes, the cell culture medium was removed and combined with two washes (500 μL) of cell culture medium. The remaining monolayer of cells was then lysed with 0.1 M sodium hydroxide for 20 minutes at room temperature. The amount of radioactivity contained within the cell culture medium and the cell lysate fractions was measured using a gamma counter. Protein levels from parallel plates were quantified using a Pierce BCA protein assay kit (Thermo Scientific) according to the manufacturer's recommendations and bovine serum albumin was used as the protein standard. Radiotracer cell uptake levels were normalised to percent of the total added radioactivity per milligram protein.

In Vivo Tumour Models

All animal procedures were performed in accordance with the UK Animals (Scientific Procedures) Act 1986 and with local ethical committee approval. Animals were housed in IVC cages in sex-matched groups up to 5 per cage, in an artificial day-night cycle facility, with ad libitum access to food and water. Tumour xenografts or allografts were generated by subcutaneous injection of PANC-1 or Capan-1 cell suspensions in the hind flank of balb/c nu/nu animals. CaNT xenografts were generated by harvesting CaNT tumours from donor animals, and injecting a tumour homogenate subcutaneously in the flank of wild type CBA/Carl mice. Tumours were irradiated (10 Gy, 2 Gy/min) using a 300 kV X-ray device.

Dynamic PET/CT images were acquired following an intravenous bolus administration of [$^{18}$F]-olaparib. Biodistribution studies, where selected tissues were harvested, were performed 1 h post injection. Some animals were also administered an excess of cold, unlabelled olaparib for evaluating the specificity of tumour uptake. EF5, a hypoxia-selective marker, was injected 2 h before culling of the animal. Digital autoradiography was performed on tumour sections. Image analysis was performed using PMOD.

All statistical analyses were performed using GraphPad Prism.

Panc-1 and Capan-1

Cells were harvested using trypsin, washed twice using PBS, and reconstituted in DMEM. Panc-1 or Capan-1 xenograft tumours were established in the right hind flank of female NOD/SCID mice (Charles River, UK) by subcutaneous injection of 1×$10^6$ cells in PBS:matrigel (150 μL). Tumour volumes (V) were calculated after calliper measurement using the following equation: $V=(a^2 \times b)/2$, where a is the width of the tumour and b the length (small and large diameters, respectively). The individual relative tumour volume (RTV) was defined as $Vt/V_0$, where Vt is the volume at a given time and $V_0$ at the start of treatment. Animals were entered in in vivo studies when their tumour was at least 200 $mm^3$.

CaNT

The murine adenocarcinoma NT (CaNT) was implanted subcutaneously onto the right thigh of 6-7 week-old female CBA/Carl mice. Fifty μL of a crude cell suspension, prepared by mechanical dissociation of an excised tumor from a donor animal, was injected. Tumors were selected for imaging when the geometric mean diameter reached 6-8 mm (volumes calculated as above), approximately 3 weeks after implantation (Kersemans, V., et al. Hypoxia imaging using PET and SPECT: the effects of anesthetic and carrier gas on [Cu]-ATSM, [Tc]-HL91 and [F]-FMISO tumor hypoxia accumulation. PloS one 6, e25911, 2011).

6. PET/CT Imaging $^{18}$F-Olaparib PET Imaging

Figure 13:
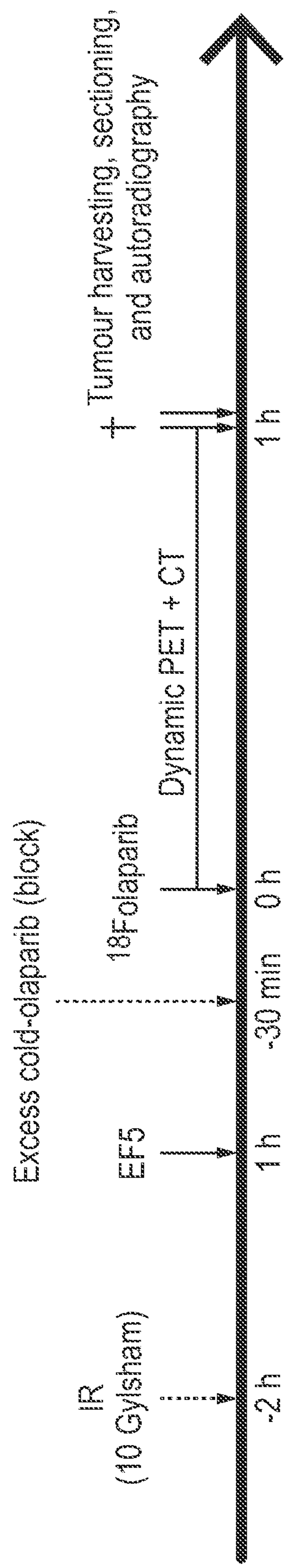
FIG. 13 is a schematic representation of the irradiation and PET/CT imaging schedule in xenograft-bearing animals.
Figure 14:
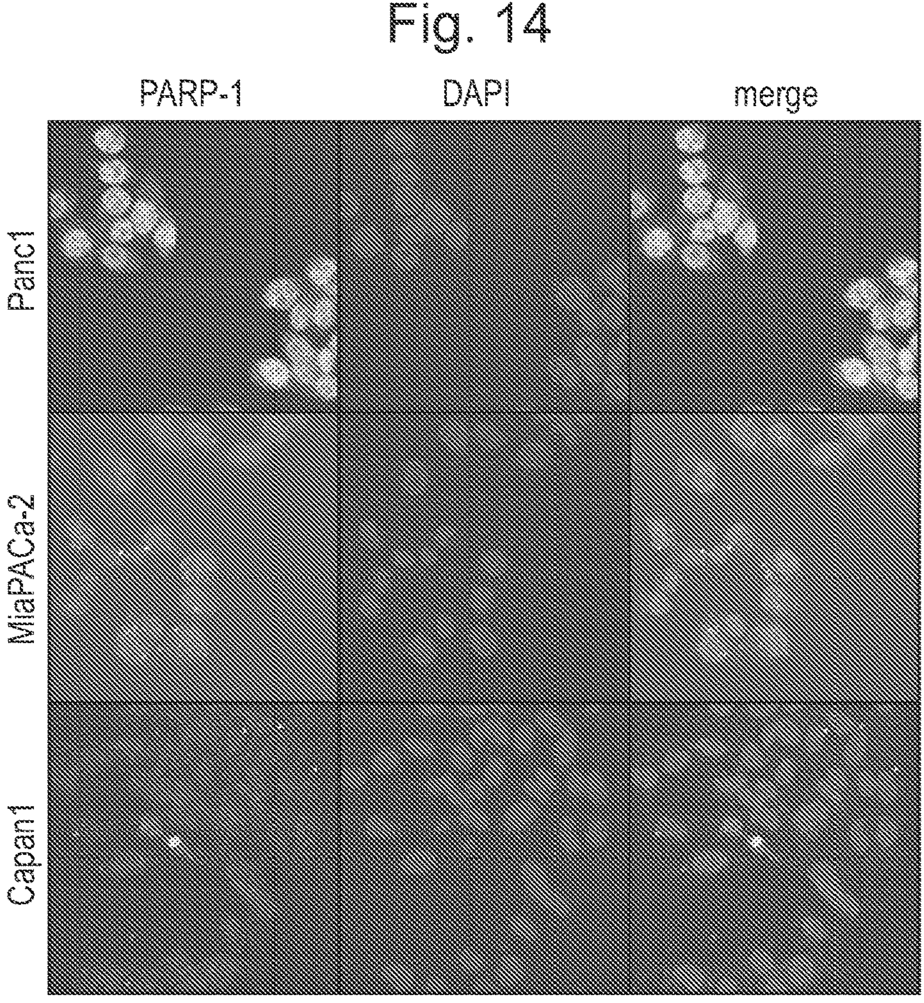
FIG. 14 are micrographs showing immunocytochemistry of PARP1 in a selection of PDAC cell lines.
Figure 15:
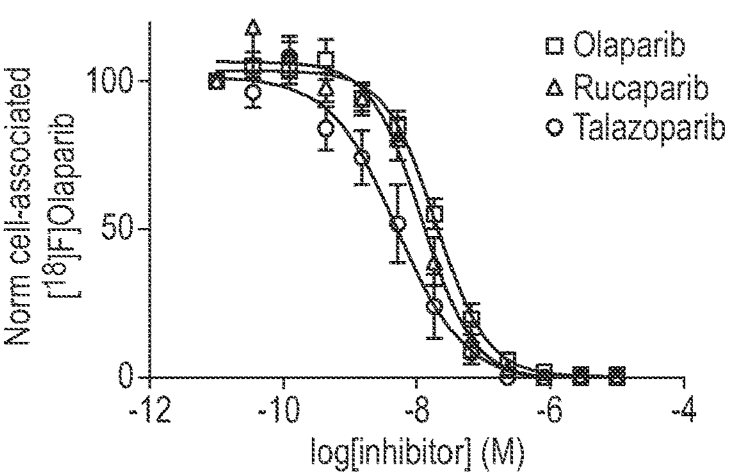
FIG. 15 is a graph showing the displacement of $^{18}$F-olaparib uptake in PANC-1 cells by a selection of several PARP inhibitors.

Two hours prior to PET/CT imaging, animals were exposed to X-irradiation of the tumour (10 Gy or sham) (see schedule in FIG. 13). Radiation was delivered using a Gulmay 320 kV X-irradiator; 2.0 Gy/min. Anaesthesia was maintained at 2.5% isoflurane throughout the duration of the irradiation, and animals were allowed to recover. To study the relationship of PARP1 expression, $^{18}$F-olaparib uptake and hypoxia, animals were administered 0.6 μg in 200 μL (0.9% saline) intraperitoneally, one hour prior to PET/CT imaging. Naïve CBA/Carl mice, not bearing tumours, were not irradiated, nor was EF5 administered.

Dynamic PET/CT images were acquired using a VECTor$^4$CT integrated PET/CT system. Mice were anaesthetised by 4% isoflurane gas (0.5 L/min $O_2$) and placed on a custom-built imaging cradle in a prone position. Animals mice were intravenously injected with [$^{18}$F]-olaparib or (3-5 MBq, 8-11 GBq/μmol, through a tail vein catheter, and dynamic imaging was performed over 45-60 min after radiolabelled compound administration. PET acquisition (150 s per frame, using list mode acquisition) using an ultra-high resolution rat/mouse 1.8 mm collimator, followed by a cone-beam CT scan (55 kV, 0.19 mA) for anatomical reference and attenuation correction. Anaesthesia was maintained at 2.5% isoflurane throughout the duration of the image acquisition. PET images were reconstructed using U-SPECT-Rec3.22 software (MILabs, Utrecht, The Netherlands), applying a pixel-based algorithm with 8 subsets, 6 iterations and 0.8 mm voxel size for $^{18}$F (energy window settings 477.9-584.1 keV).

Image Analysis

Reconstructed images were viewed and analysed using PMOD v.3.37 (PMOD Technologies, Zurich, Switzerland). The radioactivity in each volume of interest was calculated as % Injected dose per cubic cm (% ID/mL).

7. Ex Vivo Biodistribution

After PET/CT image acquisition, animals were euthanized by cervical dislocation and selected organs, tissues and blood were removed. The amount of radioactivity in each organ was measured using a 2480 WIZARD$^2$ gamma counter (PerkinElmer). Counts per minute were converted into MBq using a calibration curve generated from known standards. Values were decay-corrected to the time of injection, and the percentage of the injected dose per gram (% ID/g) of each tissue was calculated.

8. Ex Vivo Analysis

Autoradiography

After imaging and automated gammacounting, selected tissues from mice were flash-frozen with dry ice. If required, samples were stored at −80° C. overnight. Frozen tissue was sectioned (8 μm) using an OTF5000 cryotome (Bright Instruments Ltd). Tissue sections were thaw-mounted onto Superfrost PLUS glass microscope slides (Menzel-Glaser, Thermo Scientific) and allowed to dry at room temperature. The slides were then exposed to a storage phosphor screen (PerkinElmer, Super Resolution, 12.5×25.2 cm) in a standard X-ray cassette for 15 h at 4° C. or −20° C. The phosphor screen was then imaged using a Cyclone® Plus Storage Phosphor System (PerkinElmer) and images were analysed with OptiQuant 5.0 (PerkinElmer) and ImageJ (NIH).

Immunohistochemistry

PARP1 Staining

Panc-1 xenografts harvested from mice were flash frozen and 8 μm sections were prepared using a cryostat. Sections were stored at −80° C. until use. Slides were allowed to reach room temperature (10 minutes), then washed briefly in phosphate-buffered saline (PBS) pH7.4. The slides were fixed in 4% formaldehyde/PBS for 10 min, then washed three times in PBS for 5 min. Sections were permeabilized in 0.5% Triton X100 (Sigma) for 10 min, washed, and non-specific binding was blocked by incubation of the slides in 2% BSA/PBS for 1 h. Slides were briefly allowed to dry and each section was isolated using a PAP pen (Sigma). To each appropriate section approximately 100 μl primary anti-PARP1 polyclonal antibody (ProteinTech) diluted 1:100 and 1:250 in 2% BSA/PBS, or just 2% BSA/PBS, was applied, and incubated in a humid chamber overnight at 4° C. The slides were washed three times in PBS for 5 min, and the secondary goat-anti-rabbit IgG-488 antibody (Life Technologies Alexa Fluor, 1:500 dilution in 2% BSA/PBS), was applied and incubated for 1 h. The slides were then washed in PBS, excess fluid removed, mounted using Vectashield containing DAPI (Vector Laboratories). Slides were stored at 4° C. in the dark. Images were acquired using a Leica SP8 confocal fluorescent microscope.

EF5 Staining

Tumor hypoxia was confirmed by immunohistological staining for EF5 (2-(2-nitro-1H-imidazol-1-yl)-N-(2,2,3,3,3-pentafluoropropyl)-acetamide). For EF5 studies, mice were administered with 10 mM EF5 in 0.9% saline i.v. 2 h prior to tumor excision (EF5 was obtained from Dr. Cameron Koch, University of Pennsylvania; Koch, C. J. http://www.hypoxia-imaging.org/v2/methods/ef5manual.htm. Vol. 2011). To determine the correlation between $^{18}$F-olaparib uptake and hypoxia, tumor slices were analysed by both autoradiography and EF5 IHC (Lee, J., Siemann, D. W., Koch, C. J. & Lord, E. M. Direct relationship between radiobiological hypoxia in tumors and monoclonal antibody detection of EF5 cellular adducts. Int J Cancer 67, 372-378 (1996); Kersemans, V., et al. Hypoxia imaging using PET and SPECT: the effects of anesthetic and carrier gas on [Cu]-ATSM, [Tc]-HL91 and [F]-FMISO tumor hypoxia accumulation. PloS one 6, e25911 (2011); Hueting, R., et al. A comparison of the behavior of (64)Cu-acetate and (64)Cu-ATSM in vitro and in vivo. J Nucl Med 55, 128-134, 2014). Object-based overlap between both modalities was determined by first co-registering autoradiography and fluorescence microscopy images using a rigid transformation. Then, Manders' overlap coefficients (M1) were calculated using the JACoP plug-in for Image J (methods of Manders for spatial intensity correlation analysis with Costes method for automatic thresholding).

8. Statistical Methods

All statistical analyses and nonlinear regression were performed using GraphPad Prism (GraphPad Software, San Diego, CA, USA). Data were tested for normality and analysed either by the unpaired, two-tailed Student's t-test where appropriate, or 1-way analysis of variance (ANOVA) for multiple comparisons, with Dunnet's post-tests to calculate significance of differences between groups. All data were obtained at least in triplicate and results reported as mean±standard deviation, unless stated otherwise.

9. Supplementary Tables

TABLE 2

Ex vivo biodistribution $^{18}$F-olaparib in naïve CBA/Carl mice.

| | % ID/g | | |
|---|---|---|---|
| Blood | 0.11 | 0.11 | 0.14 |
| Heart | 0.19 | 0.17 | 0.34 |
| Lung | 0.29 | 0.19 | 0.34 |
| Liver | 2.55 | 4.02 | 5.27 |
| Spleen | 2.09 | 1.91 | 3.68 |
| Stomach | 0.46 | 0.26 | 0.58 |
| Large intestine | 0.92 | 1.64 | 2.99 |
| Small intestine | 7.75 | 10.33 | 17.40 |
| Pancreas | 0.91 | 0.70 | 1.30 |
| Kidney | 0.59 | 0.60 | 1.01 |
| Muscle | 0.20 | 0.14 | 0.34 |
| Skin | 0.16 | 0.10 | 0.27 |
| Fat | 0.05 | 0.03 | 0.26 |

TABLE 3

Ex vivo biodistribution $^{18}$F-olaparib in Panc-1 xenograft bearing mice.

| | $^{18}$F-Olaparib | | | | | | $^{18}$F-Olaparib + IR (10 Gy) | | | $^{18}$F-Olaparib + block | | | |
|---|---|---|---|---|---|---|---|---|---|---|---|---|---|
| Blood | 0.41 | 0.73 | 0.57 | 0.24 | 0.21 | 0.19 | 0.63 | 0.83 | 1.17 | 2.12 | 2.29 | 2.51 | 1.06 |
| Tumour | 1.94 | 4.07 | 4.20 | 3.27 | 2.43 | 3.07 | 6.43 | 3.03 | 6.59 | 1.68 | 0.92 | 1.09 | 1.09 |
| Heart | 3.18 | 2.05 | 1.74 | 1.58 | 0.85 | 1.07 | 3.14 | 2.49 | 2.88 | 1.98 | 1.59 | 1.51 | 0.78 |

TABLE 3-continued

Ex vivo biodistribution $^{18}F$-olaparib in Panc-1 xenograft bearing mice.

| | $^{18}F$-Olaparib | | | | | | $^{18}F$-Olaparib + IR (10 Gy) | | | $^{18}F$-Olaparib + block | | | |
|---|---|---|---|---|---|---|---|---|---|---|---|---|---|
| Lung | 4.68 | 3.51 | 3.18 | 2.15 | 1.45 | 1.69 | 3.94 | 4.47 | 4.47 | 1.61 | 1.40 | 1.32 | 0.74 |
| Liver | 26.2 | 34.6 | 27.0 | 21.0 | 13.5 | 18.0 | 25.1 | 33.8 | 45.7 | 29.1 | 32.9 | 22.4 | 23.1 |
| Spleen | 17.5 | 13.7 | 11.3 | 14.0 | 7.36 | 8.01 | 45.0 | 20.5 | 14.3 | 1.62 | 1.46 | 1.24 | 0.69 |
| Stomach | 2.59 | 3.53 | 1.81 | 1.80 | 0.55 | 0.60 | 4.15 | 0.92 | 0.87 | 1.44 | 0.79 | 0.46 | 0.21 |
| Large intestine | 12.6 | 30.5 | 80.8 | 27.0 | 28.9 | 6.61 | 27.5 | 28.9 | 16.2 | 20.1 | 13.3 | 61.4 | 12.7 |
| Small intestine | 54.5 | 58.1 | 30.6 | 31.9 | 18.6 | 26.6 | 65.1 | 113 | 95.2 | 89.9 | 77.2 | 96.4 | 132 |
| Pancreas | 8.49 | 9.38 | 7.25 | 5.52 | 2.78 | 4.24 | 13.6 | 10.3 | 11.4 | 1.92 | 2.29 | 1.91 | 1.79 |
| Kidney | 10.5 | 7.95 | 6.02 | 7.04 | 3.41 | 3.66 | 10.0 | 9.25 | 10.6 | 13.1 | 5.09 | 3.98 | 2.44 |
| Muscle | 1.60 | 1.40 | 1.45 | 1.12 | 0.70 | 0.73 | 3.71 | 2.01 | 1.76 | 1.58 | 1.08 | 1.18 | 0.65 |
| Bone | 3.38 | 4.54 | 2.71 | 1.88 | 1.26 | 1.50 | 9.12 | 4.13 | 3.81 | 1.06 | 0.78 | 0.80 | 0.46 |
| Skin | 1.50 | 1.75 | 2.06 | 1.25 | 0.87 | 1.14 | 2.10 | 2.38 | 2.66 | 1.65 | 1.09 | 1.10 | 0.66 |
| Fat | 0.97 | 0.82 | 0.68 | 0.45 | 0.44 | 0.37 | 0.66 | 1.41 | 0.82 | 0.53 | 0.62 | 0.35 | 0.19 |

TABLE 4

Ex vivo biodistribution $^{18}F$-olaparib in Capan-1 xenograft bearing mice.

| | $^{18}F$-Olaparib | | | | $^{18}F$-Olaparib + IR (10 Gy) | | | $^{18}F$-Olaparib + block | | |
|---|---|---|---|---|---|---|---|---|---|---|
| Blood | 0.30 | 0.23 | 0.31 | 0.72 | 0.86 | 0.43 | 1.16 | 0.25 | 0.27 | 0.56 |
| Tumour | 2.48 | 3.21 | 2.94 | 1.73 | 1.85 | 1.70 | 2.48 | 1.27 | 1.04 | 0.69 |
| Heart | 1.75 | 0.87 | 1.81 | 2.24 | 0.92 | 0.48 | 0.80 | 0.53 | 1.62 | 1.83 |
| Lung | 2.60 | 1.49 | 2.66 | 3.97 | 0.83 | 0.60 | 0.85 | 0.90 | 2.04 | 1.86 |
| Liver | 11.78 | 5.79 | 10.32 | 22.63 | 9.16 | 5.93 | 6.67 | 3.62 | 6.88 | 9.79 |
| Spleen | 9.84 | 6.13 | 8.40 | 15.10 | 0.77 | 0.73 | 0.82 | 2.80 | 7.93 | 6.43 |
| Stomach | 1.55 | 0.63 | 1.14 | 3.42 | 0.38 | 0.36 | 0.64 | 0.30 | 0.49 | 0.94 |
| Large intestine | 4.99 | 4.50 | 4.14 | 8.14 | 5.21 | 3.30 | 5.86 | 2.91 | 4.06 | 5.00 |
| Small Intestine | 12.27 | 17.29 | 11.58 | 13.70 | 15.58 | 9.80 | 19.97 | 0.45 | 11.70 | 46.04 |
| Pancreas | 9.32 | 8.12 | 7.87 | 13.16 | 1.89 | 1.59 | 1.84 | 4.56 | 10.82 | 10.22 |
| Kidney | 4.32 | 2.05 | 4.91 | 5.22 | 4.66 | 1.03 | 3.67 | 1.26 | 3.32 | 4.16 |
| Muscle | 0.65 | 0.45 | 0.63 | 1.44 | 0.63 | 0.29 | 0.48 | 0.28 | 0.65 | 0.88 |
| Bone | 1.46 | 0.98 | 1.26 | 3.08 | 0.31 | 0.16 | 0.19 | 0.47 | 1.27 | 2.17 |
| Skin | 0.02 | 0.55 | 0.77 | 1.54 | 0.67 | 0.23 | 0.33 | 0.14 | 0.46 | 1.16 |
| Fat | 0.46 | 0.19 | 0.27 | 0.69 | 0.24 | 0.13 | 0.19 | 0.22 | 0.77 | 0.36 |
| Brain | 0.82 | 0.03 | 0.03 | 0.10 | 0.06 | 0.03 | 0.03 | 0.03 | 0.03 | 0.04 |
| Caecum | 5.11 | 4.35 | 3.31 | 24.11 | 7.58 | 4.46 | 5.92 | 9.13 | 4.00 | 5.07 |
| Gallbladder | 81.02 | 24.53 | 34.02 | 446.94 | 68.68 | 31.81 | 36.90 | 105.86 | 35.11 | 88.82 |

TABLE 5

Ex vivo biodistribution $^{18}F$-olaparib in CaNT allograft bearing CBA/Carl mice.

| | $^{18}F$-Olaparib | | $^{18}F$-Olaparib + IR (10 Gy) | | $^{18}F$-Olaparib + block |
|---|---|---|---|---|---|
| Blood | 1.78 | 8.00 | 9.79 | 3.12 | 4.00 |
| Tumour | 1.48 | 2.83 | 1.43 | 1.92 | 0.98 |
| Heart | 7.34 | 0.00 | 8.74 | 7.03 | 2.51 |
| Lung | 12.5 | 9.73 | 10.9 | 9.61 | 2.29 |
| Liver | 84.6 | 110 | 93.2 | 100 | 74.3 |
| Spleen | 43.3 | 47.0 | 69.0 | 58.3 | 2.41 |
| Stomach | 6.17 | 12.8 | 9.40 | 4.20 | 4.09 |
| Large intestine | 24.0 | 47.8 | 60.1 | 47.0 | 61.2 |
| Small intestine | 200 | 279 | 455 | 190 | 603 |
| Pancreas | 15.1 | 20.8 | 29.5 | 23.6 | 3.41 |
| Kidney | 23.9 | 21.0 | 24.5 | 19.0 | 8.45 |
| Muscle | 5.84 | 4.63 | 5.45 | 5.31 | 2.65 |
| Bone | 11.7 | 10.2 | 15.7 | 11.5 | 5.18 |
| Skin | 3.82 | 4.65 | 5.02 | 5.12 | 1.16 |
| Fat | 7.19 | 1.12 | 2.52 | 2.34 | 1.57 |
| Brain | 0.29 | 0.23 | 0.20 | 0.25 | 0.22 |

TABLE 5-continued

Ex vivo biodistribution $^{18}F$-olaparib in CaNT allograft bearing CBA/Carl mice.

| | $^{18}F$-Olaparib | | $^{18}F$-Olaparib + IR (10 Gy) | | $^{18}F$-Olaparib + block |
|---|---|---|---|---|---|
| Caecum | 32.5 | 56.2 | 42.9 | 44.6 | 101 |
| Gallbladder | 953 | 126 | 155 | 57.3 | 194 |

10. Biology Results and Discussion

[$^{18}$F]Olaparib Shows Hepatobilliary Clearance in Naïve Mice

Figure 11A:
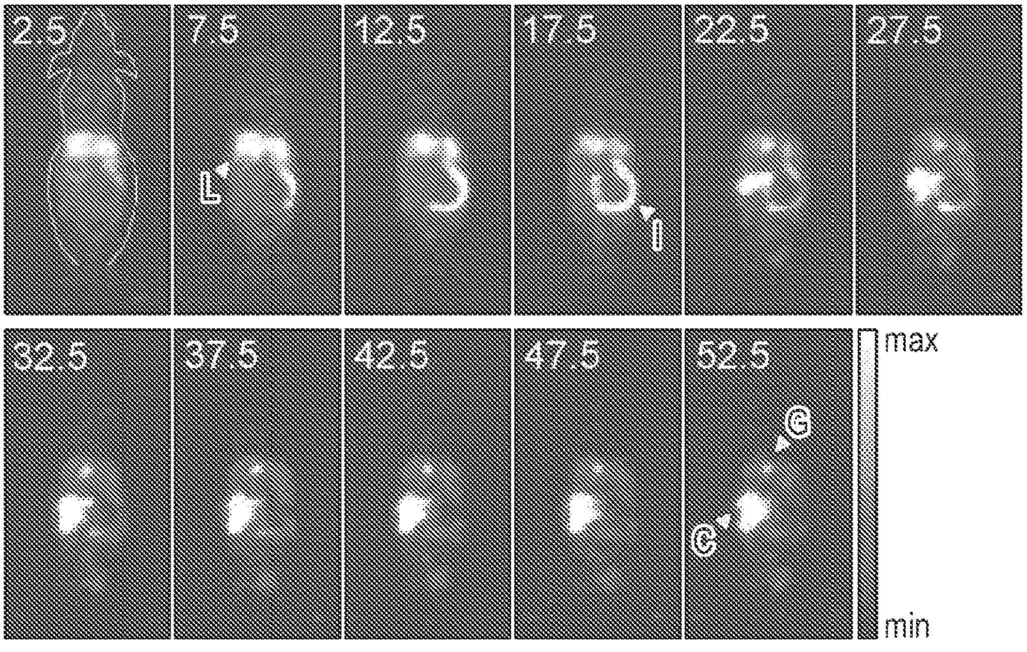
FIG. 11 shows: (A) Representative dynamic PET images after an intravenous bolus injection of [$^{18}$F]olaparib (3 MBq). The middle of the timeframes are indicated in min. Images are presented as MIPs (B) Biodistribution in wild type CBA mice, at 1 h post injection of [$^{18}$F]olaparib. L: liver, G: gall bladder, I: small intestine, C: caecum.
Figure 11B:
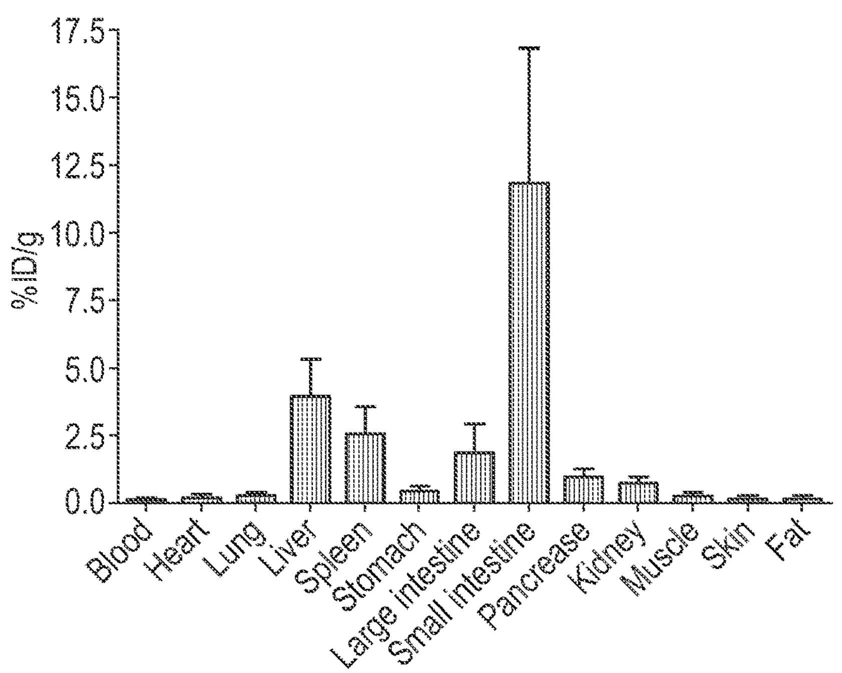
Figure 19:
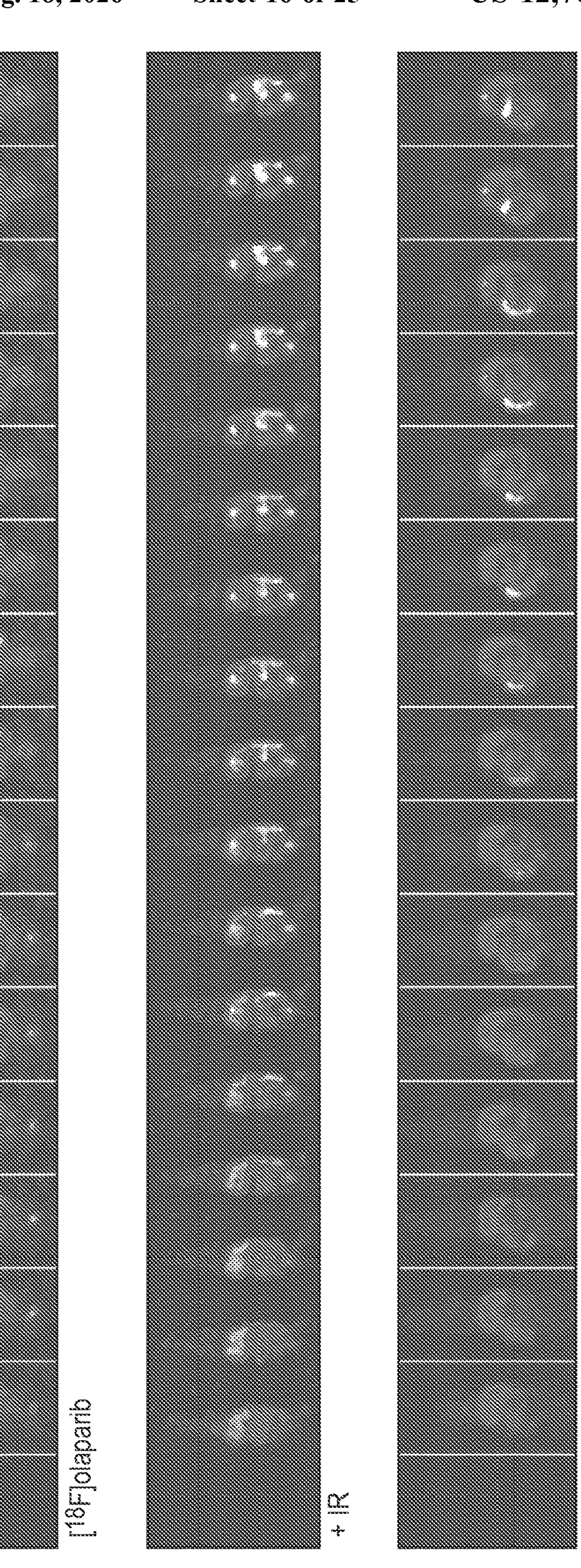
FIG. 19 shows (A) representative dynamic PET images after intravenous bolus injection of [$^{18}$F]-olaparib in Panc-1 tumour-bearing mice. Images are presented as coronal Maximum Intensity Projections, using the same colour scale as in FIG. 3.
Figure 20:
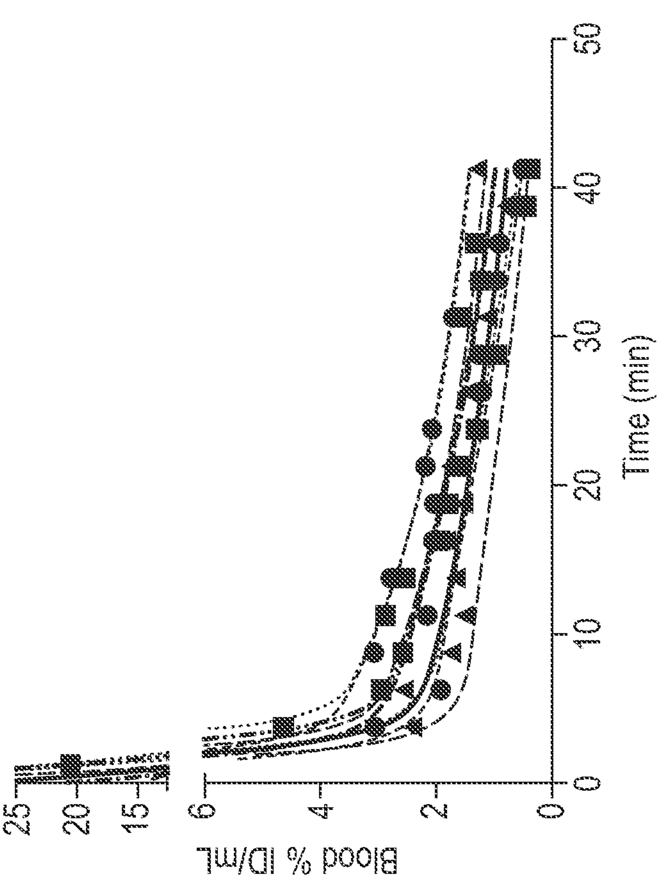
FIG. 20 shows an image quantification of FIG. 19.
Figure 22:
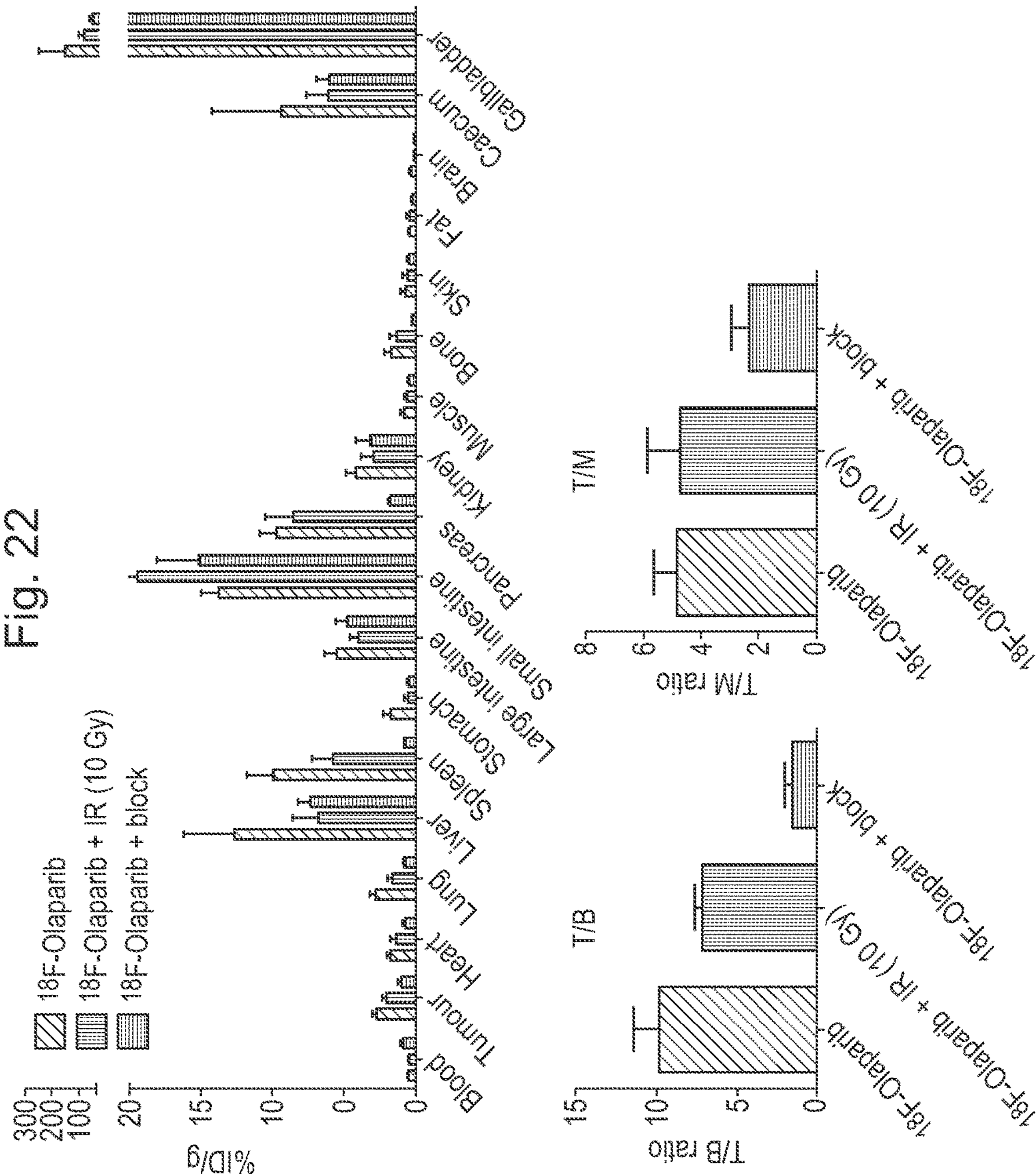
FIG. 22 presents graphs showing the ex vivo biodistribution of $^{18}$F-olaparib in Capan-1 tumour-bearing mice, 1 h after intravenous injection.

In vivo dynamic PET imaging of wild type naïve CBA/Carl mice revealed fast pharmacokinetics and a hepatobiliary clearance pattern, following intravenous administration of 3 MBq [$^{18}$F]olaparib (FIG. 11A). Based on volume-of interest analysis of $^{18}$F signal originating from a region drawn around the heart, the blood clearance of [$^{18}$F]olaparib followed a biphasic pattern (FIG. 16), with fast and slow half-lives of 2.8 min (44%; 95% CI: 2.1-4.0 min) and 32.3 min (56%; 95% CI 27.6-39.1 min), respectively, resulting in a weighted half-life of 19.3 min. Given the very small injected dose of compound (0.0065 mg/kg), the blood half-life of [$^{18}$F]olaparib was markedly shorter than the previously reported half-life of 58 min (in female mice) after intravenous administration of a bolus of 20 mg/kg of olaparib, but slower than the 5.5 min for an $^{18}$F-labelled olaparib-based PARP inhibitor reported by Carney et al. (Carney, B., et al. Non-invasive PET Imaging of PARP1 Expression in Glioblastoma Models. Molecular imaging and biology: MIB: the official publication of the Academy of Molecular Imaging 18, 386-392, 2016). Removal of selected tissues after imaging and measurement of their $^{18}$F content confirmed the results obtained though image-based quantification (FIGS. 11B, 19 and 20), showing low blood retention and high intestinal uptake of [$^{18}$F]olaparib at 1 h post injection.

[$^{18}$F]Olaparib is Taken Up in PARP1-Expressing PDAC Xenografts In Vivo

The biodistribution and clearance pattern in xenograft-bearing animals was similar to that in naïve wild type mice (FIG. 12). Uptake in tissues expressing PARP1, 2, and 3 such as the spleen, bone, and the pancreas was observed, and this uptake could be blocked by co-injection of an excess of cold, unlabelled olaparib, demonstrating the specificity of PARP-targeting. Uptake of [$^{18}$F]olaparib in PARP-1 expressing PANC-1 xenografts amounted to 3.16±0.36% ID/g, measured by biodistribution experiments at 1 h after intravenous bolus injection. The specificity of this uptake was demonstrated by a significant decrease in tumour uptake following co-injection of an excess of cold, unlabelled olaparib, where uptake dropped to 1.20±0.17% ID/g (P=0.0016).

Figures 16, 17:
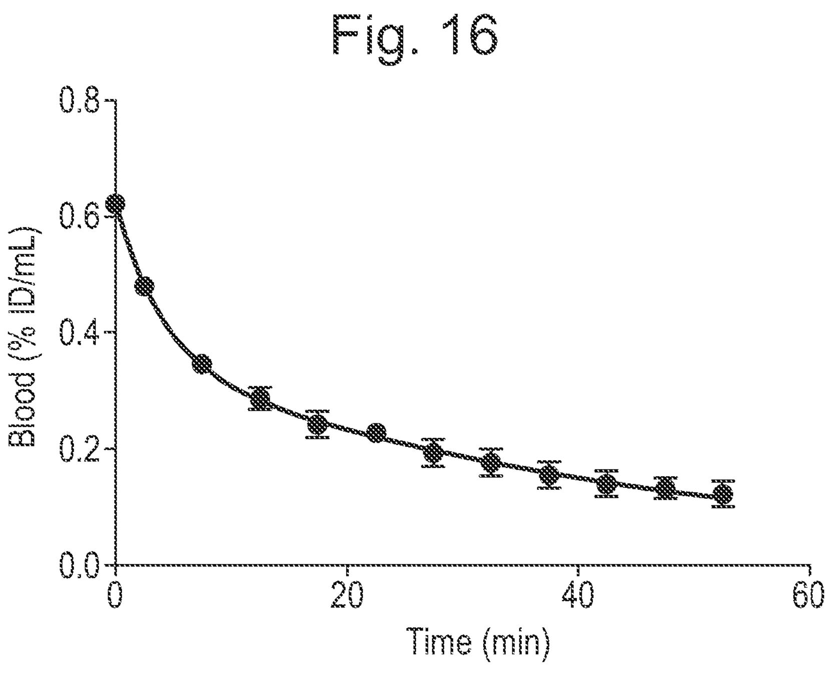
FIG. 16 is a graph of the concentration of $^{18}$F-olaparib in blood of naïve CBA/Carl mice over time following intravenous administration.
FIG. 17 shows a western blot on xenograft tumour tissue from Panc-1 tumours, after irradiation (10 Gy) or sham-irradiation (0 Gy). Xenografts from randomly selected animals were analysed.
Figure 18A:
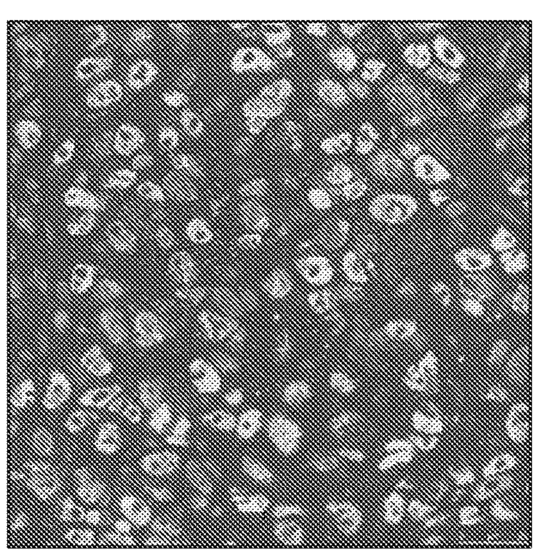
FIG. 18 presents micrographs showing immunohistochemistry staining for PARP-1 on xenograft tumour tissue from Panc-1 (A), CaNT tumours (C). Controls using only secondary antibody showed minimal non-specific staining (B, D).
Figure 18B:
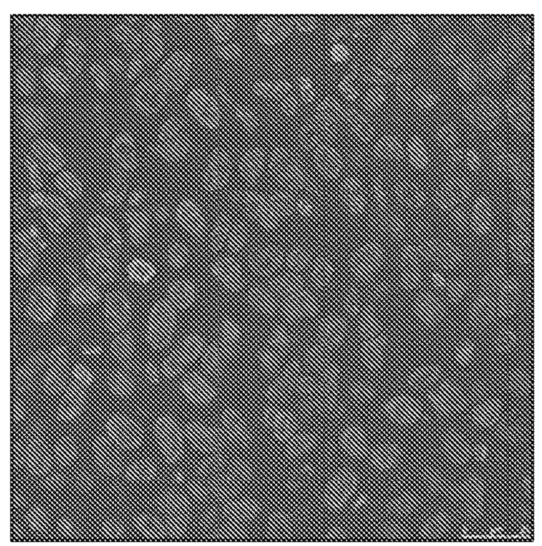
Figure 18C:
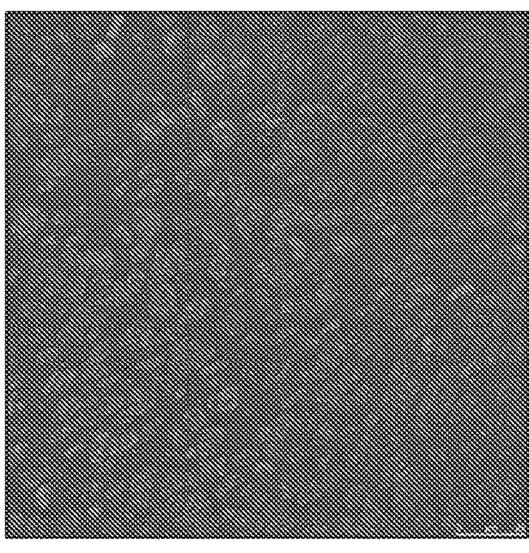
Figure 18D:
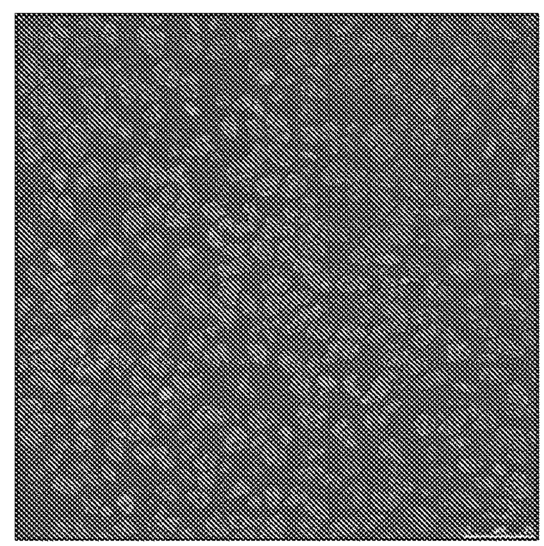
Figure 23:
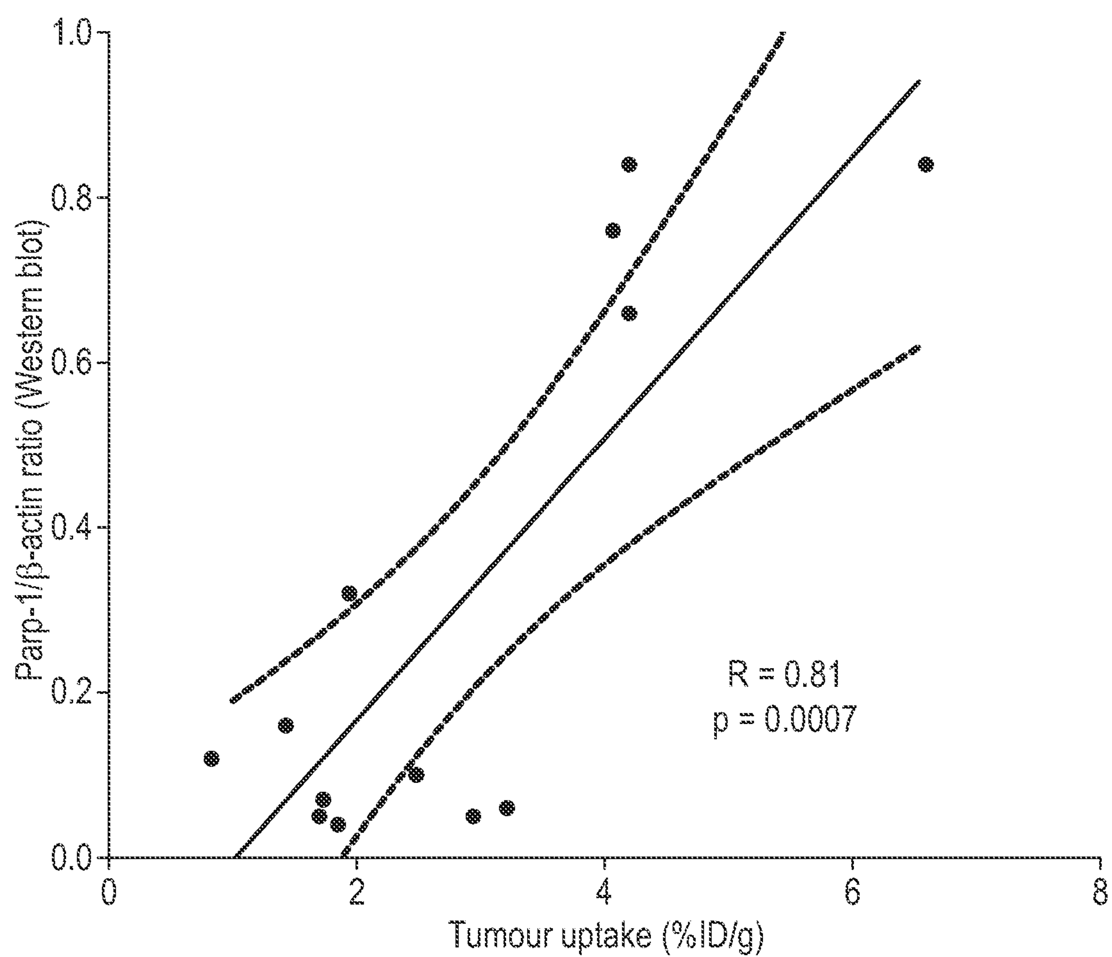
FIG. 23 is a graph showing correlation of tumour uptake determined by ex vivo biodistribution and PARP1 expression measured via Western Blot.

In contrast to PANC-1 tumours, Capan-1 xenografts expressed lower levels of PARP-1, as determined by Western blot and immunohistochemistry (FIGS. 17 and 18). Consistent with lower tumour PARP-1 levels, and consistent with lower in vitro uptake of [$^{18}$F]olaparib, intravenous administration resulted in lower average uptake of [$^{18}$F]olaparib in these tumours (2.59±0.32% ID/g), although this was not statistically significant. Uptake in Capan-1 xenografts could still be blocked by an excess of cold, unlabelled olaparib (to 1.00±0.17; P=0.015), indicating specific uptake of the tracer. CaNT tumours, also expressing low amounts of murine PARP-1 (FIG. 17), presented significantly lower uptake of [$^{18}$F]olaparib compared to PANC-1 xenografts (1.71±0.59% ID/g; P=0.03), and again this uptake could also be blocked by an excess of cold, unlabelled olaparib (to 0.80±0.19% ID/g). Overall, correlation between PARP-1 expression, as measured by Western Blot, correlated well with the uptake of [$^{18}$F]olaparib in xenograft tissues (R=0.81, P=0.0007, FIG. 23).

Figures 10A, 10B, 10C, 10D, 10E:
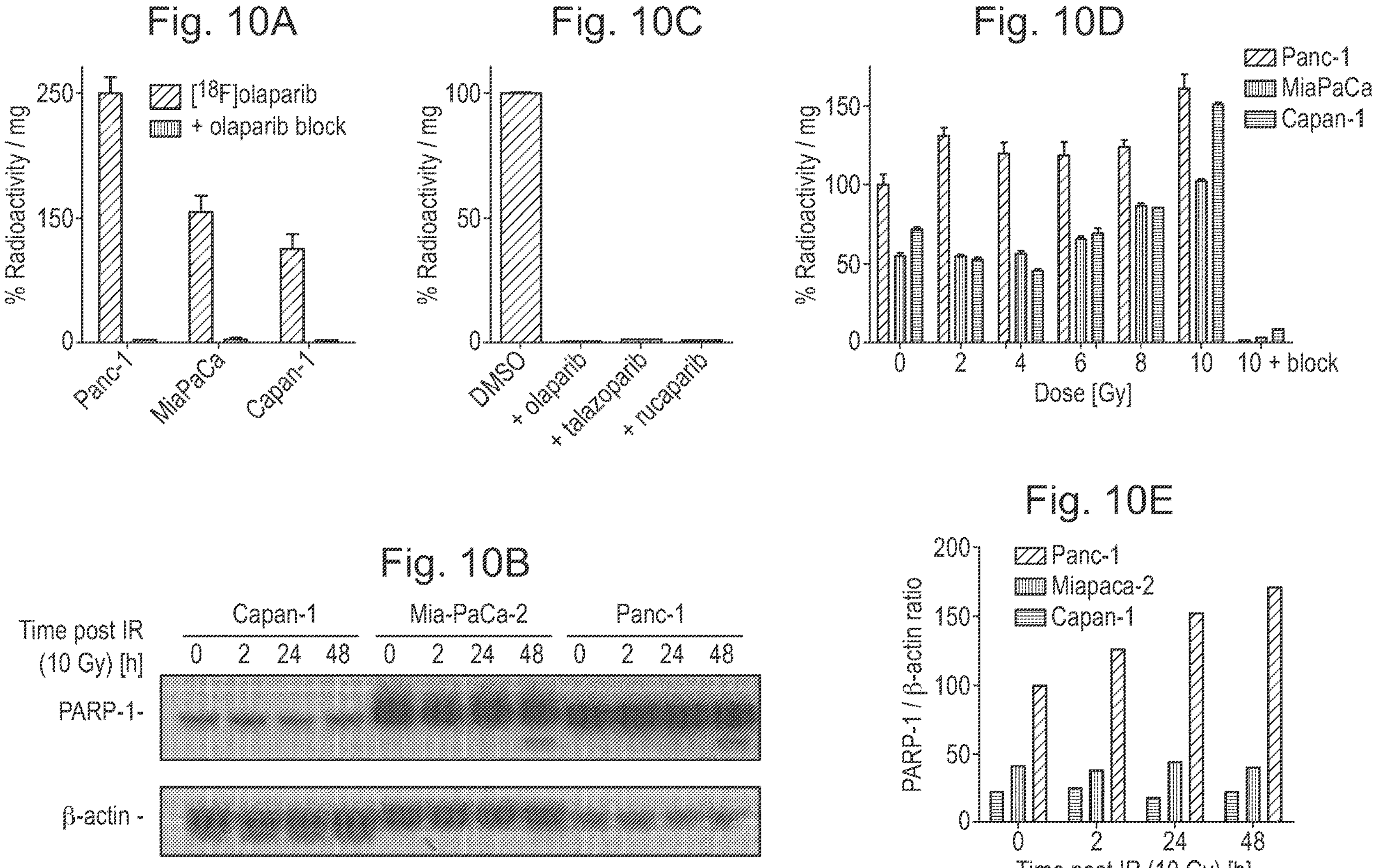
FIG. 10 shows: (A) uptake of $^{18}$F in PANC-1, MiaPaCa-2 and Capan-1 cells, 30 min after addition of [$^{18}$F]olaparib—uptake can be blocked using an excess of cold, unlabelled olaparib; (B) western blot probing for PARP-1 in a panel of PDAC cell lines, before, and after 2, 24, or 48 h of external beam irradiation (10 Gy); (C) that uptake of [$^{18}$F]olaparib in PANC-1 could be blocked by an excess of olaparib, talazoparib, or rucaparib; and (D) uptake of [$^{18}$F]-olaparib in a panel of cell lines, 48 h after external beam irradiation with increasing doses—as a control, uptake of [$^{18}$F]olaparib irradiated at 10 Gy could additionally be blocked by an excess of cold, unlabelled olaparib; and (E) quantification of B.

[$^{18}$F]Olaparib Uptake in PANC-1 Cells and Xenografts is Increased after External Beam Irradiation PARP-1 and 2 are essential for proficient base excision repair. In an effort to explore whether [$^{18}$F]olaparib, which targets PARP, could be used to measure the effects of DNA damaging therapies such as external beam radiotherapy, a panel of cell lines was irradiated, and PARP-1 expression as well as uptake of [$^{18}$F]olaparib was evaluated at several time intervals later. In vitro, 2 h after gamma-irradiation (10 Gy) of cells, Western blot analysis revealed mild increase in PARP-1 expression in PANC-1 cells (FIG. 10B, quantified in FIG. 10E). PARP-2 expression was unaffected (results not shown). In line with these results, [$^{18}$F]olaparib uptake was increased in PANC-1 cells after gamma-irradiation, in a radiation dose-dependent manner, which was more pronounced at later times after irradiation (FIG. 10D). Some degradation of PARP-1 could be observed at later time points, because of caspase-mediated cleavage of PARP-1, attributable to an apoptosis response. Although Mia-PaCa-2 cells showed a small but significant increase in cellular uptake of [$^{18}$F]olaparib (FIG. 10D), no increase in PARP-1 or -2 was observed (FIG. 10E). The small increase in uptake at later time points may therefore be attributable to other factors.

In vivo, 2 h after irradiation of PANC-1 xenografts (10 Gy), uptake of [$^{18}$F]olaparib in the tumour tissue was increased by 70%, from 3.16±0.36 to 5.35±1.16% ID/g (P=0.025) (FIG. 12). This result was consistent with earlier data reported by Kossatz et al. (Kossatz, S., Weber, W. A. & Reiner, T. Optical Imaging of PARP1 in Response to Radiation in Oral Squamous Cell Carcinoma. PloS one 11, e0147752, 2016) who used a fluorescently labelled version of olaparib, visualised using in vivo optical fluorescence imaging, or ex vivo confocal microscopy. The increased expression of PARP-1 in PANC-1 xenografts was confirmed ex vivo using Western blot (FIGS. 12D and 17).

Relationship Between Hypoxia and PARP-1 Expression

Figure 24:
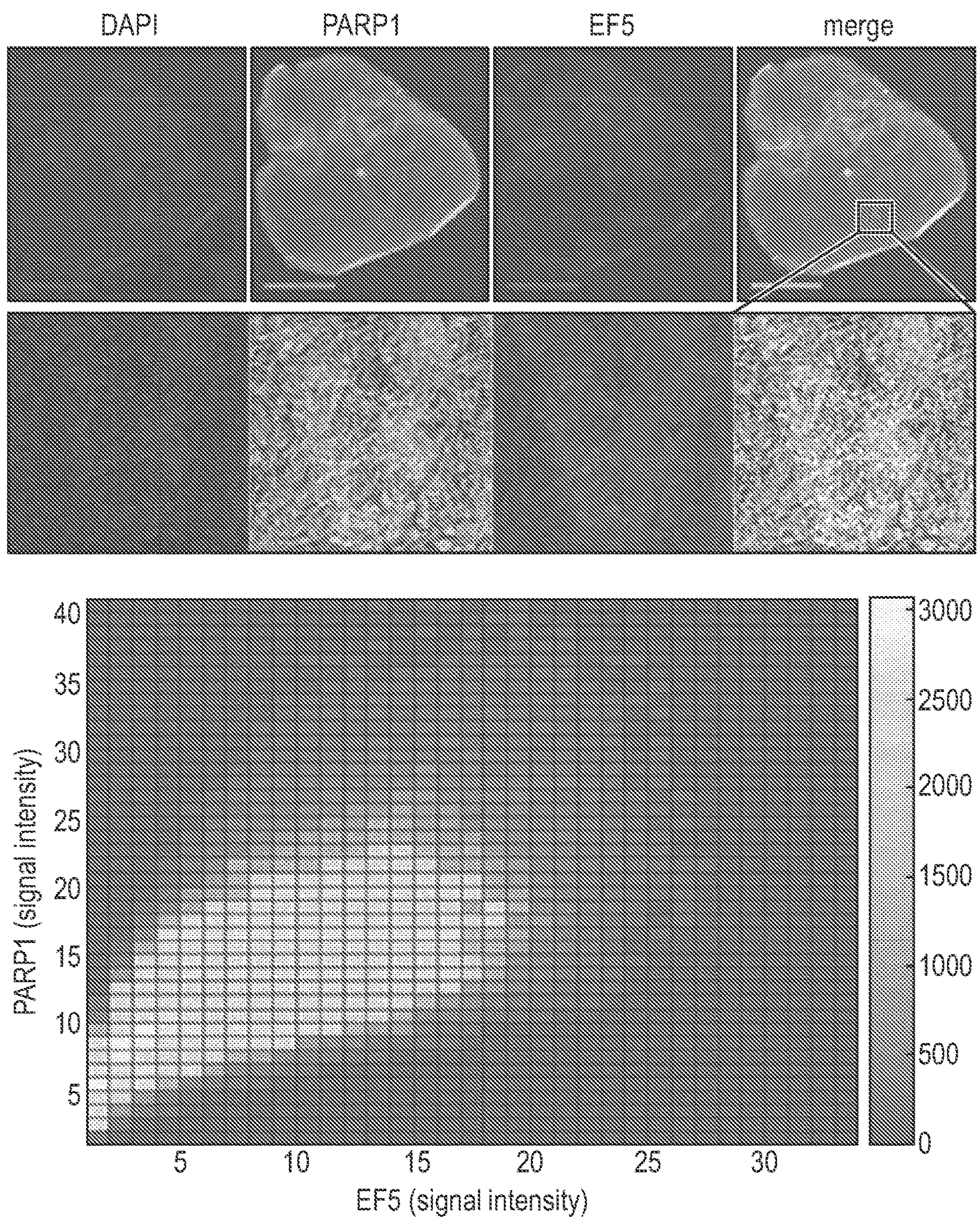
FIG. 24 shows a representative section from a naive PANC-1 xenograft tumour, stained for PARP1 and EF5, including representative high-resolution detail (left); and a cytofluorogram comparing PARP1 versus EF5 signal intensity in the high-resolution image (right).

It is well known that genomic stability in tumour tissue is greatly increased in hypoxic regions (Bristow, R. G. & Hill, R. P. Hypoxia and metabolism. Hypoxia, DNA repair and genetic instability; Nature reviews; Cancer 8, 180-192, 2008). In an effort to investigate the relationship between hypoxia and PARP-1 expression in vivo in tumour xenografts we compared PARP1 signal intensity with EF5 staining, which is known to accumulate in regions of clinically relevant hypoxia. A clear correlation between PARP1 staining and EF5 uptake could be observed in all of the samples (a representative example is shown in FIG. 24), both irradiated and non-irradiated. This observation, in combination with the increased delivery of [$^{18}$F]olaparib to tumours with increased PARP-1 content suggests that olaparib and other PARP inhibitors will be more effective in hypoxic tumour tissue. This prediction is consistent with previous observations by Jiang et al. who demonstrated contextual synthetic lethality for hypoxia and PARP inhibition, where hypoxic cells and tumours are up to a third more sensitive to PARP inhibition compared to fully oxygenated controls (Jiang, Y., et al. Hypoxia Potentiates the Radiation-Sensitizing Effect of Olaparib in Human Non-Small Cell Lung Cancer Xenografts by Contextual Synthetic Lethality. International journal of radiation oncology, biology, physics 95, 772-781, 2016).

DISCUSSION

PARP inhibitors are being intensively studied following the elucidation of the role of PARylation enzymes in DNA damage repair, and the identification of the PARP enzyme, now known as PARP-1, (one of 17 in the PARP enzyme superfamily). Clinical trials were set up to study the effects of a wide variety of compounds, including olaparib (AZD2281, KU0059436), rucaparib (AG-014699, PF-01367338), veliparib (ABT-888), niraparib (MK-4827), talazoparib (BMN-673), or CEP-9722, all of which have been designed to compete for binding to the NAD+ binding pocket of the PARP enzymes. Most of these inhibitors are selective for PARP-1 and -2, with PARP-3 also being inhibited by some, although to a lesser degree. PARP inhibition is largely successful, especially when used in synthetic lethal combination settings, such as in pre-selected tumours with BRCA-ness signatures (Helleday, T., Petermann, E., Lundin, C., Hodgson, B. & Sharma, R. A. DNA repair pathways as targets for cancer therapy. Nat Rev Cancer 8, 193-204, 2008). Nonetheless, resistance to PARP inhibitor treatment is common. Aside from some genetic mechanisms, the failure to deliver sufficient amounts of drug to the tumour tissue has been suggested as the most likely cause. It has been argued that this may occur due to: low systemic doses (for example, as a result of poor oral availability); Rapid clearance or metabolism; Non-specific sequestration by non-target organs rapid export by drug transporter—olaparib is known substrate for such as p-glycoprotein expression; Lack of the target enzyme, or mutations in the binding pocket reducing drug affinity (Thurber, G. M., et al. Single-cell and subcellular pharmacokinetic imaging allows insight into drug action in vivo. Nature communications 4, 1504, 2013). For all of these reasons, using a radiolabelled form of the drug will reveal if drug accumulation in the tumour is sufficient.

Although PARP-1 is by far the most abundant of the DDR-relevant isoforms of PARP, and a PARP-1-selective imaging agent may predict the outcome of PARP inhibition therapy better (Makvandi, M., et al. A Radiotracer Strategy to Quantify PARP-1 Expression In Vivo Provides a Biomarker That Can Enable Patient Selection for PARP Inhibitor Therapy. Cancer research 76, 4516-4524, 2016), [$^{18}$F] olaparib is not selective for one specific isoform. It has previously been well recognised that olaparib affects PARP1, PARP-2 and PARP-3 alike, albeit with varying efficacy (IC50 of olaparib for PARP-1 and PARP-2 is 5, and 1 nM, respectively). It is also known that replacement of the cyclopropanyl side chain in olaparib with a methoxy-moiety (AZ-2461) significantly reduces its affinity towards PARP-3, and consequently reduces PARP-3 mediated bone marrow toxicity in a murine model (Oplustil O'Connor, L., et al. The PARP Inhibitor AZD2461 Provides Insights into the Role of PARP3 Inhibition for Both Synthetic Lethality and Tolerability with Chemotherapy in Preclinical Models. Cancer Res 76, 6084-6094, 2016). Different versions of radiolabelled PARP inhibitors may therefore provide subtly different readouts, and care should be taken in comparing directly. None of small molecule inhibitors of PARP described so far uniquely bind to PARP-1 alone. The only imaging agent with this ability is a PARP-1-selective nanobody-RFP fusion protein (Buchfellner, A., et al. A New Nanobody-Based Biosensor to Study Endogenous PARP1 In Vitro and in Live Human Cells. PloS one 11, e0151041, 2016). Although its use is limited to transfected cells in vitro, as it cannot cross the cell membrane.

When translated to the clinic, PET imaging with [$^{18}$F] olaparib will allow: (a) better patient selection, by determining tumour drug uptake; (b) measurement of the biological effects of genotoxic cancer treatment, such as chemo- and radiotherapy; and (c) allow better patient stratification, making the use of PARP inhibitors even more effective, albeit in a more stringently selected patient population. Several other radiolabelled PARP inhibitors have been reported in the past (Carney, B., Kossatz, S. & Reiner, T. Molecular Imaging of PARP. Journal of nuclear medicine: official publication, Society of Nuclear Medicine 58, 1025-1030, 2017), and some are being translated to the clinic. One early phase 1 clinical trial using a PARP inhibitor-based imaging agent is already underway (using $^{18}F^{-}$ FluorThanatrace, www.clinicaltrials.gov), the results of which will undeniably inform the field of future directions.

It has been shown here that [$^{18}$F]olaparib can be used for quantifying olaparib tumour accumulation, in vitro and in vivo. This study serves as an expansion of the evidence base for the use of PARP imaging agents for clinical PET. The translation of this diagnostic strategy to the clinic will improve significantly patient stratification as well as therapy response monitoring.

Example 2

1. PARP1, PARP2, and PARP3 $IC_{50}$ Determination in Cell-Free Environment

In Table 6, we show the compound concentration at which 50% of PARP1, PARP2 or PARP3 were inhibited ($IC_{50}$) for the cold olaparib (1) and the protodeboronated compound (2). As previously reported, olaparib (1) is selective for PARP2, followed by PARP1, and PARP3. On the other hand, the protodeboronated compound (2) shows significantly different selectivity (PARP3>PARP2>>PARP1).

TABLE 6

$IC_{50}$ values for cold olaparib (1) and the protodeboronated compound (2).

| | Parp-1 $IC_{50}$ [nM] | | Parp-2 $IC_{50}$ [nM] | | Parp-3 $IC_{50}$ [nM] | |
|---|---|---|---|---|---|---|
| Compound | Published[a] | In house[b] | Published[a] | In house[b] | Published[a] | In house[b] |
| 1 | 5 | 2.04 | 1 | 0.46 | 4 | 5.99 |
| 2 | | 7.85 | | 1.08 | | 0.66 |

[a]Isolated recombinant enzyme in vitro assay with $^{3}H\text{-}NAD^{+}$ and DNA resulting in ribosylation and liquid scintillation counting.
[b]PARP-mediated polyADP-ribosylation of histone and chemiluminescence readout, BPS Bioscience.

liquid scintillation counting. [b] PARP-mediated polyADP-ribosylation of histone and chemiluminescence readout, BPS Bioscience.

The chemical structure of cold olaparib (1) is shown in FIG. 1A(a) herein. The protodeboronated compound (2) has the same chemical structure as olaparib (1) except that the F atom in olaparib (1) is replaced with an H atom in (2).

2. PARP1, PARP2, and PARP3 Protein Expression in U87MG and U251MG Cell Lysates

Figure 25:
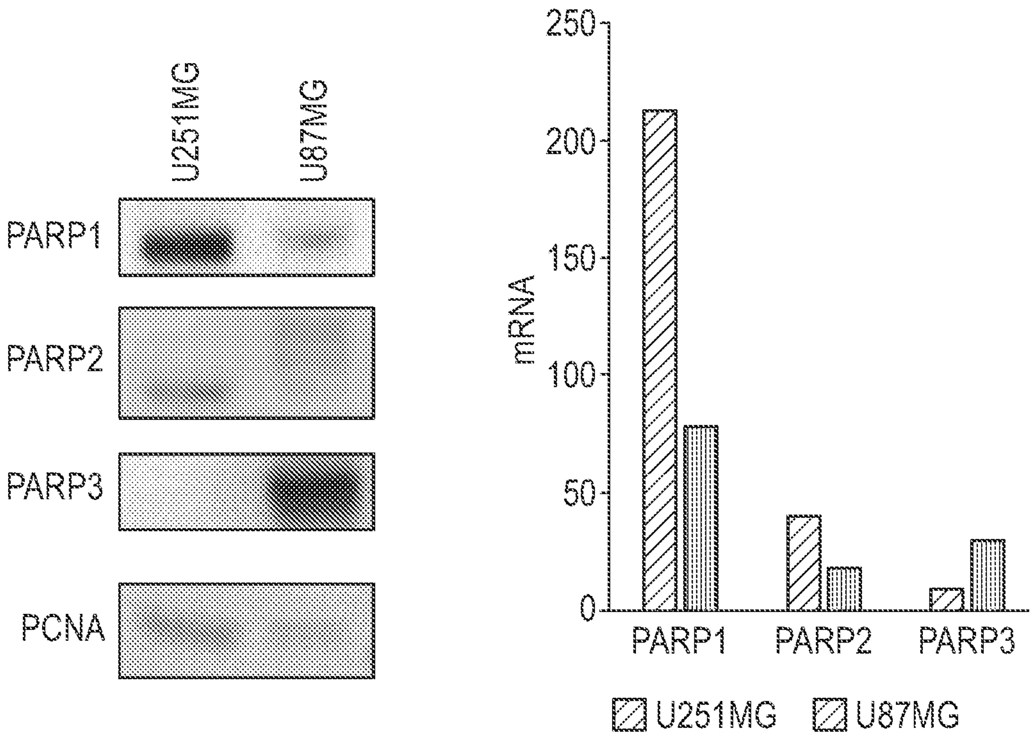
FIG. 25 shows Western Blot characterisation of PARP1, PARP2 and PARP3 protein expression in U87MG and U251MG cell lysates (left hand figure) and corresponding mRNA expression (right hand graph).

Western blot was used to characterise the expression of PARP1, PARP2, and PARP3 in U87MG and U251MG cell lysates and was then compared to mRNA expression (Human Protein Atlas); see FIG. 25. U251MG and U87MG display similar expression levels of PARP2. However, for PARP1 U251MG displays a markedly higher expression while for PARP3 U251MG is negligible compared to the U87MG cell lysates. It is expected that the U251MG cells would display an increased uptake in comparison to U87MG cells as PARP1 and PARP2 are suggested as the main target.

3. Blocking of $^{18}$F-Olaparib Isotopologue in U87MG and U251MG Cells

Olaparib (1) was used used at various concentrations to block 1 μM of the radiolabelled isotopologue, $^{18}$F-olparib (compound 3); see FIG. 26. Here we show that at 100 times the concentration, we are able to block ~70% of the uptake of the $^{18}$F-olaparib in vitro, with a P<0.001.

Figures 27A, 27B:
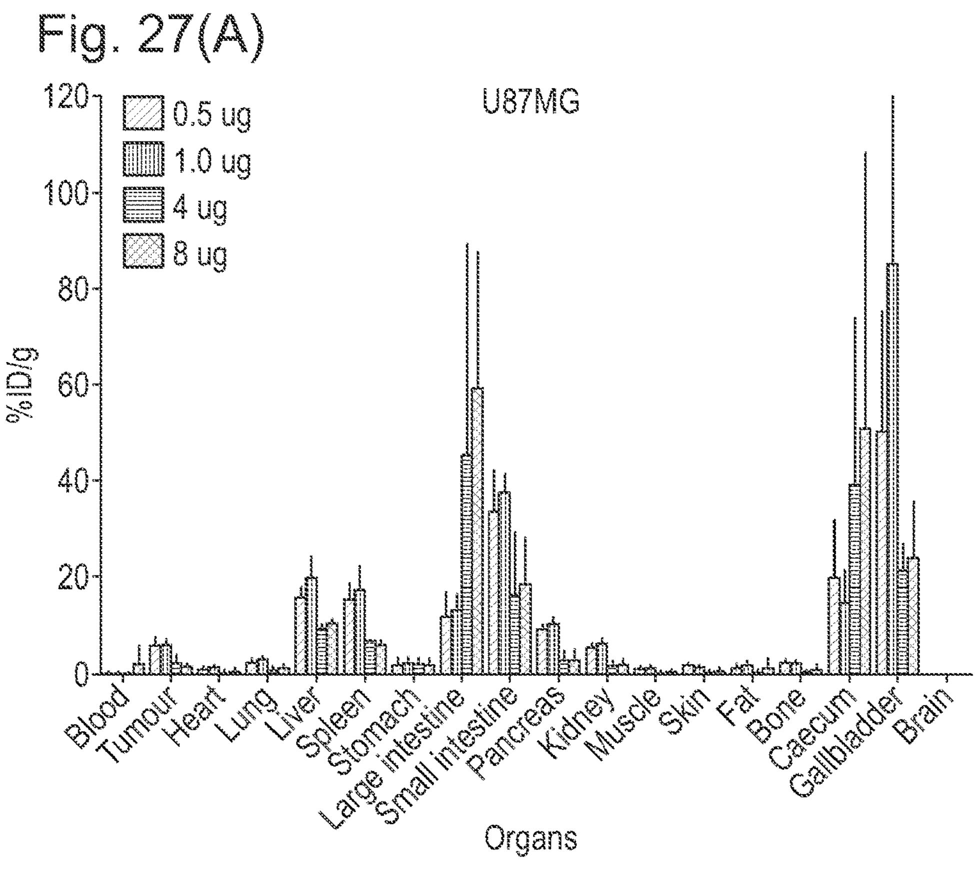
FIG. 27 shows two graphs of the biodistribution of $^{18}$F-olaparib in various organs of (a) U87MG and (b) U251MG tumour xenograft mouse models, after injection of $^{18}$F-olaparib at various doses. Each graph shows the percent injected dose of $^{18}$F-olaparib per gram (% ID/g) in each organ measured, after injection of (from left to right in the histogram for each organ) 0.5, 1.0, 4 and 8 μg $^{18}$F-olaparib.

4. In Vivo Studies of $^{18}F$-Olaparib in U87MG and U251MG Tumour Xenograft Mouse Models U87MG and U251MG xenografts were generated in Balb/c nude mice. The xenograft models were administered various doses (0.5, 1.0, 4.0, and 8.0 μg) of $^{18}F$-olaparib by tail vein injection. At 60-120 min post-injection, mice were sacrificed and organs were collected for biodistribution; see FIGS. 27(*a*) and (*b*), and FIG. 28(*a*). We show that tumour accumulation was dependent on the amount of the radiotracer which was injected. At 8.0 μg, the percent injected dose per gram of tumour (% ID/g) was significantly lower (>50%, P<0.001) in both U87MG and U251MG tumours compared to using 1.0 ug of the same tracer. We predicted that the uptake for the U251MG xenografts would be greater, but in vivo there is no significant difference between the % ID/g for the U251MG or U87MG xenograft tumours.

Figure 28A:
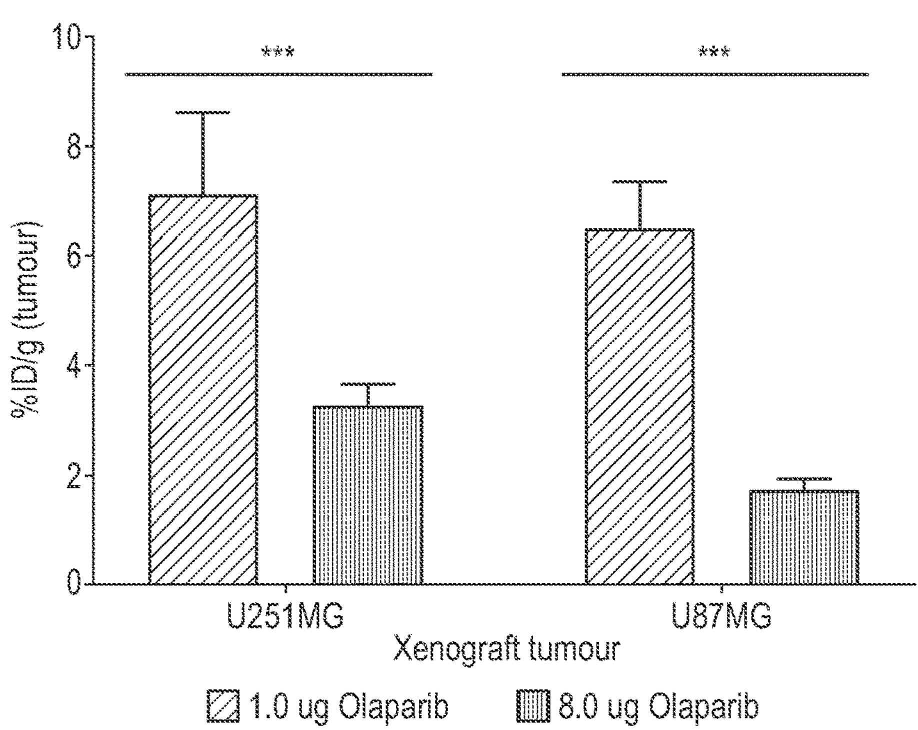
FIG. 28(*a*) shows that, at 8.0 μg, the percent injected dose per gram of tumour (% ID/g) was significantly lower (>50%, P<0.001) in both U87MG and U251MG tumours compared to using 1.0 ug of the same tracer.
Figure 28B:
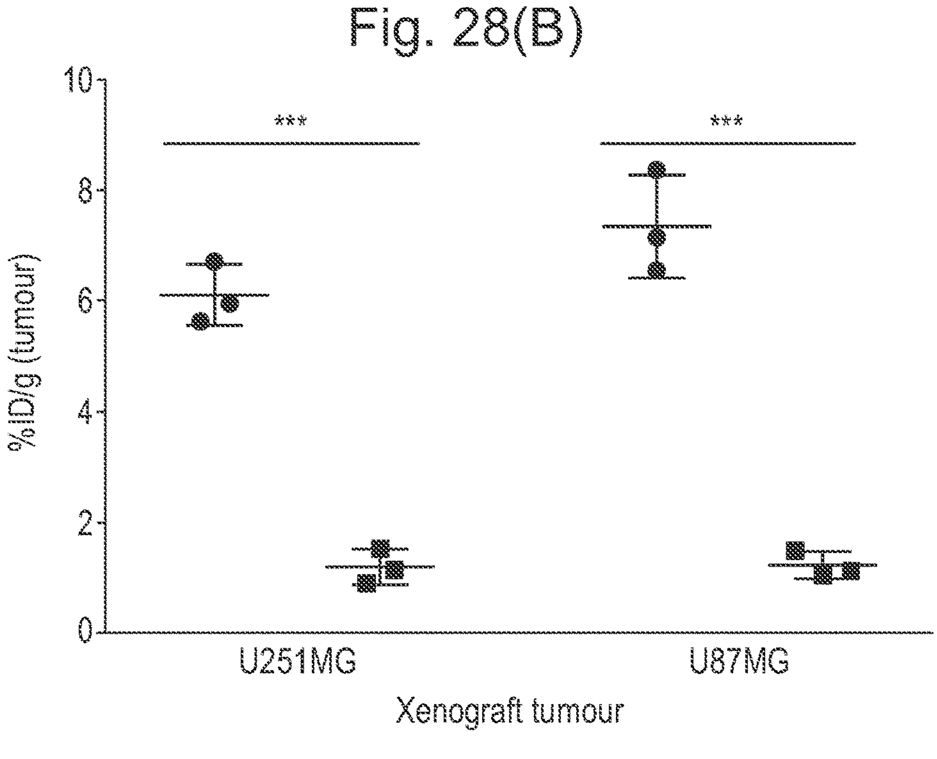

In a separate study—see FIG. 28(*b*)—we showed that we could also block the $^{18}F$-olaparib uptake using cold olaparib in vivo. A 20-fold excess of cold olaparib was injected via tail vein 60 m prior to 1 μg of $^{18}F$-olaparib via tail vein. The mice were sacrificed at 60-120 min post-injection and organs were harvested. FIG. 28(*b*) shows the % ID/g for the non-blocked and blocked tumours. Both tumours were successfully blocked by the cold olaparib.

5. Summary and Concluding Remarks

The uptake of $^{18}F$-olaparib in both U87MG and U251MG under in vitro cell culturing conditions or in vivo xenograft models is similar despite different PARP 1, 2, and 3 expressions. In addition, the tumour uptake for both xenograft models is significantly greater using 1 μg of the radiotracer as compared to larger doses of 4 μg or 8 μg. In vitro and in vivo, we demonstrate that cold olaparib successfully blocks our $^{18}F$-olaparib isotopologue. In vitro, 100 μM of cold olaparib blocks the uptake of 1 μM $^{18}F$-olaparib by 70%. In vivo, we achieved ~75% blocking using 20 μg of cold olaparib to block 1 μg of $^{18}F$-olaparib.

The work in Example 2 demonstrates that the radiolabelled compound, $^{18}F$-olaparib, has applications in brain cancer. The data also allow direct comparison, in the same mouse model, with data previously reported by others, and the tumour uptake of $^{18}F$-olaparib compares favourably.

The invention claimed is:

1. A process for producing a compound of formula (I)

(I)

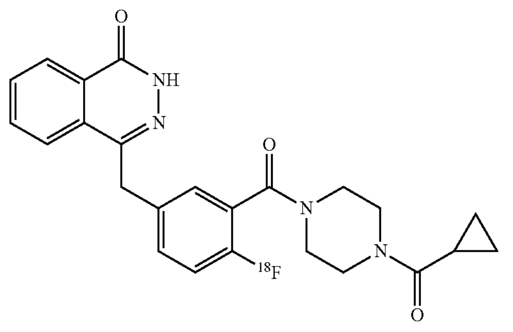

which process comprises:

(i) treating an organoboron compound of formula (II) with $^{18}F^-$ and a copper compound:

(II)

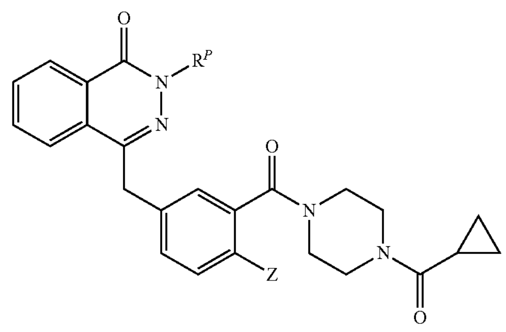

wherein

Z is a boronic ester group, a boronic acid group, a boronate group or a trifluoroborate group; and $R^P$ is a protecting group of formula (III)

(III)

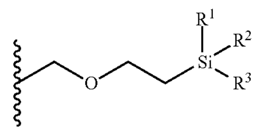

wherein $R^1$ is $C_{1-6}$ alkyl;

$R^2$ is $C_{1-6}$ alkyl; and $R^3$ is $C_{1-6}$ alkyl;

and (ii) removing the protecting group $R^P$ to produce the compound of formula (I).

2. The process according to claim 1, wherein the copper compound is a copper salt.

3. The process according to claim 1, wherein the copper compound is $[(impy)_4Cu^{II}(OTf)_2]$.

4. The process according to claim 3, wherein the $[(impy)_4Cu^{II}(OTf)_2]$ is formed in situ from impy and a compound of formula $[L_nCu(OTf)_2]$, wherein n is an integer from 0 to 4 and each L is a ligand other than impy.

5. The process according to claim 1, wherein Z is a group of formula (IV):

(IV)

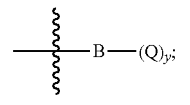

wherein:

each Q is the same or different and is a group selected from —$OR^E$, —OH, and fluoride;

each $R^E$ is the same or different and is a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, acyl, ester, amido, and haloalkyl, wherein two or more $R^E$ groups may be bonded together to form one or more rings; and y is 2 or 3.

6. The process according to claim 5, wherein Z is a group selected from

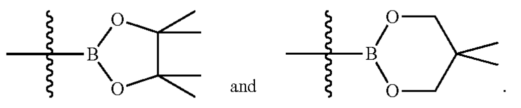

7. The process according to claim 1, wherein the copper compound is $[(impy)_4Cu^{II}(OTf)_2]$ and Z is

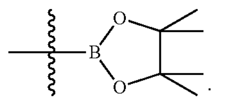 [SMILES: *B1OC(C)(C)C(C)(C)O1]

8. The process according to claim 1, wherein treating the organoboron compound of formula (II) with the $^{18}F^-$ and the copper compound is carried out in the presence of a solvent.

9. The process according to claim 8 wherein the solvent comprises 1,3-dimethyl-2-imidazolidinone (DMI), the copper compound is $[(impy)_4Cu^{II}(OTf)_2]$, Z is a boronic ester group, and the ratio of the amount of the organoboron compound to the amount of the copper compound is from 3:5 to 3:4.

10. The process according to claim 1, wherein the organoboron compound, the copper compound and the $^{18}F^-$ are heated at a temperature of from 80° C. to 150° C.

11. The process according to claim 1, wherein removing the protecting group $R^P$ comprises treatment with an acid, a source of boron trifluoride or a quaternary ammonium fluoride salt, optionally wherein removing the protecting group $R^P$ comprises treatment with an acid at a temperature of from 80° C. to 150° C.

* * * * *